US010351844B2

(12) United States Patent
Wu et al.

(10) Patent No.: US 10,351,844 B2
(45) Date of Patent: Jul. 16, 2019

(54) METHODS AND COMPOSITIONS FOR TREATING LEBER CONGENITAL AMAUROSIS

(71) Applicant: The United States of America, as represented by the Secretary Department of Health and Human Services, Washington, DC (US)

(72) Inventors: Zhijian Wu, Gaithersburg, MD (US); Anand Swaroop, Bethesda, MD (US); Suddhasil Mookherjee, Rockville, MD (US); Suja Hiriyanna, Boyds, MD (US)

(73) Assignee: The United States of America, as represented by the Secretary, Dept. of Health and Human Services, Washington, DC (US)

( * ) Notice: Subject to any disclaimer, the term of this patent is extended or adjusted under 35 U.S.C. 154(b) by 0 days.

(21) Appl. No.: 15/506,323

(22) PCT Filed: Aug. 27, 2015

(86) PCT No.: PCT/US2015/047209

§ 371 (c)(1),
(2) Date: Feb. 24, 2017

(87) PCT Pub. No.: WO2016/033338

PCT Pub. Date: Mar. 3, 2016

(65) Prior Publication Data

US 2017/0275615 A1 Sep. 28, 2017

Related U.S. Application Data

(60) Provisional application No. 62/042,703, filed on Aug. 27, 2014.

(51) Int. Cl.

| | |
|---|---|
| ***C12N 15/63*** | (2006.01) |
| ***C12N 15/10*** | (2006.01) |
| ***C07K 14/47*** | (2006.01) |
| ***A61K 31/7088*** | (2006.01) |
| ***C12N 9/22*** | (2006.01) |
| ***C12N 15/113*** | (2010.01) |
| ***C12N 15/86*** | (2006.01) |
| *A61K 48/00* | (2006.01) |

(52) U.S. Cl.

CPC ...... *C12N 15/1024* (2013.01); *A61K 31/7088* (2013.01); *C07K 14/4702* (2013.01); *C12N 9/22* (2013.01); *C12N 15/113* (2013.01); *C12N 15/86* (2013.01); *A61K 48/00* (2013.01); *A61K 48/005* (2013.01); *C12N 2310/10* (2013.01); *C12N 2750/14145* (2013.01)

(58) Field of Classification Search

None

See application file for complete search history.

(56) References Cited

U.S. PATENT DOCUMENTS

| | | | | |
|---|---|---|---|---|
| 2003/0104426 A1* | 6/2003 | Linsley | ................ | C12Q 1/6886 435/6.14 |
| 2016/0022836 A1* | 1/2016 | Banfi | .................. | C12N 15/113 424/450 |

OTHER PUBLICATIONS

Gao et al (PNAS, 2002. vol. 99, No. 18, pp. 11854-11859).*

Official Action for Canada Patent Application No. 2,959,540, dated Jul. 27, 2017 3 pages.

Official Actioin for European Patent Application No. 15760025.5, dated Jan. 4, 2018 3 pages.

International Search Report and Written Opinion prepared by the European Patent Office dated Nov. 4, 2015, for International Application No. PCT/US2015/047209.

L.M. Baye et al: "The N-terminal region of centrosomal protein 290 (CEP290) restores vision in a zebrafish model of human blindness", Human Molecular Genetics, vol. 20, No. 8, Apr. 15, 2011 (Apr. 4, 2011), pp. 1467-1477.

Database Geneseq [Online] Jun. 11, 2007, "Human CML marker gene, SEQ ID No. 158.", XP002750193, retrieved from EBI accession No. GSN: AEM95879.

Database EMBL [Online] May 17, 2012 "TSA: Macaca mulatta Mamu_551944 Mrna Sequence", xp002750194, retrieved from EBI accession No. EM_TSA:JV723973.

Database EMBL [Online] Nov. 30, 2000 (Nov. 30, 2000), "*Homo sapiens* CTCL tumor antigen se2-2 mRNA, partial cds.", XP002750195, retrieved from EBI accession No. EM_STD:AF273044.

Boye Shannon et al: "Natural History of Cone Disease in the Murine Model of Leber Congenital Amaurosis Due to CEP290 Mutation: Determining the Timing and Expectation of Therapy", PLOS ONE, vol. 9, No. 3, E92928, Mar. 2014 (Mar. 2014), pp. 1-12, XP002750196, p. 10.

Database Geneseq [Online] Oct. 23, 2014 (Oct. 23, 2014), "Human retinal dystrophy gene CEP290, SEQ ID:304.", XP002750198, retrieved from EBI accession No. GSN: BBM85064.

Official Action for Canada Patent Application No. 2,959,540, dated May 2, 2018 3 pages.

* cited by examiner

*Primary Examiner* — Celine X Qian

(74) *Attorney, Agent, or Firm* — Sheridan Ross P.C.

(57) ABSTRACT

Expression vectors, viral particles and therapeutic methods of using such constructs to improve the visual function of a patient suffering from diseases of the eye, resulting from failure to produce a specific protein in the eye, or the production of a non-functional protein in the eye, particularly Leber Congenital Amaurosis (LCA) and CEP290-related LCA.

7 Claims, 6 Drawing Sheets

Specification includes a Sequence Listing.

METHODS AND COMPOSITIONS FOR TREATING LEBER CONGENITAL AMAUROSIS

CROSS REFERENCE TO RELATED APPLICATIONS

This application is a national stage application under 35 U.S.C. 371 and claims the benefit of PCT Application No. PCT/US2015/047209 having an international filing date of 27 Aug. 2015, which designated the United States, which PCT application claimed the benefit of the U.S. Provisional Application No. 62/042,703, filed 27 Aug. 2014, the disclosure of each of which are incorporated herein by reference.

REFERENCE TO SEQUENCE LISTING

This application contains a Sequence Listing submitted as an electronic text file named "6137NEI-2-PCT_Sequence_Listing_ST25.txt", having a size in bytes of 236KB, and created on Aug. 27, 2015. The information contained in this electronic file is hereby incorporated by reference in its entirety pursuant to 37 CFR § 1.52(e)(5).

TECHNICAL FIELD

The invention relates to gene therapy and expression vectors and therapeutic methods of using such vectors in the treatment of diseases of the eye resulting from failure to produce a specific protein in the eye, or the production of a non-functional protein in the eye.

BACKGROUND

Leber congenital amaurosis (LCA) is an inherited eye disorder that primarily affects the retina, a specialized neuronal tissue at the back of the eye that detects light and color. People with this disease have severe visual impairment beginning in infancy. It occurs in 1 per 50,000 newborns and is one of the most common causes of blindness in children. So far, LCA-disease causing mutations have been identified in twenty-one genes. Mutations in the Centrosomal Protein 290 (CEP290) (NP_079390) gene account for 20-25 percent of LCA, afflicting an estimated 20,000 people worldwide. There is no treatment for this disease to date.

In recent years, gene therapy has emerged as a promising treatment modality for inherited eye disorders. Functional improvement has been achieved by gene therapy in patients with mutations in another gene, RPE65, which accounts for about 5% of LCA. Gene therapy for CEP290-related LCA (i.e., LCA caused by mutations in the CEP290 gene) has not been successful, even in animal models of the disease. A major reason for this lack of success is the difficulty of delivering the correct copy of CEP290 gene into the diseased retina due to the large size of the complete coding region. To treat LCA patients with CEP290 mutations, a correct copy of the CEP290 gene needs to be transferred into the patients' photoreceptor cells in their retinas. But the 7.4 kb size of the wild-type CEP290 cDNA significantly hampers its delivery into photoreceptors in the eye. Consequently, there is a need for an efficient treatment of CEP290-related LCA. The present invention addressees this need and achieves other advantages, which are discussed more fully below.

SUMMARY OF THE INVENTION

The present disclosure provides expression vectors and therapeutic methods of using the vectors for gene therapy to improve the visual function of a patient suffering from diseases of the eye, particularly Leber Congenital Amaurosis (LCA) and CEP290-related LCA. The invention relates to the inventors' surprising discovery that only a portion of the CEP290 coding region is necessary to restore proper CEP290 function in the eye, thereby improving visual function in individuals suffering from CEP290-related LCA.

Thus, one aspect of this disclosure is an isolated deoxyribonucleic acid (DNA) molecule comprising a nucleotide sequence at least 95% identical to at least a portion of a CEP290 open reading frame (ORF), wherein the nucleotide sequence encodes a protein that, when expressed in the photoreceptor cells of a patient suffering from CEP290-related Leber congenital amaurosis (LCA), increases the visual function of the patient. The portion of the CEP290 ORF may be less than a full-length CEP290 ORF. The portion of the CEP290 ORF may be less than 500 nucleotides in length. The CEP290 protein may be human CEP290. The portion of a CEP290 ORF may consist of SEQ ID NOs:4 or 10. The portion of CEP290 ORF may encode a protein at least 95% identical to SEQ ID NOs:4 or 10. The nucleotide sequence may encode a protein at least 95% identical to SEQ ID NOs:5 or 11 (referred to as the "myosin tail"; see FIG. 1). The nucleotide sequence may encode a protein comprising SEQ ID NOs:5 or 11. The nucleotide sequence may encode a protein comprising SEQ ID NO:8. The nucleotide sequence may be functionally linked to a photoreceptor cell-specific promoter.

Another aspect of this disclosure is a plasmid comprising the isolated DNA molecule comprising a nucleotide sequence at least 95% identical to at least a portion of a CEP290 gene open reading frame (ORF), wherein the nucleotide sequence encodes a protein that when expressed in the photoreceptor cells of a patient suffering from CEP290-related LCA, increases the visual function of the patient.

Another aspect of this disclosure is a vector comprising a deoxyribonucleic acid (DNA) molecule comprising a nucleotide sequence at least 95% identical to at least a portion of a CEP290 open reading frame (ORF), wherein the nucleotide sequence encodes a protein that when expressed in the photoreceptor cells of a patient suffering from CEP290-related LCA, increases the visual function of the patient. In these aspects, the vector may be a virus. The virus may be capable of transducing photoreceptor cells. The vector may be an adeno-associated virus. The vector may be a viral vector selected from the group consisting of AAV1, AAV2, AAV3, AAV5, AAV6, AAV7, AAV8, AAV9, and AAV10. The CEP290 may be human CEP290. The portion of a CEP290 ORF may consist of SEQ ID NO:4 or 10. The portion of a CEP290 ORF may encode a protein at least 95% identical to SEQ ID NO:11. The nucleotide sequence may encode a protein at least 95% identical to SEQ ID NO:5 or 11. The nucleotide sequence may encode a protein comprising SEQ ID NO:5 or 11. The nucleotide sequence may be functionally linked to a photoreceptor cell-specific promoter.

Another aspect of this disclosure is a pharmaceutical composition comprising a vector comprising a deoxyribonucleic acid (DNA) molecule comprising a nucleotide sequence at least 95% identical to at least a portion of a CEP290 open reading frame (ORF), wherein the nucleotide sequence encodes a protein that when expressed in the photoreceptor cells of a patient suffering from CEP290-related LCA, increases the visual function of the patient.

Another aspect of this disclosure provides methods of improving the visual function of a patient having CEP290-related LCA comprising administering an isolated DNA molecule comprising a nucleotide sequence at least 95% identical to at least a portion of a CEP290 open reading frame (ORF) to a patient in need thereof. The CEP290 may be human CEP290. The portion of a CEP290 ORF may consist of SEQ ID NO: 10. The portion of a CEP290 ORF may encode a protein at least 95% identical to SEQ ID NO:11. The nucleotide sequence may encode a protein at least 95% identical to SEQ ID NO:11. The nucleotide sequence may encode a protein comprising SEQ ID NO:11. The nucleotide sequence may be functionally linked to a photoreceptor cell-specific promoter. The isolated DNA molecule may be administered as naked DNA. The isolated DNA molecule may be coated with a transfection agent. The isolated DNA molecule may be in the form of a plasmid. The isolated DNA molecule may be administered in a viral vector. The viral vector is preferably capable of transducing photoreceptor cells. The administering may include subretinal injection of the isolated DNA molecule. The administering may include intravitreal injection of the isolated DNA molecule. Related aspects of this disclosure provide the use of an isolated DNA molecule comprising SEQ ID NO:10 in the manufacture of a medicament for the treatment of CEP290-related Leber Congenital Amaurosis. Another aspect provides an isolated DNA molecule comprising SEQ ID NO:10 for use in the treatment of CEP290-related Leber Congenital Amaurosis.

This Summary of the Invention is neither intended nor should it be construed as being representative of the full extent and scope of the invention. Aspects of the present invention are set forth in various levels of detail in this disclosure and no limitation as to the scope of the present invention is intended by either the inclusion or non-inclusion of elements, components, etc. in this Summary. Additional aspects of the present invention will become more readily apparent from the Description of Embodiments, particularly when taken together with the drawings.

BRIEF DESCRIPTION OF DRAWINGS

FIG. 2*a* shows the results of administration of the DSD fragment vector; FIG. 2*b* shows the results of administration of the myosin tail fragment vector; FIG. 2*c* shows the results of administration of the c-terminal vector. The control eyes were injected with an equal dose of viral particle with no expression cassette (null vector).

FIG. 3*a* shows the results of administration of 5e8 vg/eye of the myosin tail fragment vector; FIG. 3*b* shows the results of administration of 1e9 vg/eye of the myosin tail fragment vector; FIG. 3*c* shows the results of administration of 2e9 vg/eye of the myosin tail fragment vector.

DESCRIPTION OF EMBODIMENTS

Figure 1:
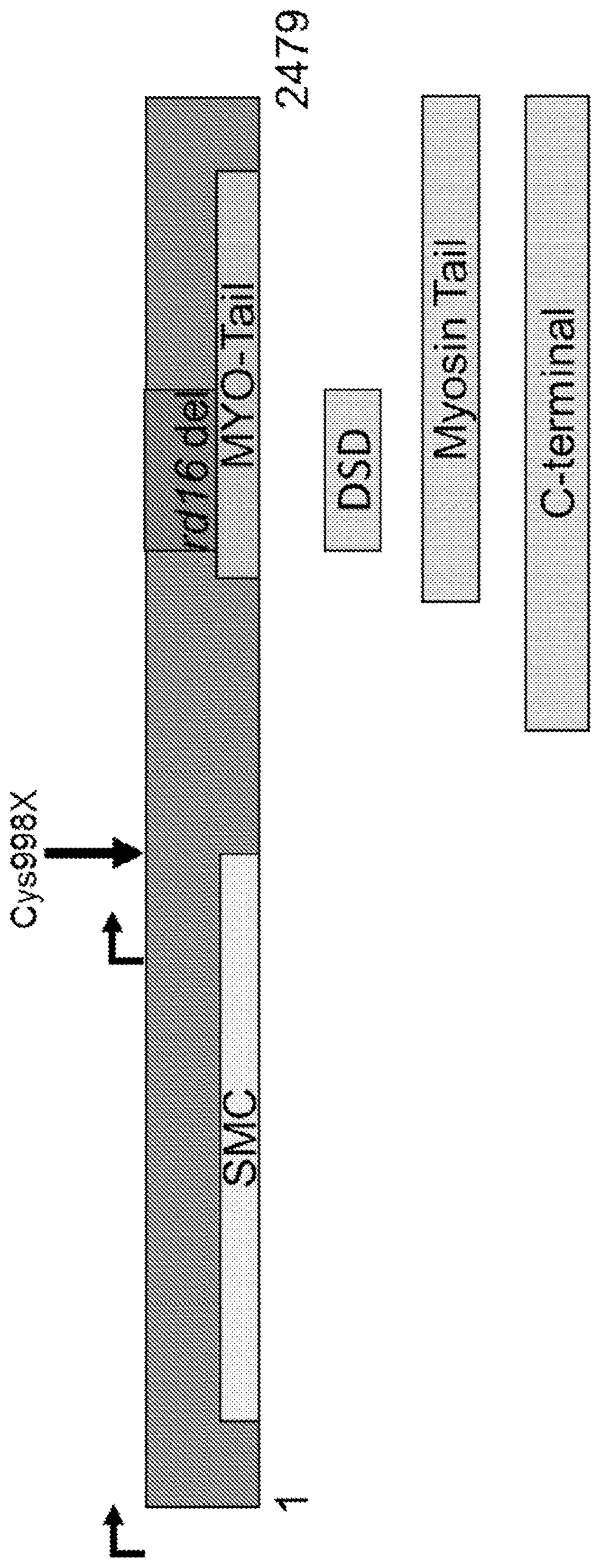
FIG. 1 is a schematic of the full-length CEP290 protein and the length and position of three CEP290 protein fragments (DSD, Myosin Tail, and C-terminal fragments) referenced in this disclosure. The position of the retinal dystrophy-16 (rd16) portion of the CEP290 protein is indicated. This portion of the CEP290 protein is absent in the Cep290 protein expressed by $Cep290^{rd16}$ mice, which have a phenotype that resembles LCA. The position of one CEP290 mutation (Cys998X), a splice-site change resulting in a premature stop codon, is also indicated. A region that has homology to SMC chromosome segregation ATPases, is also indicated.

The present disclosure relates to novel methods and compositions for treating Leber congenital amaurosis (LCA). More specifically, the present disclosure relates to novel nucleic acid molecules, and proteins encoded therein, that when administered to a patient suffering from LCA resulting from mutations in the CEP290 gene (herein "CEP290-related LCA"), are capable of improving visual function in the patient. The present invention also relates to vectors for administering such nucleic acid molecules as well as methods of administering such vectors in order to improve the visual function of a patient suffering from CEP290-related LCA.

As used herein and in the appended claims, the singular forms "a," "an," and "the" include plural referents unless the context clearly dictates otherwise. For example, a nucleic acid molecule refers to one or more nucleic acid molecules. As such, the terms "a", "an", "one or more" and "at least one" can be used interchangeably. Similarly the terms "comprising", "including" and "having" can be used interchangeably. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation The publications discussed herein are provided solely for their disclosure prior to the filing date of the present application. Nothing herein is to be construed as an admission that the present invention is not entitled to antedate such publication by virtue of prior invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments are specifically embraced by the present invention and are disclosed herein just as if each and every combination was individually and explicitly disclosed. In addition, all subcombinations are also specifically embraced by the present invention and are disclosed herein just as if each and every such sub-combination was individually and explicitly disclosed herein.

Previous attempts at treating CEP290-related LCA through the use of gene therapy have been unsuccessful due in large part to the difficulty in delivering the CEP290 coding region into the eye of the patient. In particular, the coding sequence for the full-length CEP290 protein is 7.4 kilobases (kb) in length, making it difficult to package the entire coding region into a single vector. The present inventors have surprisingly discovered that only a portion of the CEP290 coding region is necessary to restore proper CEP290 function and thus, improve visual function in individuals suffering from CEP290-related LCA. Thus, one aspect of the present invention is an isolated nucleic acid molecule (e.g., deoxyribonucleic acid (DNA) molecule) comprising a portion of a CEP290 open reading frame (ORF), wherein the portion of the CEP290 ORF is no more than about 5,000 nucleotides in length, and wherein the portion of the CEP290 ORF encodes a protein that is able to bind BBS6 protein, or that when expressed in photoreceptor cells in a patient suffering from CEP290-related LCA, increases the visual function of the patient.

As used herein, and with particular regard to amino acid and nucleotide sequences, the term "about" refers to a variation of +/−10%.

As used herein, "a portion of a CEP290 ORF" refers to at least 500 contiguous nucleotides from a CEP290 ORF, wherein the at least 500 contiguous nucleotides encode a protein having at least one activity specified herein, and wherein the portion of a CEP290 ORF does not comprise a full-length CEP290 ORF. That is, the portion of a CEP290 ORF is less than a full-length CEP290 ORF. The portion of the CEP290 ORF may comprise at least about 1,000, at least about 1,500, at least about 2,000, at least about 2,500, at least about 3,000, at least about 3,500, at least about 4,000, a least about 4,500 or at least about 5,000 contiguous nucleotides from a CEP290 ORF. Similarly, the portion of a CEP290 ORF may be less than about 4,500 nucleotides, less than about 4,000 nucleotides, less than about 3500 nucleotides, less than about 3,400 nucleotides, less than about 3,300 nucleotides, about 3,200 nucleotides, less than about 3,100, less than about 3,000 nucleotides, less than about 2,900 nucleotides, less than about 2,800 nucleotides, less than about 2,700, less than about 2,600 nucleotides, less than about 2,500 nucleotides, less than about 2,400 nucleotides, less than about 2,300 nucleotides, less than about 2,200 nucleotides, less than about 2,100, less than about 2,000 nucleotides, less than about 1,900 nucleotides, about 1,800 nucleotides, less than about 1,700 nucleotides, less than 1,600 nucleotides or less than about 1,500 nucleotides in length.

According to the present invention, a CEP290 open reading frame (ORF) refers to a series of contiguous nucleotides that does not contain any intron sequences or stop codons, and which encode a full-length CEP290 protein. The portion of a CEP290 ORF can be obtained from the CEP290 ORF of any animal, so long as the encoded protein possesses the desired activity. Desired activities include binding BBS6 protein (McKusick-Kaufman syndrome (MKS) and Bardet-Biedl syndrome (BBS) putative chaperonin protein) and/or improving the visual function of a patient suffering from CEP290-related LCA when the encoded protein is expressed in the cells of an eye of the patient. Examples of suitable animals from which to obtain the CEP290 sequence include, but are not limited to, humans and other primates, non-human primates such as chimpanzees and other apes and monkey species; farm animals such as cattle, sheep, pigs, seals, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. In one embodiment, the portion of a CEP290 ORF is obtained from a mouse CEP290 ORF. One mouse CEP290 ORF is represented by SEQ ID NO:1, which encodes a CEP290 protein represented by SEQ ID NO:2. In a preferred embodiment, the portion of a CEP290 ORF is obtained from a human CEP290 ORF. A human CEP290 ORF is represented by SEQ ID NO:7, which encodes a CEP290 protein represented by SEQ ID NO:8. Representative examples of useful CEP290 genes, portions thereof, and other sequences useful for producing constructs of the present invention, are listed below in Table 1.

TABLE 1

| SEQ ID NO | Description |
|---|---|
| 1 | Nucleotide sequence encoding mouse CEP290 protein |
| 2 | Protein encoded by SEQ ID NO: 1 |
| 3 | Complement of SEQ ID NO: 1 |
| 4 | Nucleotide sequence encoding mouse CEP290 myosin tail (2970 nts) |
| 5 | Protein encoded by SEQ ID NO: 4 (989 aa) |
| 6 | Complement of SEQ ID NO: 4 |
| 7 | Nucleotide sequence encoding human CEP290 protein |
| 8 | Protein encoded by SEQ ID NO: 7 |
| 9 | Complement of SEQ ID NO: 7 |
| 10 | Nucleotide sequence encoding human CEP290 myosin tail (2973 nts) |
| 11 | Protein encoded by SEQ ID NO: 10 (990 aa) |
| 12 | Complement of SEQ ID NO: 10 |
| 13 | Sequence of AAV2 ITR -upstream |
| 14 | Sequence of AAV2 ITR -downstream |
| 15 | Sequence of AAV2 terminal resolution site (trs) |
| 16 | Sequence of AAV2 REP binding site (RBS) |
| 17 | Sequence of human rhodopsin kinase promoter |
| 18 | Sequence of CMV IE promoter |
| 19 | Nucleotide sequence encoding AAV8 Cap protein |
| 20 | Protein encoded by SEQ ID NO: 17 |
| 21 | Complement of SEQ ID NO: 17 |
| 22 | Nucleotide sequence encoding mouse CEP290 DSD region (nts 4816-5712 of SEQ ID NO: 1) (896 nts) |
| 23 | Protein encoded by SEQ ID NO: 22 (aa 1606-1904 of SEQ ID NO: 2) (299 aa) |
| 24 | Complement of SEQ ID NO: 22 |
| 25 | Nucleotide sequence encoding human CEP290 DSD region (nts 4813-5709 of SEQ ID NO: 7) |
| 26 | Protein encoded by SEQ ID NO: 25 (299 aa) (aa 1605-1903 of SEQ ID NO: 8) |
| 27 | Complement of SEQ ID NO: 25 |
| 28 | Nucleotide sequence encoding mouse CEP290 C-terminal region (nts 3517-7440 of SEQ ID NO: 1) (3924 nts) |
| 29 | Protein encoded by SEQ ID NO: 28 (1307 aa) |
| 30 | Complement of SEQ ID NO: 28 |
| 31 | Nucleotide sequence encoding human CEP290 C-terminal region (nts 3517-7440 of SEQID NO: 7) |
| 32 | Protein encoded by SEQ ID NO: 31 (1307 aa) |
| 33 | Complement of SEQ ID NO: 31 |
| 34 | Nucleotide sequence of expression cassette - CMV-Mouse Myo tail-poly A |
| 35 | Nucleotide sequence of expression cassette - CMV-Human Myo tail-poly A |
| 36 | Nucleotide sequence of expression cassette - CMV-Mouse DSD -poly A |
| 37 | Nucleotide sequence of expression cassette - CMV-Human DSD -poly A |
| 38 | Nucleotide sequence of expression cassette - CMV-Mouse C-terminal-poly A |
| 39 | Nucleotide sequence of expression cassette - CMV-Human C-terminal-poly A |
| 40 | Nucleotide sequence of mouse Myo tail AAV expression vector |

TABLE 1-continued

| SEQ ID NO | Description |
|---|---|
| 41 | Nucleotide sequence of human Myo tail AAV expression vector |
| 42 | Nucleotide sequence of mouse DSD AAV expression vector |
| 43 | Nucleotide sequence of human DSD AAV expression vector |
| 44 | Nucleotide sequence of mouse C-terminal AAV expression vector |
| 45 | Nucleotide sequence of human C-terminal AAV expression vector |

It will be appreciated by those skilled in the art that genes found in nature often contain polymorphisms. A polymorphism, or variant, refers to a nucleic acid molecule (or its encoded protein), the sequence of which is similar, but not identical, to a reference sequence, often referred to as the wild-type sequence. While some sequence variations result in the reduction or elimination of the activity of the encoded protein, many have minimal or no effect on the activity of the encoded protein. According to the present invention, the portion of a CEP290 ORF can be obtained from any polymorphic variant of a CEP290 ORF, so long as the portion encodes a protein that is capable of increasing the visual function of a patient suffering from CEP290 related LCA.

Variations in the sequence of a CEP290 ORF, or portions thereof, used in the present invention may also be made through the use of genetic engineering techniques known to those skilled in the art. Examples of such techniques may be found in Sambrook J, Fritsch E F, Maniatis T et al., in Molecular Cloning-A Laboratory Manual, 2nd Edition, Cold Spring Harbor Laboratory Press, 1989, pp. 9.31-9.57, or in Current Protocols in Molecular Biology, John Wiley & Sons, N.Y. (1989), 6.3.1-6.3.6. With regard to such variants, any type of alteration in the nucleic acid sequence is permissible so long as the resulting variant protein retains the ability to increase the visual function of a patient suffering from CEP290-related LCA. Examples of such variations include, but are not limited to, deletions, insertions, substitutions and combinations thereof. For example, with regard to proteins, it is well understood by those skilled in the art that one or more (e.g., 2, 3, 4, 5, 6, 7, 8, 9 or 10), amino acids can often be removed from the amino and/or carboxyl terminal ends of a protein without significantly affecting the activity of that protein. Similarly, one or more (e.g., 2, 3, 4, 5, 6, 7, 8, 9 or 10) amino acids can often be inserted into a protein without significantly affecting the activity of the protein.

Any variation in the sequence of these proteins is permissible so long as the ability of the variant protein to increase visual function in the specified LCA patient is not significantly affected. In this regard, it is appreciated in the art that amino acids can be classified into groups based on their physical properties. Examples of such groups include, but are not limited to, charged amino acids, uncharged amino acids, polar uncharged amino acids, and hydrophobic amino acids. Preferred variants that contain substitutions are those in which an amino acid is substituted with an amino acid from the same group. Such substitutions are referred to as conservative substitutions. Naturally occurring residues may be divided into classes based on common side chain properties, as follows:

1) hydrophobic: Met, Ala, Val, Leu, Ile;
2) neutral hydrophilic: Cys, Ser, Thr;
3) acidic: Asp, Glu;
4) basic: Asn, Gln, His, Lys, Arg;
5) residues that influence chain orientation: Gly, Pro; and
6) aromatic: Trp, Tyr, Phe.

Non-conservative substitutions may involve the exchange of a member of one of these classes for a member from another class.

In making amino acid changes in the protein encoded by the portion of a CEP290 ORF, the hydropathic index of amino acids may be considered. Each amino acid has been assigned a hydropathic index on the basis of its hydrophobicity and charge characteristics. The hydropathic indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The importance of the hydropathic amino acid index in conferring interactive biological function on a protein is generally understood in the art (Kyte et al., 1982, J. Mol. Biol. 157:105-31). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those within ±1 are particularly preferred, and those within ±0.5 are even more particularly preferred.

It is also understood in the art that the substitution of like amino acids can be made effectively on the basis of hydrophilicity, particularly where the biologically functional equivalent protein or peptide thereby created is intended for therapeutic uses, as in the present case. The greatest local average hydrophilicity of a protein, as governed by the hydrophilicity of its adjacent amino acids, correlates with its immunogenicity and antigenicity, i.e., with one biological property of the protein. The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). In making changes based upon similar hydrophilicity values, the substitution of amino acids whose hydrophilicity values are within ±2 is preferred, those within ±1 are particularly preferred, and those within ±0.5 are even more particularly preferred.

Desired amino acid substitutions (whether conservative or non-conservative) can be determined by those skilled in the art at the time such substitutions are desired. For example, amino acid substitutions can be used to identify important residues of the therapeutic protein, or to increase or decrease the immunogenicity, solubility or stability of the therapeutic proteins described herein. Exemplary amino acid substitutions are shown in the following table:

Amino Acid Substitutions

| Original Amino Acid | Exemplary Substitutions |
|---|---|
| Ala | Val, Leu, Ile |
| Arg | Lys, Gln, Asn |
| Asn | Gln |
| Asp | Glu |
| Cys | Ser, Ala |
| Gln | Asn |
| Glu | Asp |
| Gly | Pro, Ala |

-continued

| Amino Acid Substitutions | |
|---|---|
| Original Amino Acid | Exemplary Substitutions |
| His | Asn, Gln, Lys, Arg |
| Ile | Leu, Val, Met, Ala |
| Leu | Ile, Val, Met, Ala |
| Lys | Arg, Gln, Asn |
| Met | Leu, Phe, Ile |
| Phe | Leu, Val, Ile, Ala, Tyr |
| Pro | Ala |
| Ser | Thr, Ala, Cys |
| Thr | Ser |
| Trp | Tyr, Phe |
| Tyr | Trp, Phe, Thr, Ser |
| Val | Ile, Met, Leu, Phe, Ala |

As used herein, the phrase "significantly affect a protein's activity" refers to a decrease in the activity of a protein by at least 20%, at least 30%, at least 40% or at least 50%. Methods of measuring such activities are known to those skilled in the art.

The portion of a CEP290 ORF may include a nucleotide sequence at least 85%, at least 90%, at least 95%, at least 98% or at least 99% identical to at least 500 contiguous nucleotides from a CEP290 ORF, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 750 contiguous nucleotides from a CEP290 ORF, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 1,000 contiguous nucleotides from a CEP290 ORF, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 1,500 contiguous nucleotides from a CEP290 ORF, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 2,000 contiguous nucleotides from a CEP290 ORF, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 2,500 contiguous nucleotides from a CEP290 ORF, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 2,700 contiguous nucleotides from a CEP290 ORF, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 2,800 contiguous nucleotides from a CEP290 ORF, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 2,900 contiguous nucleotides from a CEP290 ORF, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 3,000 contiguous nucleotides from a CEP290 ORF, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 3,500 contiguous nucleotides from a CEP290 ORF, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 4,000 contiguous nucleotides from a CEP290 ORF, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 4,500 contiguous nucleotides from a CEP290 ORF, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 5,000 contiguous nucleotides from a CEP290 ORF, wherein the portion encodes a protein that is capable of increasing visual function in a patient suffering from CEP290-related LCA.

While any portion of a CEP290 ORF having one or more of the desired activities described above can be used in the methods of the present disclosure, the inventors have discovered that particular portions of a CEP290 ORF are more suitable than others in increasing visual function in a patient suffering from CEP290-related LCA. Portions of a CEP290 ORF region corresponding to nucleotides 4471-7440 of SEQ ID NO:1, which is represented by SEQ ID NO:4, or nucleotides 4468-7440 of SEQ ID NO:7, which is represented by SEQ ID NO:10, are examples of such particularly suitable portions. It will be appreciated by those skilled in the art that due to the polymorphic variations previously described, variant CEP290 proteins, or CEP290 proteins from different species, can have slightly different sequences and as a result, may differ in length or sequence by a few amino acid residues. Thus, while the overall sequences of two or more variants may be nearly identical, the same (i.e., corresponding) region (e.g., domain) in two or more variants may differ slightly in sequence or may be slightly shifted upstream or downstream within the amino acid sequence relative to one another due to insertions or deletions. For example, amino acid residues 5-50 in one CEP290 protein may correspond to amino acid residues 4-49, 3-49, 3-51, 3-52, 5-5 or 3-56 in a variant CEP290 protein. As a more specific example, amino acid residues 257-292 of CEP290 from several species are predicted to form an amphipathic helix that is believed to mediate membrane binding of the protein. The corresponding region in CEP290 from organisms in the Genus *Danio* (minnow-type fish) spans amino acids 252-287 (J. of Clin. Invest., Vol. 123, No. 10, 2013). Consequently, as used herein, a region of an ORF (or protein) corresponding to a specified sequence (reference sequence) refers to a polynucleotide (or amino acid) sequence in the ORF (or protein) that is identical, or nearly so (e.g., 2%, 4%, 6%, 8%, 10%, 15% or 20% variation in sequence), in sequence to the reference sequence and which encodes (or is) a domain having the same structure and/or function.

Thus, the portion of a CEP290 ORF may include a nucleotide sequence at least 85%, at least 90%, at least 95%, at least 98% or at least 99% identical to at least 1,000, at least 1,500, at least 2,000, at least 2,500, at least 2,700, at least 2,800 or at least 2,900 contiguous nucleotides from region of a CEP290 ORF encoding the myosin tail domain (FIG. 1). Thus, the portion of a CEP290 ORF may include a nucleotide sequence at least 85%, at least 90%, at least 95%, at least 98% or at least 99% identical to at least 1,000 contiguous nucleotides from the region of a CEP290 ORF corresponding to nucleotides 4471-7440 of SEQ ID NO:1 or nucleotides 4468-7440 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 1,000 contiguous nucleotides from SEQ ID NO:4 or SEQ ID NO:10, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 1,500 contiguous nucleotides from the region of a CEP290 ORF corresponding to nucleotides 4471-7440 of SEQ ID NO:1 or nucleotides 4468-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 1,500 contiguous nucleotides from SEQ ID NO:4 or SEQ ID NO:10, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 2,000 contiguous nucleotides from the region of a CEP290 ORF corresponding to nucleotides 4471-7440 of SEQ ID NO:1 or nucleotides 4468-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 2,000 contiguous nucleotides from SEQ ID NO:4 or SEQ ID NO:10, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 2,500 contiguous nucleotides from the region of a CEP290 ORF corresponding to nucleotides 4471-7440 of SEQ ID NO:1 or nucleotides 4468-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 2,500 contiguous nucleotides from SEQ ID NO:4 or SEQ ID NO:10, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 2,700 contiguous nucleotides from the region of a CEP290 ORF corresponding to nucleotides 4471-7440 of SEQ ID NO:1 or nucleotides 4468-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 2,700 contiguous nucleotides from SEQ ID NO:4 or SEQ ID NO:10, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 2,800 contiguous nucleotides from the region of a CEP290 ORF corresponding to nucleotides 4471-7440 of SEQ ID NO:1 or nucleotides 4468-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 2,800 contiguous nucleotides from SEQ ID NO:4 or SEQ ID NO:10, wherein the portion encodes a protein that is capable of increasing visual function in a patient suffering from CEP290-related LCA.

The portion of a CEP290 ORF comprises a nucleotide sequence at least 85%, at least 90%, at least 95%, at least 98% or at least 99% identical to at least 2,900 contiguous nucleotides from the region of a CEP290 ORF corresponding to nucleotides 4471-7440 of SEQ ID NO:1 or nucleotides 4468-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 2,900 contiguous nucleotides from SEQ ID NO:4 or SEQ ID NO:10, wherein the portion encodes a protein that is capable of increasing visual function in a patient suffering from CEP290-related LCA.

The portion of a CEP290 ORF may include the nucleotide sequence of SEQ ID NO:4 or SEQ ID NO:10. In specific embodiments, the portion of a CEP290 ORF consists of SEQ ID NO:4 or SEQ ID NO:10.

As noted above, an isolated DNA molecule of the present invention encodes at least a portion of a CEP290 protein that is capable of increasing the visual function in a patient suffering from CEP290-related LCA. The portion of a CEP290 ORF may encode a protein comprising an amino acid sequence at least 85%, at least 90%, at least 95%, at least 97% or at least 99% identical to at least 500 contiguous amino acid residues from SEQ ID NO:5 or SEQ ID NO:11, wherein the portion of the CEP290 protein is capable of increasing visual function in a patient suffering from CEP290-related LCA. The portion of a CEP290 ORF may encode a protein comprising an amino acid sequence at least 85%, at least 90%, at least 95%, at least 97% or at least 99% identical to at least 600 contiguous amino acid residues from SEQ ID NO:5 or SEQ ID NO:11, wherein the portion of the CEP290 protein is capable of increasing visual function in a patient suffering from CEP290-related LCA. The portion of a CEP290 ORF may encode a protein comprising an amino acid sequence at least 85%, at least 90%, at least 95%, at least 97% or at least 99% identical to at least 700 contiguous amino acid residues from SEQ ID NO:5 or SEQ ID NO:11. The portion of a CEP290 ORF may encode a protein comprising an amino acid sequence at least 85%, at least 90%, at least 95%, at least 97% or at least 99% identical to at least 800 contiguous amino acid residues from SEQ ID NO:5 or SEQ ID NO:11, wherein the portion of the CEP290 protein is capable of increasing visual function in a patient suffering from CEP290-related LCA. The portion of a CEP290 ORF may encode a protein comprising an amino acid sequence at least 85%, at least 90%, at least 95%, at least 97% or at least 99% identical to at least 900 contiguous amino acid residues from SEQ ID NO:5 or SEQ ID NO:11, wherein the portion of the CEP290 protein is capable of increasing visual function in a patient suffering from CEP290-related LCA. The portion of a CEP290 ORF may encode a protein comprising an amino acid sequence at least 85%, at least 90%, at least 95%, at least 97% or at least 99% identical to at least 950 contiguous amino acid residues from SEQ ID NO:5 or SEQ ID NO:11, wherein the portion of the CEP290 protein is capable of increasing visual function in a patient suffering from CEP290-related LCA. The portion of a CEP290 ORF may encode a protein comprising an amino acid sequence at least 85%, at least 90%, at least 95%, at least 97% or at least 99% identical to at least 960 contiguous amino acid residues from SEQ ID NO:5 or SEQ ID NO:11, wherein the portion of the CEP290 protein is capable of increasing visual function in a patient suffering from CEP290-related LCA. The portion of a CEP290 ORF may encode a protein comprising an amino acid sequence at least 85%, at least 90%, at least 95%, at least 97% or at least 99% identical to at least 970 contiguous amino acid residues from SEQ ID NO:5 or SEQ ID NO:11, wherein the portion of the CEP290 protein is capable of increasing visual function in a patient suffering from CEP290-related LCA. The portion of a CEP290 ORF may encode a protein comprising an amino acid sequence at least 85%, at least 90%, at least 95%, at least 97% or at least 99% identical to at least 980 contiguous amino acid residues from SEQ ID NO:5 or SEQ ID NO:11, wherein the portion of the CEP290 protein is capable of increasing visual function in a patient suffering from CEP290-related LCA. The portion of a CEP290 ORF may encode a protein comprising an amino acid sequence at least 85%, at least 90%, at least 95%, at least 97% or at least 99% identical to SEQ ID NO:5 or SEQ ID NO:11, wherein the portion of the CEP290 protein is capable of increasing visual function in a patient suffering from CEP290-related LCA. The portion of a CEP290 ORF may encode a protein comprising SEQ ID NO:5 or SEQ ID NO:11. The portion of a CEP290 ORF may also encode a protein consisting of SEQ ID NO:5 or SEQ ID NO:11.

The portion of a CEP290 ORF may include a nucleotide sequence at least 85%, at least 90%, at least 95%, at least 98% or at least 99% identical to at least 300, at least 350, at least 400, at least 450, at least 500, at least 550, at least 600, at least 650, at least 700, at least 750, at least 800, or at least 850 contiguous nucleotides from the "deleted in sensory dystrophy" (DSD) domain of CEP290 ORF (FIG. 1). The portion of a CEP290 ORF may include a CEP290 ORF region corresponding to nucleotides 4816-5712 of SEQ ID NO:1, which is represented by SEQ ID NO:22, or nucleotides 4813-5709 of SEQ ID NO:7, which is represented by SEQ ID NO:25. The portion of a CEP290 ORF may include a nucleotide sequence at least 85%, at least 90%, at least 95%, at least 98% or at least 99% identical to at least 300 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF comprises a nucleotide sequence at least 85%, at least 90%, at least 95%, at least 98% or at least 99% identical to at least 300 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 350 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 350 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 400 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 400 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 450 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 450 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 500 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 500 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 550 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 550 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 600 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 600 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 650 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 650 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 700 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 700 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 750 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 750 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 800 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 800 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 850 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 850 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include SEQ ID NO:22 or SEQ ID NO:25. In specific embodiments, the portion of a CEP290 ORF consists of SEQ ID NO:22 or SEQ ID NO:25.

In one embodiment, an isolated DNA molecule of the present invention encodes protein comprising an amino acid sequence at least 85%, at least 90%, at least 95%, at least 97% or at least 99% identical to at least 100 contiguous amino acids, at least 150 contiguous amino acids, at least 200 contiguous amino acids, at least 250 contiguous amino acids, at least 275 contiguous amino acids or at least 290 contiguous amino acids, from a region of a CEP290 protein corresponding to the "deleted in sensory dystrophy" (DSD) domain (FIG. 1).

The portion of a CEP290 ORF encodes a protein comprising an amino acid sequence at least 85%, at least 90%, at least 95%, at least 97% or at least 99% identical to at least 100 contiguous amino acid residues from SEQ ID NO:23 or SEQ ID NO:26, wherein the CEP290 protein is capable of increasing visual function in a patient suffering from CEP290-related LCA. The portion of a CEP290 ORF encodes a protein comprising an amino acid sequence at least 85%, at least 90%, at least 95%, at least 97% or at least 99% identical to at least 150 contiguous amino acid residues from SEQ ID NO:23 or SEQ ID NO:26, wherein the CEP290 protein is capable of increasing visual function in a patient suffering from CEP290-related LCA. The portion of a CEP290 ORF encodes a protein comprising an amino acid sequence at least 85%, at least 90%, at least 95%, at least 97% or at least 99% identical to at least 200 contiguous amino acid residues from SEQ ID NO:23 or SEQ ID NO:26. The portion of a CEP290 ORF encodes a protein comprising an amino acid sequence at least 85%, at least 90%, at least 95%, at least 97% or at least 99% identical to at least 250 contiguous amino acid residues from SEQ ID NO:23 or SEQ ID NO:26, wherein the CEP290 protein is capable of increasing visual function in a patient suffering from CEP290-related LCA. The portion of a CEP290 ORF encodes a protein comprising an amino acid sequence at least 85%, at least 90%, at least 95%, at least 97% or at least 99% identical to at least 275 contiguous amino acid residues from SEQ ID NO:23 or SEQ ID NO:26, wherein the CEP290 protein is capable of increasing visual function in a patient suffering from CEP290-related LCA. The portion of a CEP290 ORF encodes a protein comprising an amino acid sequence at least 85%, at least 90%, at least 95%, at least 97% or at least 99% identical to at least 290 contiguous amino acid residues from SEQ ID NO:23 or SEQ ID NO:26, wherein the CEP290 protein is capable of increasing visual function in a patient suffering from CEP290-related LCA. The portion of a CEP290 ORF encodes a protein comprising an amino acid sequence at least 85%, at least 90%, at least 95%, at least 97% or at least 99% identical to SEQ ID NO:23 or SEQ ID NO:26, wherein the CEP290 protein is capable of increasing visual function in a patient suffering from CEP290-related LCA. The portion of a CEP290 ORF encode a protein comprising an amino acid sequence comprising SEQ ID NO:23 or SEQ ID NO:26. The portion of a CEP290 ORF encode a protein consisting of SEQ ID NO:23 or SEQ ID NO:26.

The portion of a CEP290 ORF may include a nucleotide sequence at least 85%, at least 90%, at least 95%, at least 98% or at least 99% identical to at least 1,000, at least 1,500, at least 2,000, at least 2,500, at least 3,000, at least 3,200, at least 3,500, at least 3,700, at least 3,800 or at least 3,900 contiguous nucleotides from the region of the CEP290 ORF encoding the C-Terminal domain (FIG. 1). The portion of a CEP290 ORF may include a CEP290 ORF region corresponding to nucleotides 3517-7440 of SEQ ID NO:1, which is represented by SEQ ID NO:28, or nucleotides 3517-7440 of SEQ ID NO:7, which is represented by SEQ ID NO:31. The portion of a CEP290 ORF may include a nucleotide sequence at least 85%, at least 90%, at least 95%, at least 98% or at least 99% identical to at least 1,000 contiguous nucleotides from the region of a CEP290 ORF corresponding to nucleotides 3517-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 1,000 contiguous nucleotides from SEQ ID NO:28 or SEQ ID NO:31, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 1,500 contiguous nucleotides from the region of a CEP290 ORF corresponding to nucleotides 3517-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 1,500 contiguous nucleotides from SEQ ID NO:28 or SEQ ID NO:31, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 2,000 contiguous nucleotides from the region of a CEP290 ORF corresponding to nucleotides 3517-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 2,000 contiguous nucleotides from SEQ ID NO:28 or SEQ ID NO:31, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 2,500 contiguous nucleotides from the region of a CEP290 ORF corresponding to nucleotides 3517-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 2,500 contiguous nucleotides from SEQ ID NO:28 or SEQ ID NO:31, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 3,000 contiguous nucleotides from the region of a CEP290 ORF corresponding to nucleotides 3517-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 2,700 contiguous nucleotides from SEQ ID NO:28 or SEQ ID NO:31, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 3,200 contiguous nucleotides from the region of a CEP290 ORF corresponding to nucleotides 3517-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 3,200 contiguous nucleotides from SEQ ID NO:28 or SEQ ID NO:31, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 3,500 contiguous nucleotides from the region of a CEP290 ORF corresponding to nucleotides 3517-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 3,500 contiguous nucleotides from SEQ ID NO:28 or SEQ ID NO:31, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 3,700 contiguous nucleotides from the region of a CEP290 ORF corresponding to nucleotides 3517-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 3,700 contiguous nucleotides from SEQ ID NO:28 or SEQ ID NO:31, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 3,800 contiguous nucleotides from the region of a CEP290 ORF corresponding to nucleotides 3517-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 3,800 contiguous nucleotides from SEQ ID NO:28 or SEQ ID NO:31, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 3,900 contiguous nucleotides from the region of a CEP290 ORF corresponding to nucleotides 3517-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 3,900 contiguous nucleotides from SEQ ID NO:28 or SEQ ID NO:31, wherein the portion encodes a protein that is capable of increasing visual function in a patient suffering from CEP290-related LCA.

The portion of a CEP290 ORF may include SEQ ID NO:28 or SEQ ID NO:31. In specific embodiments, the portion of a CEP290 ORF consists of SEQ ID NO:28 or SEQ ID NO:31.

As noted above, an isolated DNA molecule of the present invention encodes a CEP290 protein that is capable of increasing the visual function in a patient suffering from CEP290-related LCA. The portion of a CEP290 ORF encodes a protein comprising an amino acid sequence at least 85%, at least 90%, at least 95%, at least 97% or at least 99% identical to at least 500 contiguous amino acid residues from SEQ ID NO:28 or SEQ ID NO:31, wherein the CEP290 protein is capable of increasing visual function in a patient suffering from CEP290-related LCA. The portion of a CEP290 ORF encodes a protein comprising an amino acid sequence at least 85%, at least 90%, at least 95%, at least 97% or at least 99% identical to at least 600 contiguous amino acid residues from SEQ ID NO:28 or SEQ ID NO:31, wherein the CEP290 protein is capable of increasing visual function in a patient suffering from CEP290-related LCA. The portion of a CEP290 ORF encodes a protein comprising an amino acid sequence at least 85%, at least 90%, at least 95%, at least 97% or at least 99% identical to at least 700 contiguous amino acid residues from SEQ ID NO:28 or SEQ ID NO:31. The portion of a CEP290 ORF encodes a protein comprising an amino acid sequence at least 85%, at least 90%, at least 95%, at least 97% or at least 99% identical to at least 800 contiguous amino acid residues from SEQ ID NO:28 or SEQ ID NO:31, wherein the CEP290 protein is capable of increasing visual function in a patient suffering from CEP290-related LCA. The portion of a CEP290 ORF encodes a protein comprising an amino acid sequence at least 85%, at least 90%, at least 95%, at least 97% or at least 99% identical to at least 900 contiguous amino acid residues from SEQ ID NO:28 or SEQ ID NO:31, wherein the CEP290 protein is capable of increasing visual function in a patient suffering from CEP290-related LCA. The portion of a CEP290 ORF encodes a protein comprising an amino acid sequence at least 85%, at least 90%, at least 95%, at least 97% or at least 99% identical to at least 1000 contiguous amino acid residues from SEQ ID NO:28 or SEQ ID NO:31, wherein the CEP290 protein is capable of increasing visual function in a patient suffering from CEP290-related LCA. The portion of a CEP290 ORF encodes a protein comprising an amino acid sequence at least 85%, at least 90%, at least 95%, at least 97% or at least 99% identical to at least 1,100 contiguous amino acid residues from SEQ ID NO:28 or SEQ ID NO:31, wherein the CEP290 protein is capable of increasing visual function in a patient suffering from CEP290-related LCA. The portion of a CEP290 ORF encodes a protein comprising an amino acid sequence at least 85%, at least 90%, at least 95%, at least 97% or at least 99% identical to at least 1,200 contiguous amino acid residues from SEQ ID NO:28 or SEQ ID NO:31, wherein the CEP290 protein is capable of increasing visual function in a patient suffering from CEP290-related LCA. The portion of a CEP290 ORF encodes a protein comprising an amino acid sequence at least 85%, at least 90%, at least 95%, at least 97% or at least 99% identical to at least 1,250 contiguous amino acid residues from SEQ ID NO:28 or SEQ ID NO:31, wherein the CEP290 protein is capable of increasing visual function in a patient suffering from CEP290-related LCA. The portion of a CEP290 ORF encodes a protein comprising an amino acid sequence at least 85%, at least 90%, at least 95%, at least 97% or at least 99% identical to at least 1,300 contiguous amino acid residues from SEQ ID NO:28 or SEQ ID NO:31, wherein the CEP290 protein is capable of increasing visual function in a patient suffering from CEP290-related LCA. The portion of a CEP290 ORF encodes a protein comprising an amino acid sequence at least 85%, at least 90%, at least 95%, at least 97% or at least 99% identical to SEQ ID NO:28 or SEQ ID NO:31, wherein the CEP290 protein is capable of increasing visual function in a patient suffering from CEP290-related LCA. The portion of a CEP290 ORF encode a protein comprising SEQ ID NO:28 or SEQ ID NO:31. The portion of a CEP290 ORF encode a protein consisting of SEQ ID NO:28 or SEQ ID NO:31.

Isolated DNA molecules of the present invention are useful for expressing CEP290 protein when introduced into the eye of a patient suffering from CEP290-related LCA in such a manner suitable for delivery of the DNA molecules to cells of the eye. Thus, preferred DNA molecules of the present invention include a promoter sequence that is functionally linked to the portion of a CEP290 ORF. As used herein, the term functionally linked refers to the fact that the promoter is connected to a nucleotide sequence containing an open-reading frame such that when the construct is placed into the appropriate conditions, the promoter causes transcription (expression) of the open reading frame. Any promoter can be used so long as it is capable of driving expression of the ORF. Because molecules of the present invention are meant for treating conditions of the eye, preferred promoters are those that are functional in cells of the eye. The promoter is functional when introduced into the eye of a patient. The promoter is specific for cells of the eye. The promoter is functional when introduced into photoreceptor cells. The promoter is specific for photoreceptor cells. The promoter is a rhodopsin promoter. The promoter is a rhodopsin kinase promoter. The promoter sequence may include SEQ ID NO:17. The promoter may be an Interstitial retinol-binding protein (IRBP promoter). The promoter may be a cytomegalovirus (CMV) promoter. The promoter may be a CMV intermediate-early (IE) promoter. The promoter may be a sequence consisting of SEQ ID NO:18.

One aspect of the present disclosure is a vector comprising an isolated DNA molecule of the present disclosure. As used herein, a vector is any agent comprising an isolated DNA molecule of the present disclosure that can be used to deliver a DNA molecule of the present disclosure into a cell. Examples of suitable vectors include, but are not limited to, plasmids, cosmids, phage and viruses. In one aspect, the vector is a virus. It will be appreciated by those skilled in the art that, in some instances, packaging of heterologous DNA into a virus requires specific sequences from the DNA of the virus into which the heterologous DNA is being packaged. Thus, an isolated DNA molecule of the present invention may include viral DNA that allows for packaging of the isolated DNA molecule into a virus. Any viral vector can be used to package isolated DNA of the present invention, so long as the virus is capable of containing the DNA and delivering it to the cells of an eye of a patient in need of such treatment.

One example of a suitable viral vector for use in the present invention is adeno-associated virus. Adeno-associated viruses are small, replication-defective, non-enveloped viruses that belong to the family Parvoviridae. The Parvoviridae family is characterized by having a single-stranded linear DNA genome of about 4,800 nucleotides and a small icosahedral shaped capsid measuring about 20 nm in diameter. The AAV genome contains two open reading frames called ‘rep’ and ‘cap.’ The rep ORF encodes all of the non-structural proteins that are necessary for replication and packaging of the viral genome, while the cap ORF encodes the viral capsid proteins. The viral capsid proteins are the structural proteins of the virus and assemble into the viral particle.

The AAV genome is terminated at each end by an inverted terminal repeat (ITR) of approximately 150 nucleotides in length. The sequences of the ITRs are palindromes that fold back on themselves to form T-shaped hairpin structures. Each ITR contains a Rep binding site (RBS) and a sequence referred to as the terminal resolution site (trs), which is cleaved by the viral Rep protein. These sequences in the ITR are important for replication and packaging of the viral genome. Thus, the ITRs can be combined with DNA molecules of the present invention to produce nucleic acid molecules that can be packaged into AAV particles and/or virus-like particles. Similar use of ITRs is described in U.S. Pat. No. 8,927,269, the entirety of which is incorporated herein by reference. Thus, an isolated DNA molecule of the present invention may be flanked by ITR sequences, wherein at least one ITR comprises AAV sequences that allow packaging of the DNA molecule into an AAV particle. The AAV sequences may be from an AAV ITR. At least one ITR may include an AAV RBS and a trs. At last one ITR may include SEQ ID NO:16 and SEQ ID NO:15. At least one ITR may be at least 85%, at least 90%, at least 95% or at least 97% identical to an AAV ITR, wherein the ITR comprises a RBS and a trs. An isolated DNA molecule of the present disclosure may be flanked by ITRs from an AAV virus. The ITRs can contain sequence from any AAV, so long as the virus strain from which the ITRs are obtained is capable of delivering the packaged DNA into a cell of the eye. An isolated DNA molecule of the present invention may be flanked by ITRs from a virus selected from the group consisting of AAV2, AAV3, AAV5, AAV6, AAV7, AAV8, AAV9 and AAV10. The ITRs may include a sequence selected from SEQ ID NO:13 and SEQ ID NO:14.

One aspect of the present disclosure is an isolated nucleic acid molecule of the present invention flanked by ITRs. Another aspect of the present invention is an isolated nucleic acid molecule comprising: a) a pair of inverted terminal repeats (ITRs), each of which is capable of forming a T-shaped hairpin structure, wherein at least one inverted terminal repeat comprises an AAV RBS and an AAV trs; and, b) a polynucleotide sequence between the terminal repeats, wherein the polynucleotide sequence comprises at least a portion of a CEP290 protein. Examples of suitable portions of a CEP290 protein have been described above.

Another aspect of this disclosure is an isolated nucleic acid molecule comprising: a) a pair of inverted terminal repeats (ITRs), each of which is capable of forming a T-shaped hairpin structure, wherein at least one inverted terminal repeat comprises an AAV RBS and an AAV trs; and, b) a polynucleotide sequence between the terminal repeats, wherein the polynucleotide sequence comprises at least a portion of a CEP290 ORF functionally linked to a promoter, wherein the portion of the CEP290 ORF is no more than 5000 nucleotides in length and encodes a protein that when expressed in the photoreceptor cells of a patient suffering from CEP-290-related LCA, increases the visual function of the patient. The AAV trs may include SEQ ID NO:15. The AAV RBS may include SEQ ID NO:16. Each ITR may include an AAV RBS and an AAV tsr. The ITRs may independently include a nucleic acid sequence at least 80% identical to an ITR from a virus selected from the group consisting of AAV2, AAV3, AAV5, AAV6, AAV7, AAV8, AAV9 and AAV10, wherein at least one ITR comprises an AAV Rep site and an AAV trs. The ITRs may independently include a nucleic acid sequence at least 95% identical to an ITR from a virus selected from the group consisting of AAV2, AAV3, AAV5, AAV6, AAV7, AAV8, AAV9 and AAV10, wherein at least one ITR comprises an AAV Rep site and an AAV trs. The ITRs may independently include an ITR from a virus selected from the group consisting of AAV2, AAV3, AAV5, AAV6, AAV7, AAV8, AAV9 and AAV10. The ITRs may include a sequence selected from SEQ ID NO:13 and SEQ ID NO:14.

The portion of CEP290 ORF may include a nucleotide sequence at least 85%, at least 90%, at least 95%, at least 98% or at least 99% identical to at least 1,000 contiguous nucleotides from the region of a CEP290 ORF corresponding to nucleotides 4471-7440 of SEQ ID NO:1 or nucleotides 4468-7440 of SEQ ID NO:7, wherein the portion encodes a protein that is capable of increasing visual function in a patient suffering from CEP290-related LCA. The portion of CEP290 ORF may include a nucleotide sequence at least 85%, at least 90%, at least 95%, at least 98% or at least 99% identical to at least 1,000 contiguous nucleotides from SEQ ID NO:4 or SEQ ID NO:10, wherein the portion encodes a protein that is capable of increasing visual function in a patient suffering from CEP290-related LCA.

The portion of CEP290 ORF may include a nucleotide sequence at least 85%, at least 90%, at least 95%, at least 98% or at least 99% identical to at least 1,500 contiguous nucleotides from the region of a CEP290 ORF corresponding to nucleotides 4471-7440 of SEQ ID NO:1 or nucleotides 4468-7440 of, wherein the portion encodes a protein that is capable of increasing visual function in a patient suffering from CEP290-related LCA. The portion of CEP290 ORF may include a nucleotide sequence at least 85%, at least 90%, at least 95%, at least 98% or at least 99% identical to at least 1,500 contiguous nucleotides from SEQ ID NO:4 or SEQ ID NO:10, wherein the portion encodes a protein that is capable of increasing visual function in a patient suffering from CEP290-related LCA.

The portion of CEP290 ORF may include a nucleotide sequence at least 85%, at least 90%, at least 95%, at least 98% or at least 99% identical to at least 2,000 contiguous nucleotides from the region of a CEP290 ORF corresponding to nucleotides 4471-7440 of SEQ ID NO:1 or nucleotides 4468-7440 of, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 2,000 contiguous nucleotides from SEQ ID NO:4 or SEQ ID NO:10, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 2,500 contiguous nucleotides from the region of a CEP290 ORF corresponding to nucleotides 4471-7440 of SEQ ID NO:1 or nucleotides 4468-7440 of, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 2,500 contiguous nucleotides from SEQ ID NO:4 or SEQ ID NO:10, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 2,700 contiguous nucleotides from the region of a CEP290 ORF corresponding to nucleotides 4471-7440 of SEQ ID NO:1 or nucleotides 4468-7440 of, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 2,700 contiguous nucleotides from SEQ ID NO:4 or SEQ ID NO:10, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 2,800 contiguous nucleotides from the region of a CEP290 ORF corresponding to nucleotides 4471-7440 of SEQ ID NO:1 or nucleotides 4468-7440 of, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 2,800 contiguous nucleotides from SEQ ID NO:4 or SEQ ID NO:10, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 2,900 contiguous nucleotides from the region of a CEP290 ORF corresponding to 4471-7440 of SEQ ID NO:1 or nucleotides 4468-7440 of, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 2,900 contiguous nucleotides from SEQ ID NO:4 or SEQ ID NO:10, wherein the portion encodes a protein that is capable of increasing visual function in a patient suffering from CEP290-related LCA.

The portion of a CEP290 ORF may include SEQ ID NO:4 or SEQ ID NO:10. In specific embodiments, the portion of CEP290 ORF consists of SEQ ID NO:4 or SEQ ID NO:10.

The portion of a CEP290 ORF may include a nucleotide sequence at least 85%, at least 90%, at least 95%, at least 98% or at least 99% identical to at least 300, at least 350, at least 400, at least 450, at least 500, at least 550, at least 600, at least 650, at least 700, at least 750, at least 800, or at least 850 contiguous nucleotides from the DSD domain of CEP290 ORF. The portion of a CEP290 ORF may include a CEP290 ORF region corresponding to nucleotides 4816-5712 of SEQ ID NO:1, which is represented by SEQ ID NO:22, or nucleotides 4813-5709 of SEQ ID NO:7, which is represented by SEQ ID NO:25. The portion of a CEP290 ORF may include a nucleotide sequence at least 85%, at least 90%, at least 95%, at least 98% or at least 99% identical to at least 300 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 300 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 350 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 350 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 400 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 400 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 450 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 450 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 500 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 500 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 550 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 550 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 600 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 600 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 650 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 650 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 700 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 700 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 750 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 750 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 800 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 800 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 850 contiguous nucleotides from the region of a CEP290 ORF corresponding to nucleotides 4816-5712 of SEQ ID NO:1, or nucleotides 4813-5709 of SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 850 contiguous nucleotides from SEQ ID NO:22 or SEQ ID NO:25, wherein the portion encodes a protein that is capable of increasing visual function in a patient suffering from CEP290-related LCA.

The portion of a CEP290 ORF may include SEQ ID NO:22 or SEQ ID NO:25. In specific embodiments, the portion of a CEP290 ORF consists of SEQ ID NO:22 or SEQ ID NO:25.

An isolated DNA molecule of the present disclosure may encode protein comprising an amino acid sequence at least 85%, at least 90%, at least 95%, at least 97% or at least 99% identical to at least 100 contiguous amino acids, at least 150 contiguous amino acids, at least 200 contiguous amino acids, at least 250 contiguous amino acids, at least 275 contiguous amino acids or at least 290 contiguous amino acids, from a region of a CEP290 protein corresponding to the DSD region.

The portion of a CEP290 ORF may encode a protein comprising an amino acid sequence at least 85%, at least 90%, at least 95%, at least 97% or at least 99% identical to at least 100 contiguous amino acid residues from SEQ ID NO:23 or SEQ ID NO:26, wherein the CEP290 protein is capable of increasing visual function in a patient suffering from CEP290-related LCA. The portion of a CEP290 ORF may encode a protein comprising an amino acid sequence at least 85%, at least 90%, at least 95%, at least 97% or at least 99% identical to at least 150 contiguous amino acid residues from SEQ ID NO:23 or SEQ ID NO:26, wherein the CEP290 protein is capable of increasing visual function in a patient suffering from CEP290-related LCA. The portion of a CEP290 ORF may encode a protein comprising an amino acid sequence at least 85%, at least 90%, at least 95%, at least 97% or at least 99% identical to at least 200 contiguous amino acid residues from SEQ ID NO:23 or SEQ ID NO:26. The portion of a CEP290 ORF may encode a protein comprising an amino acid sequence at least 85%, at least 90%, at least 95%, at least 97% or at least 99% identical to at least 250 contiguous amino acid residues from SEQ ID NO:23 or SEQ ID NO:26, wherein the CEP290 protein is capable of increasing visual function in a patient suffering from CEP290-related LCA. The portion of a CEP290 ORF may encode a protein comprising an amino acid sequence at least 85%, at least 90%, at least 95%, at least 97% or at least 99% identical to at least 275 contiguous amino acid residues from SEQ ID NO:23 or SEQ ID NO:26, wherein the CEP290 protein is capable of increasing visual function in a patient suffering from CEP290-related LCA. The portion of a CEP290 ORF may encode a protein comprising an amino acid sequence at least 85%, at least 90%, at least 95%, at least 97% or at least 99% identical to at least 290 contiguous amino acid residues from SEQ ID NO:23 or SEQ ID NO:26, wherein the CEP290 protein is capable of increasing visual function in a patient suffering from CEP290-related LCA. The portion of a CEP290 ORF may encode a protein comprising an amino acid sequence at least 85%, at least 90%, at least 95%, at least 97% or at least 99% identical to SEQ ID NO:23 or SEQ ID NO:26, wherein the CEP290 protein is capable of increasing visual function in a patient suffering from CEP290-related LCA. The portion of a CEP290 ORF may encode a protein comprising an amino acid sequence comprising SEQ ID NO:23 or SEQ ID NO:26. The portion of a CEP290 ORF may encode a protein consisting of SEQ ID NO:23 or SEQ ID NO:26.

The portion of a CEP290 ORF may include a nucleotide sequence at least 85%, at least 90%, at least 95%, at least 98% or at least 99% identical to at least 1,000, at least 1,500, at least 2,000, at least 2,500, at least 3,000, at least 3,200, at least 3,500, at least 3,700, at least 3,800 or at least 3,900 contiguous nucleotides from the region of the CEP290 ORF encoding the C-Terminal domain (FIG. 1). The portion of a CEP290 ORF may include a CEP290 ORF region corresponding to nucleotides 3517-7440 of SEQ ID NO:1, which is represented by SEQ ID NO:28, or nucleotides 3517-7440 of SEQ ID NO:7, which is represented by SEQ ID NO:31. The portion of a CEP290 ORF may include a nucleotide sequence at least 85%, at least 90%, at least 95%, at least 98% or at least 99% identical to at least 1,000 contiguous nucleotides from the region of a CEP290 ORF corresponding to nucleotides 3517-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 1,000 contiguous nucleotides from SEQ ID NO:28 or SEQ ID NO:31, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 1,500 contiguous nucleotides from the region of a CEP290 ORF corresponding to nucleotides 3517-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 1,500 contiguous nucleotides from SEQ ID NO:28 or SEQ ID NO:31, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 2,000 contiguous nucleotides from the region of a CEP290 ORF corresponding to nucleotides 3517-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 2,000 contiguous nucleotides from SEQ ID NO:28 or SEQ ID NO:31, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 2,500 contiguous nucleotides from the region of a CEP290 ORF corresponding to nucleotides 3517-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 2,500 contiguous nucleotides from SEQ ID NO:28 or SEQ ID NO:31, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 3,000 contiguous nucleotides from the region of a CEP290 ORF corresponding to nucleotides 3517-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 2,700 contiguous nucleotides from SEQ ID NO:28 or SEQ ID NO:31, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 3,200 contiguous nucleotides from the region of a CEP290 ORF corresponding to nucleotides 3517-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 3,200 contiguous nucleotides from SEQ ID NO:28 or SEQ ID NO:31, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 3,500 contiguous nucleotides from the region of a CEP290 ORF corresponding to nucleotides 3517-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 3,500 contiguous nucleotides from SEQ ID NO:28 or SEQ ID NO:31, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 3,700 contiguous nucleotides from the region of a CEP290 ORF corresponding to nucleotides 3517-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 3,700 contiguous nucleotides from SEQ ID NO:28 or SEQ ID NO:31, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 3,800 contiguous nucleotides from the region of a CEP290 ORF corresponding to nucleotides 3517-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 3,800 contiguous nucleotides from SEQ ID NO:28 or SEQ ID NO:31, wherein the portion encodes a protein that is capable of increasing visual function in a patient suffering from CEP290-related LCA.

The portion of a CEP290 ORF may include a nucleotide sequence at least 85%, at least 90%, at least 95%, at least 98% or at least 99% identical to at least 3,900 contiguous nucleotides from the region of a CEP290 ORF corresponding to nucleotides 3517-7440 of SEQ ID NO:1 or SEQ ID NO:7, wherein the portion encodes a protein that is capable of increasing visual function in a patient suffering from CEP290-related LCA. The portion of a CEP290 ORF may include a nucleotide sequence at least 85%, at least 90%, at least 95%, at least 98% or at least 99% identical to at least 3,900 contiguous nucleotides from SEQ ID NO:28 or SEQ ID NO:31, wherein the portion encodes a protein that is capable of increasing visual function in a patient suffering from CEP290-related LCA.

The portion of a CEP290 ORF may include SEQ ID NO:28 or SEQ ID NO:31. The portion of a CEP290 ORF may consist of SEQ ID NO:28 or SEQ ID NO:31.

As noted above, an isolated DNA molecule of the present disclosure encodes a CEP290 protein that is capable of increasing the visual function in a patient suffering from CEP290-related LCA. The portion of a CEP290 ORF may encode a protein comprising an amino acid sequence at least 85%, at least 90%, at least 95%, at least 97% or at least 99% identical to at least 500 contiguous amino acid residues from SEQ ID NO:28 or SEQ ID NO:31, wherein the CEP290 protein is capable of increasing visual function in a patient suffering from CEP290-related LCA. The portion of a CEP290 ORF may encode a protein comprising an amino acid sequence at least 85%, at least 90%, at least 95%, at least 97% or at least 99% identical to at least 600 contiguous amino acid residues from SEQ ID NO:28 or SEQ ID NO:31, wherein the CEP290 protein is capable of increasing visual function in a patient suffering from CEP290-related LCA. The portion of a CEP290 ORF may encode a protein comprising an amino acid sequence at least 85%, at least 90%, at least 95%, at least 97% or at least 99% identical to at least 700 contiguous amino acid residues from SEQ ID NO:28 or SEQ ID NO:31. The portion of a CEP290 ORF may encode a protein comprising an amino acid sequence at least 85%, at least 90%, at least 95%, at least 97% or at least 99% identical to at least 800 contiguous amino acid residues from SEQ ID NO:28 or SEQ ID NO:31, wherein the CEP290 protein is capable of increasing visual function in a patient suffering from CEP290-related LCA. The portion of a CEP290 ORF may encode a protein comprising an amino acid sequence at least 85%, at least 90%, at least 95%, at least 97% or at least 99% identical to at least 900 contiguous amino acid residues from SEQ ID NO:28 or SEQ ID NO:31, wherein the CEP290 protein is capable of increasing visual function in a patient suffering from CEP290-related LCA. The portion of a CEP290 ORF may encode a protein comprising an amino acid sequence at least 85%, at least 90%, at least 95%, at least 97% or at least 99% identical to at least 1000 contiguous amino acid residues from SEQ ID NO:28 or SEQ ID NO:31, wherein the CEP290 protein is capable of increasing visual function in a patient suffering from CEP290-related LCA. The portion of a CEP290 ORF may encode a protein comprising an amino acid sequence at least 85%, at least 90%, at least 95%, at least 97% or at least 99% identical to at least 1,100 contiguous amino acid residues from SEQ ID NO:28 or SEQ ID NO:31, wherein the CEP290 protein is capable of increasing visual function in a patient suffering from CEP290-related LCA. The portion of a CEP290 ORF may encode a protein comprising an amino acid sequence at least 85%, at least 90%, at least 95%, at least 97% or at least 99% identical to at least 1,200 contiguous amino acid residues from SEQ ID NO:28 or SEQ ID NO:31, wherein the CEP290 protein is capable of increasing visual function in a patient suffering from CEP290-related LCA. The portion of a CEP290 ORF may encode a protein comprising an amino acid sequence at least 85%, at least 90%, at least 95%, at least 97% or at least 99% identical to at least 1,250 contiguous amino acid residues from SEQ ID NO:28 or SEQ ID NO:31, wherein the CEP290 protein is capable of increasing visual function in a patient suffering from CEP290-related LCA. The portion of a CEP290 ORF may encode a protein comprising an amino acid sequence at least 85%, at least 90%, at least 95%, at least 97% or at least 99% identical to at least 1,300 contiguous amino acid residues from SEQ ID NO:28 or SEQ ID NO:31, wherein the CEP290 protein is capable of increasing visual function in a patient suffering from CEP290-related LCA. The portion of a CEP290 ORF may encode a protein comprising an amino acid sequence at least 85%, at least 90%, at least 95%, at least 97% or at least 99% identical to SEQ ID NO:28 or SEQ ID NO:31, wherein the CEP290 protein is capable of increasing visual function in a patient suffering from CEP290-related LCA. The portion of a CEP290 ORF may encode a protein comprising SEQ ID NO:28 or SEQ ID NO:31. The portion of a CEP290 ORF may also encode a protein consisting of SEQ ID NO:28 or SEQ ID NO:31.

It is well appreciated in the art that the efficiency of delivery of nucleic acid molecules into cells can be increased using a delivery means such as a viral particle. Moreover, isolated DNA molecules of the present invention that comprise viral packaging sequences may be packaged into viral particles for use in delivering the CEP290 ORF to the eye of a patient in need of such treatment. As used herein, a viral particle refers to a particle comprising capsid proteins from one or more viruses, and which can encapsulate, or contain, isolated DNA containing the appropriate packaging sequences. Thus, one embodiment of the present invention is a virus particle comprising an isolated nucleic acid molecule of the present invention. In one embodiment, the viral particle comprises capsid proteins from an AAV. Such a particle can be referred to as an adeno-associated virus (AAV) particle. Thus, one embodiment of the present invention is an AAV particle comprising a nucleic acid molecule of the present invention. As noted previously, the AAV particle can be from any serotype of AAV as long as the virus particle is capable of delivering the isolated DNA of the present invention into a cell of the eye. In one embodiment, the virus particle is selected from the group consisting of AAV2, AAV3, AAV5, AAV6, AAV7, AAV8, AAV9 and AAV10. The general use of such particles is described in International Application No. PCT/US14/16389, the entirety of which is incorporated herein by reference.

Another aspect of this disclosure provides therapeutic compositions including isolated DNA molecules or viral particles of the present invention. Such compositions include physiologically acceptable solutions that comprise, for example, water, saline, salts, buffers, diluents, stabilizing agents, polymers, chelating agents and the like. One example of a physiologically acceptable solution is a solution comprising about 10 mM Tris-HCl (pH 7.4) and about 180 mM NaCl. It will be appreciated by those skilled in the art that such concentrations are approximate and may vary by as much as 10% or more, without significant affect on the efficacy of the composition.

One aspect of the invention provides methods of treating a patient having CEP290-related LCA. These methods include administering to the patient's eye an isolated DNA molecule of the present invention.

As used herein, the terms "patient," "individual" and "subject" are well-recognized in the art, and are used interchangeably to refer to any human or other animal in need of treatment of a disease of the eye. Examples include, but are not limited to, humans and other primates, non-human primates such as chimpanzees and other apes and monkey species; farm animals such as cattle, sheep, pigs, seals, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. A preferred patient to treat is a human patient. The terms patient, individual and subject by themselves do not denote a particular age, sex, race, and the like. Thus, individuals of any age, whether male or female, are intended to be covered by the present disclosure and include, but are not limited to the elderly, adults, children, babies, infants, and toddlers. Likewise, the methods of the present invention can be applied to any race, including, for example, Caucasian (white), African-American (black), Native American, Native Hawaiian, Hispanic, Latino, Asian, and European.

Any method that delivers an isolated DNA molecule of the present invention into the eye of the patient can be employed. For example, in one embodiment, the isolated DNA is delivered as "naked" DNA. That is, the DNA can be injected into the eye such that it is taken up by the appropriate cells of the eye. Alternatively, the DNA may first be mixed with a lipid carrier such that, following injection of the DNA:lipid complex into the eye, the DNA enters the cells of the eye by transduction. Methods of delivering DNA to cells by transduction are known to those skilled in the art.

In one or more embodiments, an isolated DNA molecule of this disclosure is administered using a viral particle of the present disclosure. Thus, one embodiment of the present invention is a method of treating a patient having CEP290-related LCA, the method including administering to the eye of a patient having CEP290-related LCA a virus particle of the present invention. As noted above, virus particles of the present invention include nucleic acid molecules comprising at least a portion of a CEP290 ORF encoding a protein capable of improving visual function in a patient to whom it is administered. Thus, administration of a viral particle of the present invention will result in expression of the encoded portion of the CEP290 protein and subsequent improvement in visual function. In one embodiment, the viral particle is an AAV particle comprising a nucleic acid molecule of the present invention. Any method of administration can be used to deliver the expression vector, so long as the expression vector is delivered to the appropriate location of the eye resulting in expression of the encoded portion of the CEP290 protein.

In one or more embodiments, a nucleic acid molecule of the present invention is encapsulated in a viral particle that is able to traverse the outer layers of the eye (i.e., cornea, iris, sclera, pupil, lens, or conjunctiva) and enter into the intraocular fluid (also referred to as the aqueous humor). Thus, an isolated DNA molecule of the invention, either alone or in an encapsulated form, may be administered topically to the eye.

An isolated DNA molecule, either alone or in an encapsulated form, may be injected into the eye. This may include subconjunctival, sub-Tenon's, intravitreal, subretinal and intracameral injections. Such injections can deliver an isolated DNA molecule or a viral particle of the present invention to the intraocular fluid or to a location within the retina. In one embodiment, the injection delivers the isolated DNA, or a viral particle of the present invention, to the intraocular fluid. In one embodiment, the injection delivers the isolated DNA, or a viral particle containing the isolated DNA, into the retina. In specific embodiments, the isolated DNA, or a viral particle of the invention, is administered by intravitreal injection. In another embodiment, the isolated DNA, or a viral particle of the present invention, is administered by subretinal injection. In another embodiment, the isolated DNA, or a viral particle of the present invention, is administered by sub-Tenon's injection. Methods of performing intraocular injections are known to those skilled in the art. In all of these methods, the isolated DNA, or a viral particle of the present invention, is preferably contained within, and administered via a polypropylene syringe.

Another aspect of this disclosure provides a method of treating CEP290-related LCA in a human including administering to a human subject diagnosed with, or suspected of having, or being at risk of developing CEP290-related LCA, a therapeutically-effective amount of a vector of the present invention, wherein administration of the vector causes expression of a human CEP290 protein fragment of the invention in a cell in the eye of the human subject, and reduces at least one symptom of LCA. The vector may be administered as naked, or encapsulated, DNA. The vector may be administered as a viral particle. The vector may be an AAV particle comprising a nucleic acid molecule of the present invention. The cell in the eye may be a photoreceptor cell. The vector may be administered using intravitreal, subretinal or subtenon injection techniques.

The vector of the invention is administered in an amount that is therapeutically effective. When administered by injection, the single injection dosage may include between $1e^{8}$ nams/eye and $3e^{13}$ nams/eye (i.e., $1\times10^{8}$ nucleic acid molecules (nams) per eye to $3\times10^{13}$ nams per eye). When administered by these means, the single injection dosage may be between $3e^{8}$ nams/eye and $1e^{13}$ nams/eye, or between $1e^{9}$ nams/eye and $1e^{13}$ nams/eye, or between $3e^{9}$ nams/eye and $1e^{13}$ nams/eye, or between $1e^{10}$ nams/eye and $1e^{13}$ nams/eye, or between $3e^{10}$ nams/eye and $1e^{13}$ nams/eye, or between nams/eye and $1e^{13}$ nams/eye, or between $3e^{11}$ nams/eye and $1e^{13}$ nams/eye, or between $1e^{12}$ nams/eye and $1e^{13}$ nams/eye, or between $3e^{12}$ nams/eye and $1e^{13}$ nams/eye.

The present invention also provides kits for practicing the disclosed methods. Kits of the present invention may include expression vectors of the present invention and viral vectors of the present invention. Such kits may also include reagents and tools necessary for practicing the disclosed methods, such as buffers, diluents, syringes, needles and instructions for administering such reagents.

While these aspects of this disclosure have been described with reference to preferred constructs, reagents and administration techniques, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims.

EXAMPLES

Example 1

Comparison of Therapeutic Effect of Different CEP290 Fragments in Rd16/Nrl KO Mice by Photopic Electroretinogram (ERG)

Figure 2A:
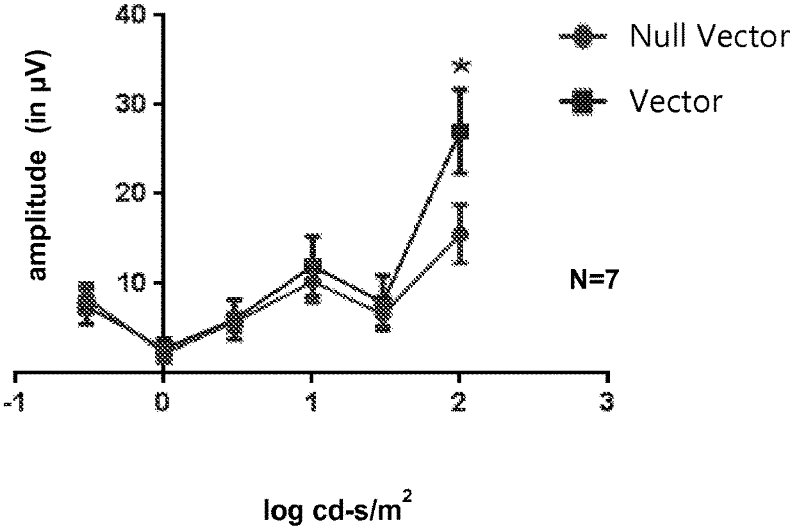
FIGS. 2*a*, 2*b*, and 2*c* show electroretinogram (ERG) data comparing the therapeutic effect of administration of the DSD, Myosin Tail, or C-terminal fragment.
Figure 2B:
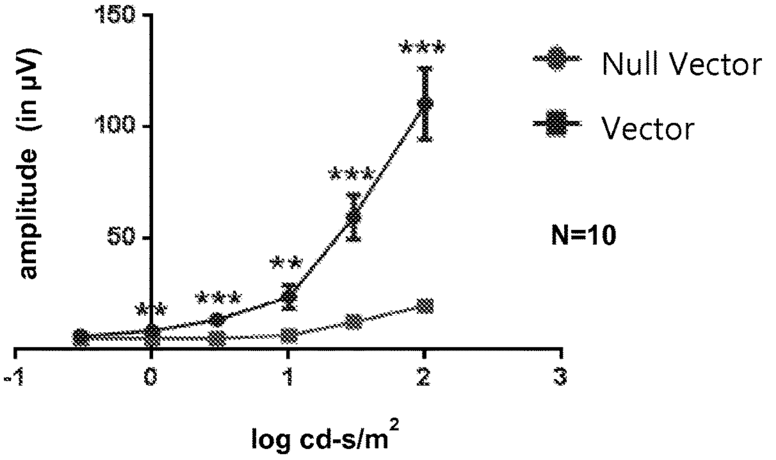
Figure 2C:
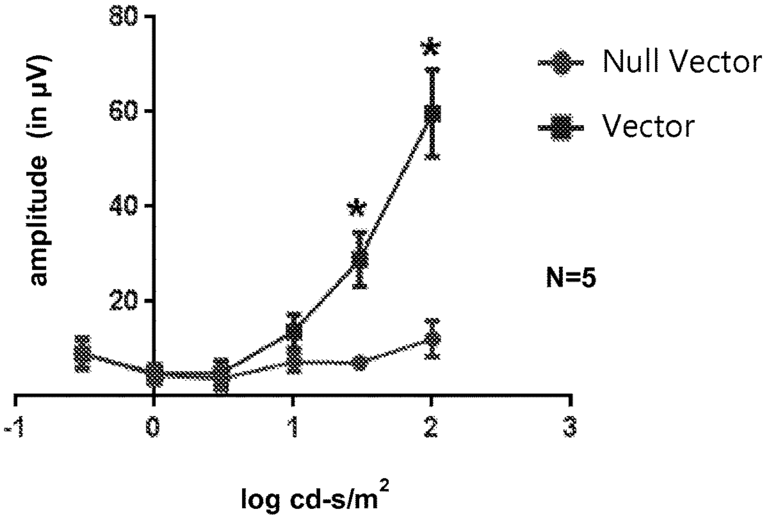

Two-week old mice were administered 8.8e8 AAV vector particles unilaterally through subretinal injection (results of administration of the DSD fragment vector are shown in FIG. 2*a*, results of administration of myosin tail fragment vector are shown in FIG. 2*b*, results of administration of c-terminal vector are shown in FIG. 2*c*). The control eyes were injected with an equal dose of viral particle with no expression cassette (null vector). The mice were followed by ERG 6 or 8 Weeks after Injection. These Data Demonstrate that the Vector Containing the Myosin-Tail CEP290 protein fragment showed the best therapeutic effect.

Example 2

The Myosin-tail Vector is Effective within a Wide-dose Range

Figure 3A:
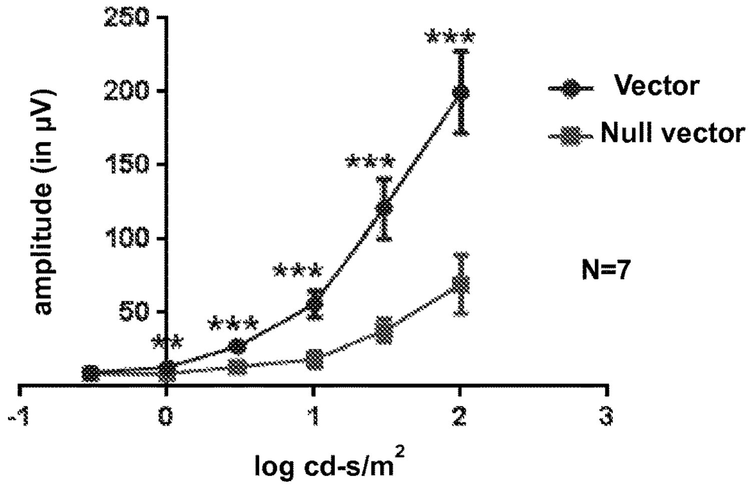
FIGS. 3*a*, 3*b*, and 3*c* show a dose-response study of the therapeutic effect of administration of the Myosin Tail fragment.
Figure 3B:
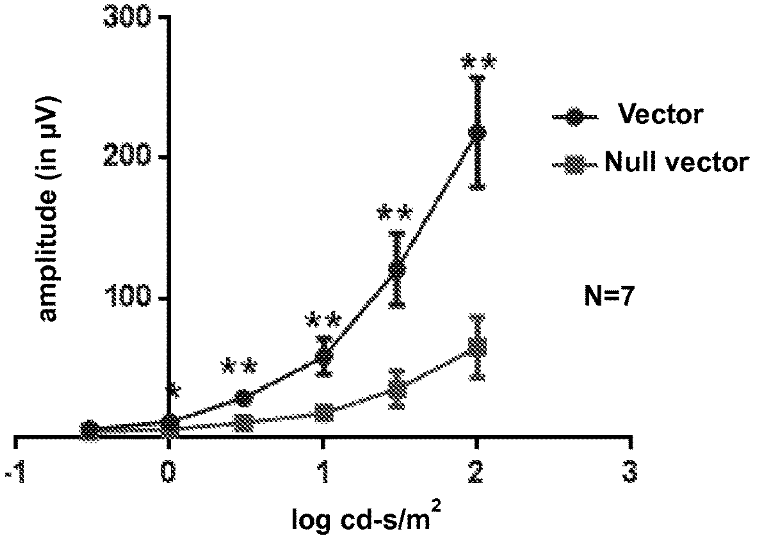
Figure 3C:
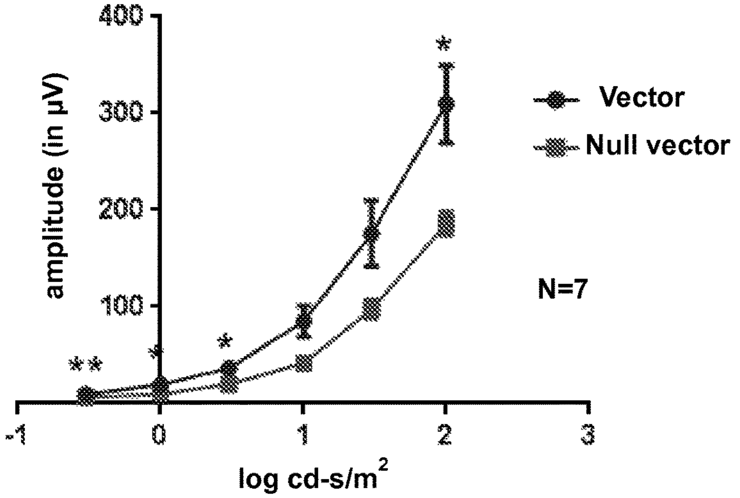

Two week old Rd16/NrlKO mice were administrated 5e8 to 2e9 vg AAV CEP290 myosin tail fragment vector unilaterally through subretinal injection (FIG. 3*a* shows 5e8 vg/eye dose; FIG. 3*b* shows 1e9 vg/eye dose; FIG. 3*c* shows 2e9 vg/eye dose). The control eyes were injected with equal dose of viral particle with no expression cassette (null vector). These mice were followed by photopic ERG 1 month after injection. These data demonstrate that the vector containing the Myosin-tail CEP290 protein fragment was effective following administration at all doses spanning 5e8 to 2e9 vg AAV vector.

Example 3

Figure 4A:
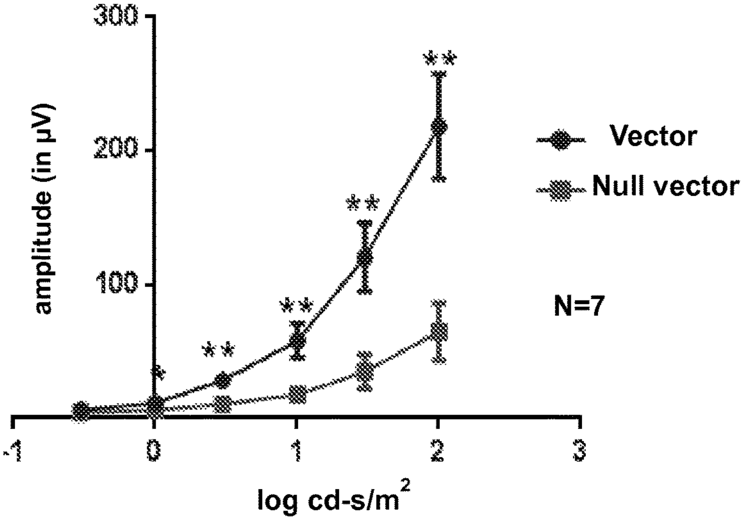
FIG. 4 shows electroretinogram (ERG) data monitoring long term effects of the therapeutic effect of administration of the Myosin Tail fragment.
Figure 4B:
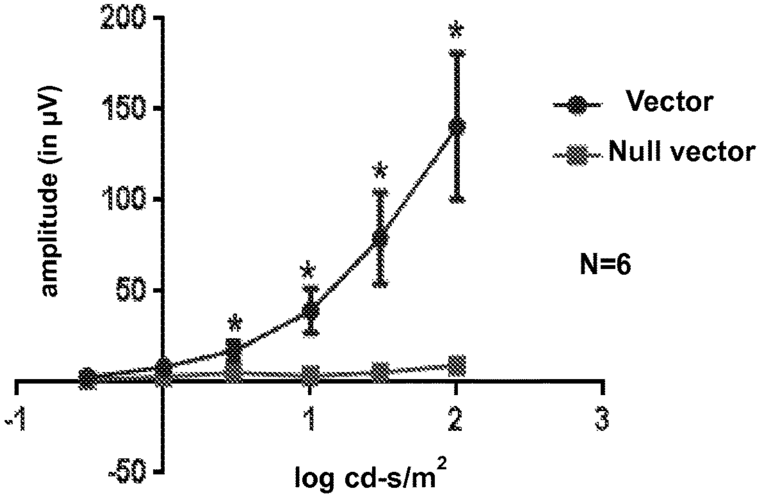
Figure 4C:
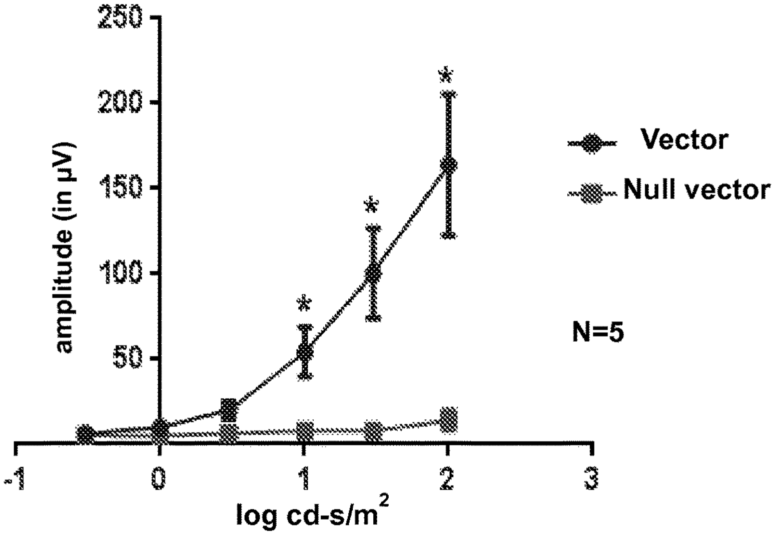

Long-term Therapeutic Effect of Administration of the Myosin-tail Fragment Vector Two week old Rd16/Nrl knockout (KO) mice were administered 1e9 vg AAV myosin tail CEP290 fragment vector unilaterally through subretinal injection. The control eyes were injected with an equal dose of viral particle with no expression cassette (null vector). These mice were followed by photopic ERG for 8 months after injection. FIG. 4*a* shows the results of vector administration one month post administration, FIG. 4*b* shows the results of vector administration at four months post administration, and FIG. 4*c* shows the results of vector administration at eight months post administration. These data demonstrate that administration of the vector containing the Myosin-tail CEP290 protein fragment was effectively expressed for many months following an initial administration.

Example 4

Figure 5:
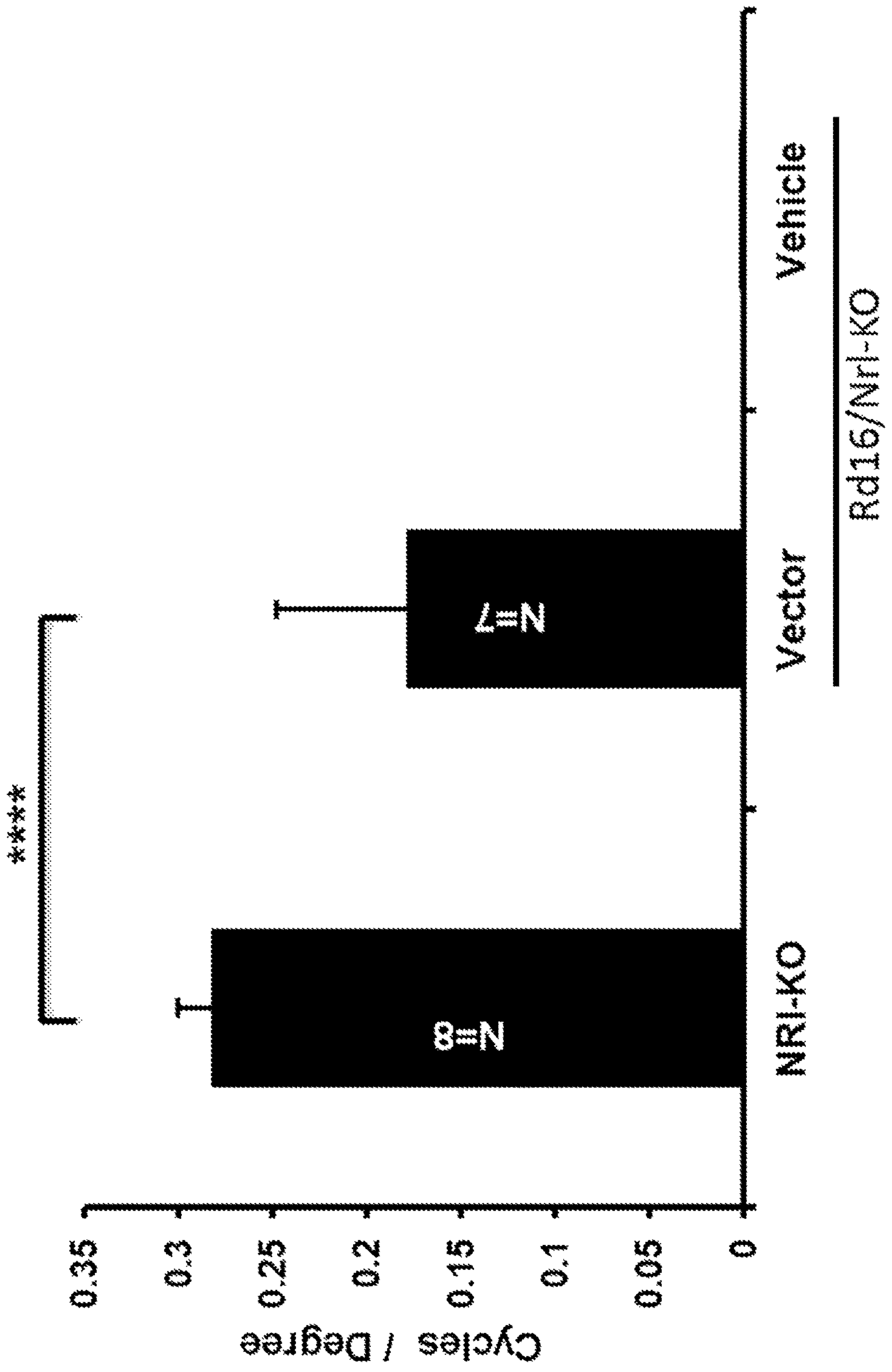
FIG. 5 shows the results of photopic optomotor testing of mice following administration of CEP290 protein fragment vector of this disclosure.

Improved Visual Behavior Following Myosin-tail CEP290 Protein Fragment Vector Treatment FIG. 5 shows the results of photopic optomoter testing of three-week old Rd16/NrlKO mice administered 8e8 vg myosin tail CEP290 fragment vector unilaterally through subretinal injection. The control eyes were injected with equal volume of vehicle. The photopic optomotor tests were administered to these mice at 3 months of age. Nrl-KO mice with all cone retina were used as positive controls. These data demonstrate the significant increase in visual function lasting at least three months in these test animals following administration of a vector encoding a CEP290 protein fragment of this disclosure.

Example 5

Figure 6:
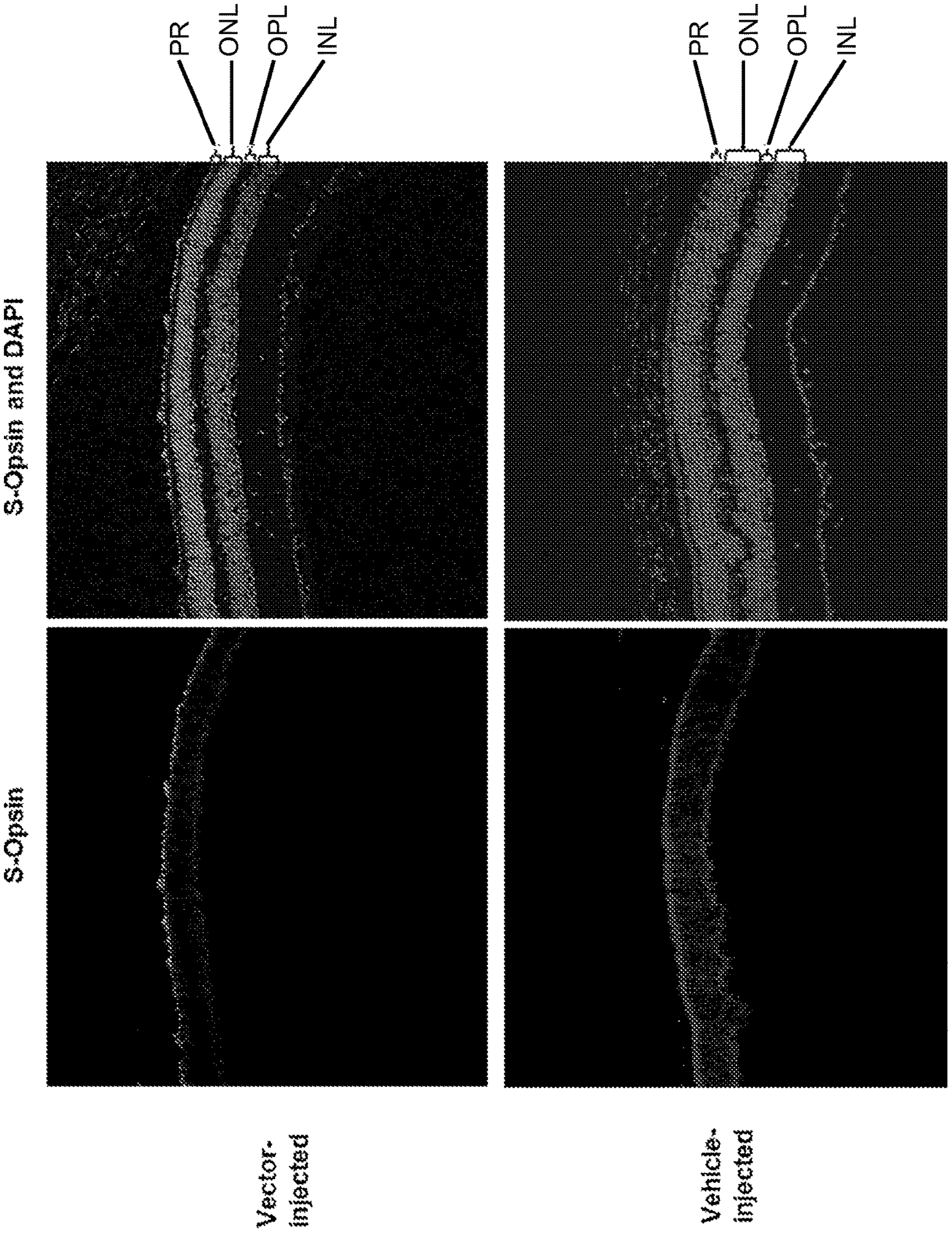
FIG. 6 shows immunohistochemistry data showing corrected s-opsin mislocalization along with higher s-opsin expression in the retina of mice treated with vector particles containing CEP290 protein fragment constructs of this disclosure.

Correction of s-opsin Mislocalization and Higher s-opsin Expression in Vector Treated Retinas Two week old RD16/NRL KO mice were administered $2\times10^9$ AAV vector particles unilaterally through subretinal injection. Control eyes were injected with vehicle. These mice were euthanized four months after injection and their eyes are analyzed by immunohistochemistry (IHC) (FIG. 6). In the vehicle-treated eyes, s-opsin was mislocalized to photoreceptor cell bodies and synaptic terminals. These data demonstrate that vector-treated eye showed corrected s-opsin localization (outer-segments) and a higher s-opsin expression. In FIG. 6, PR: photoreceptor; ONL: outer nuclear layer; OPL; Outer plexiform layer, INL: inner nuclear layer: s-opsin staining appears in PR in all four IHC images; s-opsin also appears in OPL in vehicle-injected IHC images.

What is claimed is:

1. A viral vector comprising a deoxyribonucleic acid (DNA) molecule comprising a nucleotide sequence that encodes a protein consisting of the amino acid sequence of SEQ ID NO: 11 that when expressed in photoreceptor cells of a patient suffering from CEP290-related Leber congenital amaurosis (LCA), increases visual function of the patient.

2. The viral vector of claim 1, wherein the nucleotide sequence that encodes at least a portion of a CEP290 ORF consists of the nucleotide sequence of SEQ ID NO:10.

3. The viral vector of claim 1, wherein the vector is an adeno-associated virus (AAV) vector.

4. The vector of claim 3, wherein the AAV is an AAV8 vector.

5. The viral vector of claim 1, further comprising a promoter sequence functionally linked to the CEP290 ORF to cause expression of the ORF, selected from the group consisting of a rhodopsin promoter, a rhodopsin kinase promoter, an Interstitial retinol-binding protein (IRBP promoter), a cytomegalovirus (CMV) promoter, and a CMV intermediate-early (IE) promoter.

6. The viral vector of claim 1, further comprising at least one inverted terminal repeat (ITR) nucleotide sequence that comprises an AAV Rep binding site (RBS) and a terminal resolution site (trs) sequence.

7. The viral vector of claim 6, wherein the at least one ITR comprises an ITR from an AAV2 virus.

* * * * *

SEQUENCE LISTING

```
<160> NUMBER OF SEQ ID NOS: 45

<210> SEQ ID NO 1
<211> LENGTH: 7440
<212> TYPE: DNA
<213> ORGANISM: Mus musculus

<400> SEQUENCE: 1

atgccaccta atataaagtg gaaagaatta atcaaagttg atccagatga cctgccacgg     60

caagaagagt tagcagataa attattgata tctttatcca aggtggaagt aaatgaacta    120

aaaaatgaag accaagaaaa catgatacat ctattcagaa ttacccagtc tctaatgaag    180

atgaaagccc aggaagtaga gctcgctttg gaagaagttg aaaaggctgg agaagaacaa    240

gcaaaatttg aaaatcaatt aaagacaaaa gtaatgaaac tggaaaatga actggagatg    300

gctcagcagt ctgcaggggg acgtgacact cggtttttac gtgacgaaat tcgccaactt    360

gagaagcagc tggaacaaaa agatagagaa ttagaggata tggaaaaaga attggataaa    420

gaaaagaagg ttaatgaaca attggctctt cgaaatgagg aggcagaaaa tgaaaacagc    480

aaattaagaa gagagaacaa acgtctaaag aaaaagaatg agcagcttcg gcaggacatt    540

attgactacc agaaacaaat agattcacag aaagaatcac ttctgtcaag gagaggagaa    600

gacagtgact accgatcaca gttgtctaaa aagaactatg aacttgttca atatctggac    660

gaaatacaga ccttaacaga agctaatgag aagattgaag ttcagaacca agaaatgagg    720

aaaaacctgg aagagtctgt gcaggagatg gagaagatga ctgatgagta caacaggatg    780

aaagcgcttg tgcatcagtc ggatgctgtc atggaccaga tcaagaagga gaatgagcac    840

tatcgcctgc aagttcgaga gctcacggat cttctgaagg cgaaggatga agaggacgat    900

ccagtcatga tggctgttaa cgcaaaagtg gaagagtgga agttaatttt gtcttctaaa    960

gatgatgaaa tcattgaata tcagcaaatg ctacagagtc tgagagggaa acttaaaaat   1020

gcccaacttg atgcagacaa aagtaacatc atggctctga aacagggtat ccaggagcga   1080

gacagtcaaa ttaagatgct tactgagcaa gtagaacagt atacgaaaga aatggaaaaa   1140

aatacgttta ttattgaaga tttgaaaaat gaactccaaa aagacaaagg tacttcaaac   1200
```

-continued

```
ttttatcagc agactcatta tatgaaaatt cactcaaaag tacaaatttt agaagagaaa   1260
acaaaagagg ccgagagaat agctgagctg gctgaggctg atgccaggga gaaggacaaa   1320
gaattggttg aggctctgaa gagattaaaa gattatgaat ctggagtata tggcttagaa   1380
gatgctgtta tcgaaataaa gaattgtaaa gcccaaatta aaataagaga tggagagatg   1440
gaagtgttga ccaaggagat caataagctt gagatgaaga tcaatgacat ccttgatgaa   1500
aacgaagccc ttagagagcg ggctggcctt gaacccaaga caatgattga tttgactgaa   1560
tttagaaaca gcaaacggtt aaagcagcaa cagtacagag ctgagaacca ggttcttttg   1620
aaagagatcg aaagtctaga ggaggagcgt cttgacttga aaagaaagat tcgtcaaatg   1680
gctcaagaaa gaggcaaaag gaacgcagcc tcaggattaa ccattgacga cttgaactta   1740
tctgaaacct tttctcatga aaataaaata gaaggaagaa aactaaattt tatgagcctc   1800
aataatatga atgaaacaca atcaaagaat gagtttcttt caagagaatt ggctgaaaag   1860
gaaaaagatt tagaaagaag taggacagta attgctaaat tccagagtaa actaaaagaa   1920
ttagtcgaag aaaataagca acttgaagaa ggtatgaaag aaattttgca agctattaag   1980
gacatgccga aggattctga tgtgaaagga ggtgaaacat ctttaatcat cccgagtctt   2040
gaaagactgg ttaacgctat ggaatcaaag aatgcagaag gaatcttcga tgccagcttg   2100
catctaaaag cccaagttga ccaacttaca ggaaggaatg aagaattaag gcaagaactc   2160
aggcaatctc ggaaagaggc tgtaaattat tcacagcagt tggtaaaagc aaacttaaag   2220
attgaccacc ttgagaagga aactgacctt ctacgtcagt ctgcaggctc caatgtagta   2280
tacaaaggca tagacttacc cgatgggata gcaccatcca gtgcctatat catcaattct   2340
cagaatgaat acttaataca tcttttgcag gaactagaca ataaagaaaa gaaattaaaa   2400
catttagaag attcccttga agattataac agaaagtttg cagtgattcg tcatcaacaa   2460
agtttattat ataaagaata cctaagtgaa aaggatattt ggaaaacaga ctctgagatg   2520
ataagagagg agaagagaaa actggaagat caagctgagc aggatgctgt gaaagtaaaa   2580
gagtacaaca atttgctcag tgctcttcag atggattcga acgagatgaa gaaaatgctc   2640
tcagaaaaca gtaggaaaat caccgttctg caagtgaacg agaagtccct catccggcag   2700
tacaccacct tagtggagat ggagcggcac ctgagaaagg aaaacgggaa acacaggaat   2760
gacgtcatag ccatggaggc cgaagtcact gaaaaacttg gaagtttgca aagattcaag   2820
gaaatggcca tcttcaagat tgcagctctt cagaaggtta tagataatag tgtttctttg   2880
tctgaattag aactagccaa taaacagtac aatgagctga ctactaagta cagggacatc   2940
ttgcagaaag ataatatgct tgttcaaaga acaagtaact tagaacacct ggagtgtgag   3000
aatgcatcgc taaaagaaca gatggaggct atcagtaaag agctggagat tacaaaggaa   3060
aaactccata ccattgaaca ggcctgggaa caagaaacga agttaggaaa tgactcaaac   3120
atggataagg ctaagaaatc aatgacaaac agtgacattg tttctatttc aaagaaaatc   3180
actgtgttgg agatgaagga attaaatgaa aggcagaggg ctgaacactg tcagaaaatg   3240
tatgagcact taaggacttc attaaagcaa atggaagaac gtaattttga attggaaacc   3300
aagttcactg agcttactaa aatcaacctg gatgcacaaa aggtggagca gatgttgaga   3360
gacgaattag ctgatagtgt gaccaaggca gtaagtgatg ctgaccgaca gcggattcta   3420
gaactagaga agagtgaagt ggagctcaaa gttgaagtgt ccaagctgag agagatttca   3480
gatattgcca aaagacaagt tgattttttg aattcgcaac aacagtccag ggaaaaggaa   3540
gtggaatccc tcagaacgca gctgctggac ttccaggcac aatctgacga aaaggctcta   3600
```

```
attgccaaat tgcaccaaca tgttgtctct cttcaaatta gtgaggccac tgccctcggt   3660
aagttagagt cagttacgtc caaactccag aagatggaag cctacaattt gcgcttagaa   3720
cagaaactgg atgaaaaaga gcaggcgctc tactatgctc gtttggaagg tagaaacaga   3780
gcaaaacacc tgcgccaaac cattcagtcg cttcgaagac agttcagtgg agctctaccc   3840
ttagcacagc aggaaaagtt ctccaaaacg atgattcagt tgcaaaatga caaacttaag   3900
ataatgcaag aaatgaagaa ttcgcaacag gaacacagaa atatggaaaa caaaacactg   3960
gagttggaat taaaattaaa aggcttagaa gaattgatca gtactttaaa ggatgccagg   4020
ggagcccaga aggtaatcaa ttggcatgtg aaaatagaag aacttcgcct ccaagaactt   4080
aagctaaata gagaactagt caagggtaaa gaagaaatca aatatttgaa taatatcatc   4140
tctgaatatg agcatacaat caacagtcta gaggaagaaa ttgttcagca aagcaagttc   4200
catgaagaaa gacagatggc ttgggatcaa agagaagttg agctggaacg ccagttagac   4260
atttttgatc atcagcaaaa tgaaatactc agtgcagcac aaaagtttga agactctaca   4320
ggatcaatgc cagaccccag cttgcctctt ccaaaccaac ttgaaattgc tctaagaaaa   4380
attaaggaga atattcaagt aattcttaaa acacaagcaa cttgcaagtc actagaagag   4440
aaactaaaag aaaaagaatc tgctttacgg ttggcagagc aaaatattct gtcaagagac   4500
aaagtaatca atgaactgag gcttcgattg cctgccacgg ctgatcgaga aaaacttata   4560
gctgagctag aaagaaaaga gctggagccg aaatctcatc acacaatgaa aattgcccac   4620
caaactattg ccaacatgca ggcaaggtta aatcacaagg aagaagtatt gaagaaatac   4680
cagcaccttc tggagaaggc cagagaggag caaagagaaa ttgttaagaa gcatgaggaa   4740
gaccttcatg ttcttcatca caaattagaa caacaggccg ataattcact caataaattc   4800
agacagacag ctcaggattt acttaagcag tctcctgctc cagttcccac caacaaacat   4860
ttcattcgtc tggccgagat ggagcagaca gtagcagaac aagatgactc tctgtcctca   4920
cttttgacca aactaaagaa agtatcaaaa gatttggaaa aacaaaaaga aatcactgag   4980
ttaaaagtca gagagtttga aaataccaaa ctacggctcc aagaaactca tgccagtgag   5040
gtaaagaaag tgaaagcaga ggtagaggac ttaaggcatg ctctagccca agcacacaag   5100
gactcccaga gtttaaagtc tgaactccag gctcagaaag aagcaaactc cagagctcca   5160
acaaccacaa tgaggaatct tgtagacagg ctaaagagcc aactagcctt gaaagagaag   5220
caacaaaagg cacttagtcg agccctgttg gaacttcggt cggaaatgac agcagcagct   5280
gaggaacgta taatcgctgt aacttctcaa aaagaggcaa atctcaatgt tcaacaagtt   5340
gttgagcgcc atactagaga gctaaagtca caaattgaag atttaaatga aaatctttta   5400
aaattgaaag aagctcttaa aacaagtaag aacaaagaaa attcactagc tgatgattta   5460
aatgaattaa ataatgaact gcaaaaaaag caaaaagctt ataataaaat ccttagagag   5520
aaagatggaa ttgatcaaga aaatgatgaa ctgagaagac agattaaaag actgtccagt   5580
ggactgcaga gcaaaacttt gatagataac aagcaaagtt taatcgatga acttcaaaag   5640
aaagttaaaa aacttgaaag ccaactggaa agaaaggtgg atgacgtaga cataaagccg   5700
gtgaaggaaa agagtagtaa agaagaatta attaggtggg aagaaggtaa gaaatggcaa   5760
accaaagtag agggactacg aaacagacta aaggagaagg aaggagaagc ccacggcctg   5820
gcaaagcagc tgaatacctt aaaggaactt tttgccaaag ctgataaaga gaaacttact   5880
ttgcagaaga aactgaaaac aacaggaatg actgttgacc aggttttagg agtgcgagct   5940
```

-continued ttggaatctg aaaaagagtt ggaagagcta aaaaagaaaa atctggacct agaaaatgac 6000
atattataca tgaggaccca gcaggctctt ccacgagatt ctgttgtgga agacttacat 6060
ttacaaaata aataccttca agaaaaactt catactttag aaaaaaaact ttcaaaggag 6120
aaatattctc agtctttgac ttcagaaata gagtcagatg atcactgtca aaaagaacaa 6180
gaacttcaga aggaaaattt gaagttgtca tctgaaaaca tcgagctgaa atttcaactt 6240
gaacaagcaa ataaagattt gccaagacta aagaatcaag tgaaagattt gaaggaaatg 6300
tgtgaatttc ttaagaaagg aaaactggaa cttgagcgga agcttggtca ggtcagaggg 6360
gctggtagaa gtgggaagac aatcccagaa ctagaaaaaa ccattgggtt aatgaagaaa 6420
gtagttgaaa aagtccaaag agaaaatgaa caattgaaaa aggcatcagg aatactgact 6480
agtgaaaaaa tggctactat tgaggaagaa aatagaaact taaaggctga actagaaaag 6540
cttaaagctc actttggacg tcagttgagt atgcagtttg aatctaagaa caaaggtact 6600
gagaaaattg ttgccgaaaa tgaacggctt cggaaagaac ttaagaaaga aatagaagcc 6660
tctgagaaac tgcggatagc taagaacaac ttagagctgg tgaacgacaa gatggcagct 6720
caactcgaag aaactgggaa gagactacag tttgcagaaa gtagagcccc acagctggaa 6780
ggtgctgaca gcaagagctg gaagtcaatt gtggtctcaa gagtgtatga gaccaagatg 6840
aaagagcttg aaagtgacat tgccaaaaag aatcaaagta tcactgacct taaacagctt 6900
gtaagagaag caacagagag agaacagaaa gctaagaaat acactgaaga ccttgaacaa 6960
cagattgaga tcctcaaaaa tgttcctgaa ggtgccgaga cagagcaaga gcttatacgg 7020
gaactccagc ttcttagatt agccaataat cagatggata aagaaagggc agaattaatc 7080
catcagatag aaattaacaa ggaccaaacc agagctgaca gtagcatacc tgattctgat 7140
caactaaagg aaaagataaa tgacctggag acacaactca gaaagttgga gctagaaaag 7200
caacattcga aggaggaagt taaaaagctg aaaaaagaac tggaaaattt tgatccttca 7260
ttttttgaag aaattgaaga cctgaagtat aattataagg aagaagtgaa aaagaatatc 7320
ctattagaag agaagctaaa aaaactgtcg gaacagtttg gatttgaact gcctagtcct 7380
cttgctgctt ctgaacactc ggaagatgga gaaagtcctc atagtttccc tatttattag 7440

<210> SEQ ID NO 2
<211> LENGTH: 2479
<212> TYPE: PRT
<213> ORGANISM: Mus musculus

<400> SEQUENCE: 2

Met Pro Pro Asn Ile Lys Trp Lys Glu Leu Ile Lys Val Asp Pro Asp
1 5 10 15

Asp Leu Pro Arg Gln Glu Glu Leu Ala Asp Lys Leu Leu Ile Ser Leu
20 25 30

Ser Lys Val Glu Val Asn Glu Leu Lys Asn Glu Asp Gln Glu Asn Met
35 40 45

Ile His Leu Phe Arg Ile Thr Gln Ser Leu Met Lys Met Lys Ala Gln
50 55 60

Glu Val Glu Leu Ala Leu Glu Glu Val Glu Lys Ala Gly Glu Glu Gln
65 70 75 80

Ala Lys Phe Glu Asn Gln Leu Lys Thr Lys Val Met Lys Leu Glu Asn
85 90 95

Glu Leu Glu Met Ala Gln Gln Ser Ala Gly Gly Arg Asp Thr Arg Phe
100 105 110

-continued

```
Leu Arg Asp Glu Ile Arg Gln Leu Glu Lys Gln Leu Glu Gln Lys Asp
        115                 120                 125

Arg Glu Leu Glu Asp Met Glu Lys Glu Leu Asp Lys Glu Lys Lys Val
    130                 135                 140

Asn Glu Gln Leu Ala Leu Arg Asn Glu Glu Ala Glu Asn Glu Asn Ser
145                 150                 155                 160

Lys Leu Arg Arg Glu Asn Lys Arg Leu Lys Lys Lys Asn Glu Gln Leu
                165                 170                 175

Arg Gln Asp Ile Ile Asp Tyr Gln Lys Gln Ile Asp Ser Gln Lys Glu
            180                 185                 190

Ser Leu Leu Ser Arg Arg Gly Glu Asp Ser Asp Tyr Arg Ser Gln Leu
        195                 200                 205

Ser Lys Lys Asn Tyr Glu Leu Val Gln Tyr Leu Asp Glu Ile Gln Thr
    210                 215                 220

Leu Thr Glu Ala Asn Glu Lys Ile Glu Val Gln Asn Gln Glu Met Arg
225                 230                 235                 240

Lys Asn Leu Glu Glu Ser Val Gln Glu Met Glu Lys Met Thr Asp Glu
                245                 250                 255

Tyr Asn Arg Met Lys Ala Leu Val His Gln Ser Asp Ala Val Met Asp
            260                 265                 270

Gln Ile Lys Lys Glu Asn Glu His Tyr Arg Leu Gln Val Arg Glu Leu
        275                 280                 285

Thr Asp Leu Leu Lys Ala Lys Asp Glu Glu Asp Asp Pro Val Met Met
    290                 295                 300

Ala Val Asn Ala Lys Val Glu Glu Trp Lys Leu Ile Leu Ser Ser Lys
305                 310                 315                 320

Asp Asp Glu Ile Ile Glu Tyr Gln Gln Met Leu Gln Ser Leu Arg Gly
                325                 330                 335

Lys Leu Lys Asn Ala Gln Leu Asp Ala Asp Lys Ser Asn Ile Met Ala
            340                 345                 350

Leu Lys Gln Gly Ile Gln Glu Arg Asp Ser Gln Ile Lys Met Leu Thr
        355                 360                 365

Glu Gln Val Glu Gln Tyr Thr Lys Glu Met Glu Lys Asn Thr Phe Ile
    370                 375                 380

Ile Glu Asp Leu Lys Asn Glu Leu Gln Lys Asp Lys Gly Thr Ser Asn
385                 390                 395                 400

Phe Tyr Gln Gln Thr His Tyr Met Lys Ile His Ser Lys Val Gln Ile
                405                 410                 415

Leu Glu Glu Lys Thr Lys Glu Ala Glu Arg Ile Ala Glu Leu Ala Glu
            420                 425                 430

Ala Asp Ala Arg Glu Lys Asp Lys Glu Leu Val Glu Ala Leu Lys Arg
        435                 440                 445

Leu Lys Asp Tyr Glu Ser Gly Val Tyr Gly Leu Glu Asp Ala Val Ile
    450                 455                 460

Glu Ile Lys Asn Cys Lys Ala Gln Ile Lys Ile Arg Asp Gly Glu Met
465                 470                 475                 480

Glu Val Leu Thr Lys Glu Ile Asn Lys Leu Glu Met Lys Ile Asn Asp
                485                 490                 495

Ile Leu Asp Glu Asn Glu Ala Leu Arg Glu Arg Ala Gly Leu Glu Pro
            500                 505                 510

Lys Thr Met Ile Asp Leu Thr Glu Phe Arg Asn Ser Lys Arg Leu Lys
        515                 520                 525

Gln Gln Gln Tyr Arg Ala Glu Asn Gln Val Leu Leu Lys Glu Ile Glu
```

```
    530                 535                 540

Ser Leu Glu Glu Glu Arg Leu Asp Leu Lys Arg Lys Ile Arg Gln Met
545                 550                 555                 560

Ala Gln Glu Arg Gly Lys Arg Asn Ala Ala Ser Gly Leu Thr Ile Asp
                565                 570                 575

Asp Leu Asn Leu Ser Glu Thr Phe Ser His Glu Asn Lys Ile Glu Gly
            580                 585                 590

Arg Lys Leu Asn Phe Met Ser Leu Asn Asn Met Asn Glu Thr Gln Ser
        595                 600                 605

Lys Asn Glu Phe Leu Ser Arg Glu Leu Ala Glu Lys Glu Lys Asp Leu
    610                 615                 620

Glu Arg Ser Arg Thr Val Ile Ala Lys Phe Gln Ser Lys Leu Lys Glu
625                 630                 635                 640

Leu Val Glu Glu Asn Lys Gln Leu Glu Glu Gly Met Lys Glu Ile Leu
                645                 650                 655

Gln Ala Ile Lys Asp Met Pro Lys Asp Ser Asp Val Lys Gly Gly Glu
            660                 665                 670

Thr Ser Leu Ile Ile Pro Ser Leu Glu Arg Leu Val Asn Ala Met Glu
        675                 680                 685

Ser Lys Asn Ala Glu Gly Ile Phe Asp Ala Ser Leu His Leu Lys Ala
    690                 695                 700

Gln Val Asp Gln Leu Thr Gly Arg Asn Glu Glu Leu Arg Gln Glu Leu
705                 710                 715                 720

Arg Gln Ser Arg Lys Glu Ala Val Asn Tyr Ser Gln Gln Leu Val Lys
                725                 730                 735

Ala Asn Leu Lys Ile Asp His Leu Glu Lys Glu Thr Asp Leu Leu Arg
            740                 745                 750

Gln Ser Ala Gly Ser Asn Val Val Tyr Lys Gly Ile Asp Leu Pro Asp
        755                 760                 765

Gly Ile Ala Pro Ser Ser Ala Tyr Ile Ile Asn Ser Gln Asn Glu Tyr
    770                 775                 780

Leu Ile His Leu Leu Gln Glu Leu Asp Asn Lys Glu Lys Lys Leu Lys
785                 790                 795                 800

His Leu Glu Asp Ser Leu Glu Asp Tyr Asn Arg Lys Phe Ala Val Ile
                805                 810                 815

Arg His Gln Gln Ser Leu Leu Tyr Lys Glu Tyr Leu Ser Glu Lys Asp
            820                 825                 830

Ile Trp Lys Thr Asp Ser Glu Met Ile Arg Glu Glu Lys Arg Lys Leu
        835                 840                 845

Glu Asp Gln Ala Glu Gln Asp Ala Val Lys Val Lys Glu Tyr Asn Asn
    850                 855                 860

Leu Leu Ser Ala Leu Gln Met Asp Ser Asn Glu Met Lys Lys Met Leu
865                 870                 875                 880

Ser Glu Asn Ser Arg Lys Ile Thr Val Leu Gln Val Asn Glu Lys Ser
                885                 890                 895

Leu Ile Arg Gln Tyr Thr Thr Leu Val Glu Met Glu Arg His Leu Arg
            900                 905                 910

Lys Glu Asn Gly Lys His Arg Asn Asp Val Ile Ala Met Glu Ala Glu
        915                 920                 925

Val Thr Glu Lys Leu Gly Ser Leu Gln Arg Phe Lys Glu Met Ala Ile
    930                 935                 940

Phe Lys Ile Ala Ala Leu Gln Lys Val Ile Asp Asn Ser Val Ser Leu
945                 950                 955                 960
```

-continued

```
Ser Glu Leu Glu Leu Ala Asn Lys Gln Tyr Asn Glu Leu Thr Thr Lys
                965                 970                 975

Tyr Arg Asp Ile Leu Gln Lys Asp Asn Met Leu Val Gln Arg Thr Ser
            980                 985                 990

Asn Leu Glu His Leu Glu Cys Glu  Asn Ala Ser Leu Lys  Glu Gln Met
        995                 1000                 1005

Glu Ala  Ile Ser Lys Glu Leu  Glu Ile Thr Lys Glu  Lys Leu His
    1010                 1015                 1020

Thr Ile  Glu Gln Ala Trp Glu  Gln Glu Thr Lys Leu  Gly Asn Asp
    1025                 1030                 1035

Ser Asn  Met Asp Lys Ala Lys  Lys Ser Met Thr Asn  Ser Asp Ile
    1040                 1045                 1050

Val Ser  Ile Ser Lys Lys Ile  Thr Val Leu Glu Met  Lys Glu Leu
    1055                 1060                 1065

Asn Glu  Arg Gln Arg Ala Glu  His Cys Gln Lys Met  Tyr Glu His
    1070                 1075                 1080

Leu Arg  Thr Ser Leu Lys Gln  Met Glu Glu Arg Asn  Phe Glu Leu
    1085                 1090                 1095

Glu Thr  Lys Phe Thr Glu Leu  Thr Lys Ile Asn Leu  Asp Ala Gln
    1100                 1105                 1110

Lys Val  Glu Gln Met Leu Arg  Asp Glu Leu Ala Asp  Ser Val Thr
    1115                 1120                 1125

Lys Ala  Val Ser Asp Ala Asp  Arg Gln Arg Ile Leu  Glu Leu Glu
    1130                 1135                 1140

Lys Ser  Glu Val Glu Leu Lys  Val Glu Val Ser Lys  Leu Arg Glu
    1145                 1150                 1155

Ile Ser  Asp Ile Ala Lys Arg  Gln Val Asp Phe Leu  Asn Ser Gln
    1160                 1165                 1170

Gln Gln  Ser Arg Glu Lys Glu  Val Glu Ser Leu Arg  Thr Gln Leu
    1175                 1180                 1185

Leu Asp  Phe Gln Ala Gln Ser  Asp Glu Lys Ala Leu  Ile Ala Lys
    1190                 1195                 1200

Leu His  Gln His Val Val Ser  Leu Gln Ile Ser Glu  Ala Thr Ala
    1205                 1210                 1215

Leu Gly  Lys Leu Glu Ser Val  Thr Ser Lys Leu Gln  Lys Met Glu
    1220                 1225                 1230

Ala Tyr  Asn Leu Arg Leu Glu  Gln Lys Leu Asp Glu  Lys Glu Gln
    1235                 1240                 1245

Ala Leu  Tyr Tyr Ala Arg Leu  Glu Gly Arg Asn Arg  Ala Lys His
    1250                 1255                 1260

Leu Arg  Gln Thr Ile Gln Ser  Leu Arg Arg Gln Phe  Ser Gly Ala
    1265                 1270                 1275

Leu Pro  Leu Ala Gln Gln Glu  Lys Phe Ser Lys Thr  Met Ile Gln
    1280                 1285                 1290

Leu Gln  Asn Asp Lys Leu Lys  Ile Met Gln Glu Met  Lys Asn Ser
    1295                 1300                 1305

Gln Gln  Glu His Arg Asn Met  Glu Asn Lys Thr Leu  Glu Leu Glu
    1310                 1315                 1320

Leu Lys  Leu Lys Gly Leu Glu  Glu Leu Ile Ser Thr  Leu Lys Asp
    1325                 1330                 1335

Ala Arg  Gly Ala Gln Lys Val  Ile Asn Trp His Val  Lys Ile Glu
    1340                 1345                 1350
```

-continued

```
Glu Leu  Arg Leu Gln Glu Leu  Lys Leu Asn Arg Glu  Leu Val Lys
    1355                 1360                 1365

Gly Lys  Glu Glu Ile Lys Tyr  Leu Asn Asn Ile Ile  Ser Glu Tyr
    1370                 1375                 1380

Glu His  Thr Ile Asn Ser Leu  Glu Glu Glu Ile Val  Gln Gln Ser
    1385                 1390                 1395

Lys Phe  His Glu Glu Arg Gln  Met Ala Trp Asp Gln  Arg Glu Val
    1400                 1405                 1410

Glu Leu  Glu Arg Gln Leu Asp  Ile Phe Asp His Gln  Gln Asn Glu
    1415                 1420                 1425

Ile Leu  Ser Ala Ala Gln Lys  Phe Glu Asp Ser Thr  Gly Ser Met
    1430                 1435                 1440

Pro Asp  Pro Ser Leu Pro Leu  Pro Asn Gln Leu Glu  Ile Ala Leu
    1445                 1450                 1455

Arg Lys  Ile Lys Glu Asn Ile  Gln Val Ile Leu Lys  Thr Gln Ala
    1460                 1465                 1470

Thr Cys  Lys Ser Leu Glu Glu  Lys Leu Lys Glu Lys  Glu Ser Ala
    1475                 1480                 1485

Leu Arg  Leu Ala Glu Gln Asn  Ile Leu Ser Arg Asp  Lys Val Ile
    1490                 1495                 1500

Asn Glu  Leu Arg Leu Arg Leu  Pro Ala Thr Ala Asp  Arg Glu Lys
    1505                 1510                 1515

Leu Ile  Ala Glu Leu Glu Arg  Lys Glu Leu Glu Pro  Lys Ser His
    1520                 1525                 1530

His Thr  Met Lys Ile Ala His  Gln Thr Ile Ala Asn  Met Gln Ala
    1535                 1540                 1545

Arg Leu  Asn His Lys Glu Glu  Val Leu Lys Lys Tyr  Gln His Leu
    1550                 1555                 1560

Leu Glu  Lys Ala Arg Glu Glu  Gln Arg Glu Ile Val  Lys Lys His
    1565                 1570                 1575

Glu Glu  Asp Leu His Val Leu  His His Lys Leu Glu  Gln Gln Ala
    1580                 1585                 1590

Asp Asn  Ser Leu Asn Lys Phe  Arg Gln Thr Ala Gln  Asp Leu Leu
    1595                 1600                 1605

Lys Gln  Ser Pro Ala Pro Val  Pro Thr Asn Lys His  Phe Ile Arg
    1610                 1615                 1620

Leu Ala  Glu Met Glu Gln Thr  Val Ala Glu Gln Asp  Asp Ser Leu
    1625                 1630                 1635

Ser Ser  Leu Leu Thr Lys Leu  Lys Lys Val Ser Lys  Asp Leu Glu
    1640                 1645                 1650

Lys Gln  Lys Glu Ile Thr Glu  Leu Lys Val Arg Glu  Phe Glu Asn
    1655                 1660                 1665

Thr Lys  Leu Arg Leu Gln Glu  Thr His Ala Ser Glu  Val Lys Lys
    1670                 1675                 1680

Val Lys  Ala Glu Val Glu Asp  Leu Arg His Ala Leu  Ala Gln Ala
    1685                 1690                 1695

His Lys  Asp Ser Gln Ser Leu  Lys Ser Glu Leu Gln  Ala Gln Lys
    1700                 1705                 1710

Glu Ala  Asn Ser Arg Ala Pro  Thr Thr Thr Met Arg  Asn Leu Val
    1715                 1720                 1725

Asp Arg  Leu Lys Ser Gln Leu  Ala Leu Lys Glu Lys  Gln Gln Lys
    1730                 1735                 1740

Ala Leu  Ser Arg Ala Leu Leu  Glu Leu Arg Ser Glu  Met Thr Ala
```

-continued

```
    1745                1750                1755

Ala Ala  Glu Glu Arg Ile Ile  Ala Val Thr Ser Gln  Lys Glu Ala
    1760                1765                1770

Asn Leu  Asn Val Gln Gln Val  Val Glu Arg His Thr  Arg Glu Leu
    1775                1780                1785

Lys Ser  Gln Ile Glu Asp Leu  Asn Glu Asn Leu Leu  Lys Leu Lys
    1790                1795                1800

Glu Ala  Leu Lys Thr Ser Lys  Asn Lys Glu Asn Ser  Leu Ala Asp
    1805                1810                1815

Asp Leu  Asn Glu Leu Asn Asn  Glu Leu Gln Lys Lys  Gln Lys Ala
    1820                1825                1830

Tyr Asn  Lys Ile Leu Arg Glu  Lys Asp Gly Ile Asp  Gln Glu Asn
    1835                1840                1845

Asp Glu  Leu Arg Arg Gln Ile  Lys Arg Leu Ser Ser  Gly Leu Gln
    1850                1855                1860

Ser Lys  Thr Leu Ile Asp Asn  Lys Gln Ser Leu Ile  Asp Glu Leu
    1865                1870                1875

Gln Lys  Lys Val Lys Lys Leu  Glu Ser Gln Leu Glu  Arg Lys Val
    1880                1885                1890

Asp Asp  Val Asp Ile Lys Pro  Val Lys Glu Lys Ser  Ser Lys Glu
    1895                1900                1905

Glu Leu  Ile Arg Trp Glu Glu  Gly Lys Lys Trp Gln  Thr Lys Val
    1910                1915                1920

Glu Gly  Leu Arg Asn Arg Leu  Lys Glu Lys Glu Gly  Glu Ala His
    1925                1930                1935

Gly Leu  Ala Lys Gln Leu Asn  Thr Leu Lys Glu Leu  Phe Ala Lys
    1940                1945                1950

Ala Asp  Lys Glu Lys Leu Thr  Leu Gln Lys Lys Leu  Lys Thr Thr
    1955                1960                1965

Gly Met  Thr Val Asp Gln Val  Leu Gly Val Arg Ala  Leu Glu Ser
    1970                1975                1980

Glu Lys  Glu Leu Glu Glu Leu  Lys Lys Lys Asn Leu  Asp Leu Glu
    1985                1990                1995

Asn Asp  Ile Leu Tyr Met Arg  Thr Gln Gln Ala Leu  Pro Arg Asp
    2000                2005                2010

Ser Val  Val Glu Asp Leu His  Leu Gln Asn Lys Tyr  Leu Gln Glu
    2015                2020                2025

Lys Leu  His Thr Leu Glu Lys  Lys Leu Ser Lys Glu  Lys Tyr Ser
    2030                2035                2040

Gln Ser  Leu Thr Ser Glu Ile  Glu Ser Asp Asp His  Cys Gln Lys
    2045                2050                2055

Glu Gln  Glu Leu Gln Lys Glu  Asn Leu Lys Leu Ser  Ser Glu Asn
    2060                2065                2070

Ile Glu  Leu Lys Phe Gln Leu  Glu Gln Ala Asn Lys  Asp Leu Pro
    2075                2080                2085

Arg Leu  Lys Asn Gln Val Lys  Asp Leu Lys Glu Met  Cys Glu Phe
    2090                2095                2100

Leu Lys  Lys Gly Lys Leu Glu  Leu Glu Arg Lys Leu  Gly Gln Val
    2105                2110                2115

Arg Gly  Ala Gly Arg Ser Gly  Lys Thr Ile Pro Glu  Leu Glu Lys
    2120                2125                2130

Thr Ile  Gly Leu Met Lys Lys  Val Val Glu Lys Val  Gln Arg Glu
    2135                2140                2145
```

Asn Glu Gln Leu Lys Lys Ala Ser Gly Ile Leu Thr Ser Glu Lys
    2150                2155                2160

Met Ala Thr Ile Glu Glu Glu Asn Arg Asn Leu Lys Ala Glu Leu
    2165                2170                2175

Glu Lys Leu Lys Ala His Phe Gly Arg Gln Leu Ser Met Gln Phe
    2180                2185                2190

Glu Ser Lys Asn Lys Gly Thr Glu Lys Ile Val Ala Glu Asn Glu
    2195                2200                2205

Arg Leu Arg Lys Glu Leu Lys Lys Glu Ile Glu Ala Ser Glu Lys
    2210                2215                2220

Leu Arg Ile Ala Lys Asn Asn Leu Glu Leu Val Asn Asp Lys Met
    2225                2230                2235

Ala Ala Gln Leu Glu Glu Thr Gly Lys Arg Leu Gln Phe Ala Glu
    2240                2245                2250

Ser Arg Ala Pro Gln Leu Glu Gly Ala Asp Ser Lys Ser Trp Lys
    2255                2260                2265

Ser Ile Val Val Ser Arg Val Tyr Glu Thr Lys Met Lys Glu Leu
    2270                2275                2280

Glu Ser Asp Ile Ala Lys Lys Asn Gln Ser Ile Thr Asp Leu Lys
    2285                2290                2295

Gln Leu Val Arg Glu Ala Thr Glu Arg Glu Gln Lys Ala Lys Lys
    2300                2305                2310

Tyr Thr Glu Asp Leu Glu Gln Gln Ile Glu Ile Leu Lys Asn Val
    2315                2320                2325

Pro Glu Gly Ala Glu Thr Glu Gln Glu Leu Ile Arg Glu Leu Gln
    2330                2335                2340

Leu Leu Arg Leu Ala Asn Asn Gln Met Asp Lys Glu Arg Ala Glu
    2345                2350                2355

Leu Ile His Gln Ile Glu Ile Asn Lys Asp Gln Thr Arg Ala Asp
    2360                2365                2370

Ser Ser Ile Pro Asp Ser Asp Gln Leu Lys Glu Lys Ile Asn Asp
    2375                2380                2385

Leu Glu Thr Gln Leu Arg Lys Leu Glu Leu Glu Lys Gln His Ser
    2390                2395                2400

Lys Glu Glu Val Lys Lys Leu Lys Lys Glu Leu Glu Asn Phe Asp
    2405                2410                2415

Pro Ser Phe Phe Glu Glu Ile Glu Asp Leu Lys Tyr Asn Tyr Lys
    2420                2425                2430

Glu Glu Val Lys Lys Asn Ile Leu Leu Glu Glu Lys Leu Lys Lys
    2435                2440                2445

Leu Ser Glu Gln Phe Gly Phe Glu Leu Pro Ser Pro Leu Ala Ala
    2450                2455                2460

Ser Glu His Ser Glu Asp Gly Glu Ser Pro His Ser Phe Pro Ile
    2465                2470                2475

Tyr

<210> SEQ ID NO 3
<211> LENGTH: 7440
<212> TYPE: DNA
<213> ORGANISM: Mus musculus

<400> SEQUENCE: 3
ctaataaata gggaaactat gaggactttc tccatcttcc gagtgttcag aagcagcaag      60

-continued

```
aggactaggc agttcaaatc caaactgttc cgacagtttt tttagcttct cttctaatag    120
gatattcttt ttcacttctt ccttataatt atacttcagg tcttcaattt cttcaaaaaa    180
tgaaggatca aaattttcca gttctttttt cagcttttta acttcctcct tcgaatgttg    240
cttttctagc tccaactttc tgagttgtgt ctccaggtca tttatctttt cctttagttg    300
atcagaatca ggtatgctac tgtcagctct ggtttggtcc ttgttaattt ctatctgatg    360
gattaattct gccctttctt tatccatctg attattggct aatctaagaa gctggagttc    420
ccgtataagc tcttgctctg tctcggcacc ttcaggaaca tttttgagga tctcaatctg    480
ttgttcaagg tcttcagtgt atttcttagc tttctgttct ctctctgttg cttctcttac    540
aagctgttta aggtcagtga tactttgatt ctttttggca atgtcacttt caagctcttt    600
catcttggtc tcatacactc ttgagaccac aattgacttc cagctcttgc tgtcagcacc    660
ttccagctgt ggggctctac tttctgcaaa ctgtagtctc ttcccagttt cttcgagttg    720
agctgccatc ttgtcgttca ccagctctaa gttgttctta gctatccgca gtttctcaga    780
ggcttctatt tctttcttaa gttctttccg aagccgttca ttttcggcaa caattttctc    840
agtacctttg ttcttagatt caaactgcat actcaactga cgtccaaagt gagctttaag    900
cttttctagt tcagccttta agtttctatt ttcttcctca atagtagcca ttttttcact    960
agtcagtatt cctgatgcct ttttcaattg ttcattttct ctttggactt tttcaactac   1020
tttcttcatt aacccaatgg ttttttctag ttctgggatt gtcttcccac ttctaccagc   1080
ccctctgacc tgaccaagct tccgctcaag ttccagtttt cctttcttaa gaaattcaca   1140
catttccttc aaatctttca cttgattctt tagtcttggc aaatctttat ttgcttgttc   1200
aagttgaaat ttcagctcga tgttttcaga tgacaacttc aaattttcct tctgaagttc   1260
ttgttctttt tgacagtgat catctgactc tatttctgaa gtcaaagact gagaatattt   1320
ctcctttgaa agtttttttt ctaaagtatg aagtttttct tgaaggtatt tattttgtaa   1380
atgtaagtct tccacaacag aatctcgtgg aagagcctgc tgggtcctca tgtataatat   1440
gtcattttct aggtccagat ttttcttttt tagctcttcc aactcttttt cagattccaa   1500
agctcgcact cctaaaacct ggtcaacagt cattcctgtt gttttcagtt tcttctgcaa   1560
agtaagtttc tctttatcag ctttggcaaa aagttccttt aaggtattca gctgctttgc   1620
caggccgtgg gcttctcctt ccttctcctt tagtctgttt cgtagtccct ctactttggt   1680
ttgccatttc ttaccttctt cccacctaat taattcttct ttactactct tttccttcac   1740
cggctttatg tctacgtcat ccacctttct ttccagttgg ctttcaagtt ttttaacttt   1800
cttttgaagt tcatcgatta aactttgctt gttatctatc aaagttttgc tctgcagtcc   1860
actggacagt cttttaatct gtcttctcag ttcatcattt tcttgatcaa ttccatcttt   1920
ctctctaagg attttattat aagcttttttg cttttttttgc agttcattat ttaattcatt   1980
taaatcatca gctagtgaat tttctttgtt cttacttgtt ttaagagctt ctttcaattt   2040
taaaagattt tcatttaaat cttcaatttg tgactttagc tctctagtat ggcgctcaac   2100
aacttgttga acattgagat ttgcctcttt ttgagaagtt acagcgatta tacgttcctc   2160
agctgctgct gtcatttccg accgaagttc caacagggct cgactaagtg ccttttgttg   2220
cttctctttc aaggctagtt ggctctttag cctgtctaca agattcctca ttgtggttgt   2280
tggagctctg gagtttgctt ctttctgagc ctggagttca gactttaaac tctgggagtc   2340
cttgtgtgct tgggctagag catgccttaa gtcctctacc tctgctttca ctttctttac   2400
ctcactggca tgagtttctt ggagccgtag tttggtattt tcaaactctc tgacttttaa   2460
```

-continued

```
ctcagtgatt tctttttgtt tttccaaatc ttttgatact ttctttagtt tggtcaaaag   2520
tgaggacaga gagtcatctt gttctgctac tgtctgctcc atctcggcca gacgaatgaa   2580
atgtttgttg gtgggaactg gagcaggaga ctgcttaagt aaatcctgag ctgtctgtct   2640
gaatttattg agtgaattat cggcctgttg ttctaatttg tgatgaagaa catgaaggtc   2700
ttcctcatgc ttcttaacaa tttctctttg ctcctctctg gccttctcca gaaggtgctg   2760
gtatttcttc aatacttctt ccttgtgatt taaccttgcc tgcatgttgg caatagtttg   2820
gtgggcaatt ttcattgtgt gatgagattt cggctccagc tcttttcttt ctagctcagc   2880
tataagtttt tctcgatcag ccgtggcagg caatcgaagc ctcagttcat tgattacttt   2940
gtctcttgac agaatatttt gctctgccaa ccgtaaagca gattcttttt cttttagttt   3000
ctcttctagt gacttgcaag ttgcttgtgt tttaagaatt acttgaatat tctccttaat   3060
ttttcttaga gcaatttcaa gttggtttgg aagaggcaag ctggggtctg gcattgatcc   3120
tgtagagtct tcaaactttt gtgctgcact gagtatttca ttttgctgat gatcaaaaat   3180
gtctaactgg cgttccagct caacttctct ttgatcccaa gccatctgtc tttcttcatg   3240
gaacttgctt tgctgaacaa tttcttcctc tagactgttg attgtatgct catattcaga   3300
gatgatatta ttcaaatatt tgatttcttc tttacccttg actagttctc tatttagctt   3360
aagttcttgg aggcgaagtt cttctatttt cacatgccaa ttgattacct tctgggctcc   3420
cctggcatcc tttaaagtac tgatcaattc ttctaagcct tttaatttta attccaactc   3480
cagtgttttg ttttccatat ttctgtgttc ctgttgcgaa ttcttcattt cttgcattat   3540
cttaagtttg tcattttgca actgaatcat cgttttggag aacttttcct gctgtgctaa   3600
gggtagagct ccactgaact gtcttcgaag cgactgaatg gtttggcgca ggtgttttgc   3660
tctgtttcta ccttccaaac gagcatagta gagcgcctgc tctttttcat ccagtttctg   3720
ttctaagcgc aaattgtagg cttccatctt ctggagtttg gacgtaactg actctaactt   3780
accgagggca gtggcctcac taatttgaag agagacaaca tgttggtgca atttggcaat   3840
tagagccttt tcgtcagatt gtgcctggaa gtccagcagc tgcgttctga gggattccac   3900
ttccttttcc ctggactgtt gttgcgaatt caaaaaatca acttgtcttt tggcaatatc   3960
tgaaatctct ctcagcttgg acacttcaac tttgagctcc acttcactct tctctagttc   4020
tagaatccgc tgtcggtcag catcacttac tgccttggtc acactatcag ctaattcgtc   4080
tctcaacatc tgctccacct tttgtgcatc caggttgatt ttagtaagct cagtgaactt   4140
ggtttccaat tcaaaattac gttcttccat ttgctttaat gaagtcctta agtgctcata   4200
cattttctga cagtgttcag ccctctgcct ttcatttaat tccttcatct ccaacacagt   4260
gattttcttt gaaatagaaa caatgtcact gtttgtcatt gatttcttag ccttatccat   4320
gtttgagtca tttcctaact tcgtttcttg ttcccaggcc tgttcaatgg tatggagttt   4380
ttcctttgta atctccagct ctttactgat agcctccatc tgttctttta gcgatgcatt   4440
ctcacactcc aggtgttcta agttacttgt tctttgaaca agcatattat ctttctgcaa   4500
gatgtccctg tacttagtag tcagctcatt gtactgttta ttggctagtt ctaattcaga   4560
caaagaaaca ctattatcta taaccttctg aagagctgca atcttgaaga tggccatttc   4620
cttgaatctt tgcaaacttc caagtttttc agtgacttcg gcctccatgg ctatgacgtc   4680
attcctgtgt ttcccgtttt cctttctcag gtgccgctcc atctccacta aggtggtgta   4740
ctgccggatg agggacttct cgttcacttg cagaacggtg attttcctac tgtttctga    4800
```

-continued

```
gagcattttc ttcatctcgt tcgaatccat ctgaagagca ctgagcaaat tgttgtactc   4860
ttttactttc acagcatcct gctcagcttg atcttccagt tttctcttct cctctcttat   4920
catctcagag tctgttttcc aaatatcctt ttcacttagg tattctttat ataataaact   4980
ttgttgatga cgaatcactg caaactttct gttataatct tcaagggaat cttctaaatg   5040
ttttaatttc ttttctttat tgtctagttc ctgcaaaaga tgtattaagt attcattctg   5100
agaattgatg atataggcac tggatggtgc tatcccatcg ggtaagtcta tgcctttgta   5160
tactacattg gagcctgcag actgacgtag aaggtcagtt tccttctcaa ggtggtcaat   5220
ctttaagttt gcttttacca actgctgtga ataatttaca gcctctttcc gagattgcct   5280
gagttcttgc cttaattctt cattccttcc tgtaagttgg tcaacttggg cttttagatg   5340
caagctggca tcgaagattc cttctgcatt ctttgattcc atagcgttaa ccagtctttc   5400
aagactcggg atgattaaag atgtttcacc tcctttcaca tcagaatcct tcggcatgtc   5460
cttaatagct tgcaaaattt ctttcatacc ttcttcaagt tgcttatttt cttcgactaa   5520
ttcttttagt ttactctgga atttagcaat tactgtccta cttctttcta aatcttttc   5580
cttttcagcc aattctcttg aaagaaactc attctttgat tgtgtttcat tcatattatt   5640
gaggctcata aaatttagtt ttcttccttc tattttattt tcatgagaaa aggtttcaga   5700
taagttcaag tcgtcaatgg ttaatcctga ggctgcgttc cttttgcctc tttcttgagc   5760
catttgacga atctttcttt tcaagtcaag acgctcctcc tctagacttt cgatctcttt   5820
caaaagaacc tggttctcag ctctgtactg ttgctgcttt aaccgtttgc tgtttctaaa   5880
ttcagtcaaa tcaatcattg tcttgggttc aaggccagcc cgctctctaa gggcttcgtt   5940
ttcatcaagg atgtcattga tcttcatctc aagcttattg atctccttgg tcaacacttc   6000
catctctcca tctcttattt taatttgggc tttacaattc tttatttcga taacagcatc   6060
ttctaagcca tatactccag attcataatc ttttaatctc ttcagagcct caaccaattc   6120
tttgtccttc tccctggcat cagcctcagc cagctcagct attctctcgg cctcttttgt   6180
tttctcttct aaaatttgta cttttgagtg aattttcata taatgagtct gctgataaaa   6240
gtttgaagta cctttgtctt tttggagttc atttttcaaa tcttcaataa taaacgtatt   6300
tttttccatt tctttcgtat actgttctac ttgctcagta agcatcttaa tttgactgtc   6360
tcgctcctgg ataccctgtt tcagagccat gatgttactt ttgtctgcat caagttgggc   6420
atttttaagt ttccctctca gactctgtag catttgctga tattcaatga tttcatcatc   6480
tttagaagac aaaattaact tccactcttc cacttttgcg ttaacagcca tcatgactgg   6540
atcgtcctct tcatccttcg ccttcagaag atccgtgagc tctcgaactt gcaggcgata   6600
gtgctcattc tccttcttga tctggtccat gacagcatcc gactgatgca caagcgcttt   6660
catcctgttg tactcatcag tcatcttctc catctcctgc acagactctt ccaggttttt   6720
cctcatttct tggttctgaa cttcaatctt ctcattagct tctgttaagg tctgtatttc   6780
gtccagatat tgaacaagtt catagttctt tttagacaac tgtgatcggt agtcactgtc   6840
ttctcctctc cttgacagaa gtgattcttt ctgtgaatct atttgtttct ggtagtcaat   6900
aatgtcctgc cgaagctgct cattcttttt ctttagacgt ttgttctctc ttcttaattt   6960
gctgttttca ttttctgcct cctcatttcg aagagccaat tgttcattaa ccttctttc   7020
tttatccaat tctttttcca tatcctctaa ttctctatct ttttgttcca gctgcttctc   7080
aagttggcga atttcgtcac gtaaaaaccg agtgtcacgt ccccctgcag actgctgagc   7140
catctccagt tcattttcca gtttcattac ttttgtcttt aattgatttt caaattttgc   7200
```

-continued ttgttcttct ccagcctttt caacttcttc caaagcgagc tctacttcct gggctttcat 7260
cttcattaga gactgggtaa ttctgaatag atgtatcatg ttttcttggt cttcattttt 7320
tagttcattt acttccacct tggataaaga tatcaataat ttatctgcta actcttcttg 7380
ccgtggcagg tcatctggat caactttgat taattctttc cactttatat taggtggcat 7440

<210> SEQ ID NO 4
<211> LENGTH: 2970
<212> TYPE: DNA
<213> ORGANISM: Mus musculus

<400> SEQUENCE: 4
ttggcagagc aaaatattct gtcaagagac aaagtaatca atgaactgag gcttcgattg 60
cctgccacgg ctgatcgaga aaaacttata gctgagctag aaagaaaaga gctggagccg 120
aaatctcatc acacaatgaa aattgcccac caaactattg ccaacatgca ggcaaggtta 180
aatcacaagg aagaagtatt gaagaaatac cagcaccttc tggagaaggc cagagaggag 240
caaagagaaa ttgttaagaa gcatgaggaa gaccttcatg ttcttcatca caaattagaa 300
caacaggccg ataattcact caataaattc agacagacag ctcaggattt acttaagcag 360
tctcctgctc cagttcccac caacaaacat ttcattcgtc tggccgagat ggagcagaca 420
gtagcagaac aagatgactc tctgtcctca cttttgacca aactaaagaa agtatcaaaa 480
gatttggaaa aacaaaaaga aatcactgag ttaaaagtca gagagtttga aaataccaaa 540
ctacggctcc aagaaactca tgccagtgag gtaaagaaag tgaaagcaga ggtagaggac 600
ttaaggcatg ctctagccca agcacacaag gactcccaga gtttaaagtc tgaactccag 660
gctcagaaag aagcaaactc cagagctcca acaaccacaa tgaggaatct tgtagacagg 720
ctaaagagcc aactagcctt gaaagagaag caacaaaagg cacttagtcg agccctgttg 780
gaacttcggt cggaaatgac agcagcagct gaggaacgta taatcgctgt aacttctcaa 840
aaagaggcaa atctcaatgt tcaacaagtt gttgagcgcc atactagaga gctaaagtca 900
caaattgaag atttaaatga aaatctttta aaattgaaag aagctcttaa aacaagtaag 960
aacaaagaaa attcactagc tgatgattta aatgaattaa ataatgaact gcaaaaaaag 1020
caaaaagctt ataataaaat ccttagagag aaagatggaa ttgatcaaga aaatgatgaa 1080
ctgagaagac agattaaaag actgtccagt ggactgcaga gcaaaacttt gatagataac 1140
aagcaaagtt taatcgatga acttcaaaag aaagttaaaa aacttgaaag ccaactggaa 1200
agaaaggtgg atgacgtaga cataaagccg gtgaaggaaa agagtagtaa agaagaatta 1260
attaggtggg aagaaggtaa gaaatggcaa accaaagtag agggactacg aaacagacta 1320
aaggagaagg aaggagaagc ccacggcctg gcaaagcagc tgaatacctt aaaggaactt 1380
tttgccaaag ctgataaaga gaaacttact ttgcagaaga aactgaaaac aacaggaatg 1440
actgttgacc aggttttagg agtgcgagct ttggaatctg aaaaagagtt ggaagagcta 1500
aaaaagaaaa atctggacct agaaaatgac atattataca tgaggaccca gcaggctctt 1560
ccacgagatt ctgttgtgga agacttacat ttacaaaata aatacettca agaaaaactt 1620 catactttag aaaaaaaact ttcaaaggag aaatattctc agtctttgac ttcagaaata 1680
gagtcagatg atcactgtca aaaagaacaa gaacttcaga aggaaaattt gaagttgtca 1740
tctgaaaaca tcgagctgaa atttcaactt gaacaagcaa ataaagattt gccaagacta 1800
aagaatcaag tgaaagattt gaaggaaatg tgtgaatttc ttaagaaagg aaaactggaa 1860

-continued

```
cttgagcgga agcttggtca ggtcagaggg gctggtagaa gtgggaagac aatcccagaa   1920

ctagaaaaaa ccattgggtt aatgaagaaa gtagttgaaa aagtccaaag agaaaatgaa   1980

caattgaaaa aggcatcagg aatactgact agtgaaaaaa tggctactat tgaggaagaa   2040

aatagaaact taaaggctga actagaaaag cttaaagctc actttggacg tcagttgagt   2100

atgcagtttg aatctaagaa caaaggtact gagaaaattg ttgccgaaaa tgaacggctt   2160

cggaaagaac ttaagaaaga aatagaagcc tctgagaaac tgcggatagc taagaacaac   2220

ttagagctgg tgaacgacaa gatggcagct caactcgaag aaactgggaa gagactacag   2280

tttgcagaaa gtagagcccc acagctggaa ggtgctgaca gcaagagctg gaagtcaatt   2340

gtggtctcaa gagtgtatga gaccaagatg aaagagcttg aaagtgacat tgccaaaaag   2400

aatcaaagta tcactgacct taaacagctt gtaagagaag caacagagag agaacagaaa   2460

gctaagaaat acactgaaga ccttgaacaa cagattgaga tcctcaaaaa tgttcctgaa   2520

ggtgccgaga cagagcaaga gcttatacgg gaactccagc ttcttagatt agccaataat   2580

cagatggata aagaaagggc agaattaatc catcagatag aaattaacaa ggaccaaacc   2640

agagctgaca gtagcatacc tgattctgat caactaaagg aaaagataaa tgacctggag   2700

acacaactca gaaagttgga gctagaaaag caacattcga aggaggaagt taaaaagctg   2760

aaaaaagaac tggaaaattt tgatccttca ttttttgaag aaattgaaga cctgaagtat   2820

aattataagg aagaagtgaa aaagaatatc ctattagaag agaagctaaa aaaactgtcg   2880

gaacagtttg gatttgaact gcctagtcct cttgctgctt ctgaacactc ggaagatgga   2940

gaaagtcctc atagtttccc tatttattag                                    2970
```

<210> SEQ ID NO 5
<211> LENGTH: 989
<212> TYPE: PRT
<213> ORGANISM: Mus musculus

<400> SEQUENCE: 5

```
Leu Ala Glu Gln Asn Ile Leu Ser Arg Asp Lys Val Ile Asn Glu Leu
1               5                   10                  15

Arg Leu Arg Leu Pro Ala Thr Ala Asp Arg Glu Lys Leu Ile Ala Glu
            20                  25                  30

Leu Glu Arg Lys Glu Leu Glu Pro Lys Ser His His Thr Met Lys Ile
        35                  40                  45

Ala His Gln Thr Ile Ala Asn Met Gln Ala Arg Leu Asn His Lys Glu
    50                  55                  60

Glu Val Leu Lys Lys Tyr Gln His Leu Leu Glu Lys Ala Arg Glu Glu
65                  70                  75                  80

Gln Arg Glu Ile Val Lys Lys His Glu Glu Asp Leu His Val Leu His
                85                  90                  95

His Lys Leu Glu Gln Gln Ala Asp Asn Ser Leu Asn Lys Phe Arg Gln
            100                 105                 110

Thr Ala Gln Asp Leu Leu Lys Gln Ser Pro Ala Pro Val Pro Thr Asn
        115                 120                 125

Lys His Phe Ile Arg Leu Ala Glu Met Glu Gln Thr Val Ala Glu Gln
    130                 135                 140

Asp Asp Ser Leu Ser Ser Leu Leu Thr Lys Leu Lys Lys Val Ser Lys
145                 150                 155                 160

Asp Leu Glu Lys Gln Lys Glu Ile Thr Glu Leu Lys Val Arg Glu Phe
                165                 170                 175
```

-continued

```
Glu Asn Thr Lys Leu Arg Leu Gln Glu Thr His Ala Ser Glu Val Lys
            180                 185                 190

Lys Val Lys Ala Glu Val Glu Asp Leu Arg His Ala Leu Ala Gln Ala
        195                 200                 205

His Lys Asp Ser Gln Ser Leu Lys Ser Glu Leu Gln Ala Gln Lys Glu
    210                 215                 220

Ala Asn Ser Arg Ala Pro Thr Thr Thr Met Arg Asn Leu Val Asp Arg
225                 230                 235                 240

Leu Lys Ser Gln Leu Ala Leu Lys Glu Lys Gln Gln Lys Ala Leu Ser
                245                 250                 255

Arg Ala Leu Leu Glu Leu Arg Ser Glu Met Thr Ala Ala Ala Glu Glu
            260                 265                 270

Arg Ile Ile Ala Val Thr Ser Gln Lys Glu Ala Asn Leu Asn Val Gln
        275                 280                 285

Gln Val Val Glu Arg His Thr Arg Glu Leu Lys Ser Gln Ile Glu Asp
    290                 295                 300

Leu Asn Glu Asn Leu Leu Lys Leu Lys Glu Ala Leu Lys Thr Ser Lys
305                 310                 315                 320

Asn Lys Glu Asn Ser Leu Ala Asp Asp Leu Asn Glu Leu Asn Asn Glu
                325                 330                 335

Leu Gln Lys Lys Gln Lys Ala Tyr Asn Lys Ile Leu Arg Glu Lys Asp
            340                 345                 350

Gly Ile Asp Gln Glu Asn Asp Glu Leu Arg Arg Gln Ile Lys Arg Leu
        355                 360                 365

Ser Ser Gly Leu Gln Ser Lys Thr Leu Ile Asp Asn Lys Gln Ser Leu
    370                 375                 380

Ile Asp Glu Leu Gln Lys Lys Val Lys Lys Leu Glu Ser Gln Leu Glu
385                 390                 395                 400

Arg Lys Val Asp Asp Val Asp Ile Lys Pro Val Lys Glu Lys Ser Ser
                405                 410                 415

Lys Glu Glu Leu Ile Arg Trp Glu Glu Gly Lys Lys Trp Gln Thr Lys
            420                 425                 430

Val Glu Gly Leu Arg Asn Arg Leu Lys Glu Lys Glu Gly Glu Ala His
        435                 440                 445

Gly Leu Ala Lys Gln Leu Asn Thr Leu Lys Glu Leu Phe Ala Lys Ala
    450                 455                 460

Asp Lys Glu Lys Leu Thr Leu Gln Lys Lys Leu Lys Thr Thr Gly Met
465                 470                 475                 480

Thr Val Asp Gln Val Leu Gly Val Arg Ala Leu Glu Ser Glu Lys Glu
                485                 490                 495

Leu Glu Glu Leu Lys Lys Lys Asn Leu Asp Leu Glu Asn Asp Ile Leu
            500                 505                 510

Tyr Met Arg Thr Gln Gln Ala Leu Pro Arg Asp Ser Val Val Glu Asp
        515                 520                 525

Leu His Leu Gln Asn Lys Tyr Leu Gln Glu Lys Leu His Thr Leu Glu
    530                 535                 540

Lys Lys Leu Ser Lys Glu Lys Tyr Ser Gln Ser Leu Thr Ser Glu Ile
545                 550                 555                 560

Glu Ser Asp Asp His Cys Gln Lys Glu Gln Glu Leu Gln Lys Glu Asn
                565                 570                 575

Leu Lys Leu Ser Ser Glu Asn Ile Glu Leu Lys Phe Gln Leu Glu Gln
            580                 585                 590

Ala Asn Lys Asp Leu Pro Arg Leu Lys Asn Gln Val Lys Asp Leu Lys
```

-continued

```
        595                 600                 605

Glu Met Cys Glu Phe Leu Lys Lys Gly Lys Leu Glu Leu Glu Arg Lys
    610                 615                 620

Leu Gly Gln Val Arg Gly Ala Gly Arg Ser Gly Lys Thr Ile Pro Glu
625                 630                 635                 640

Leu Glu Lys Thr Ile Gly Leu Met Lys Lys Val Val Glu Lys Val Gln
                645                 650                 655

Arg Glu Asn Glu Gln Leu Lys Lys Ala Ser Gly Ile Leu Thr Ser Glu
            660                 665                 670

Lys Met Ala Thr Ile Glu Glu Glu Asn Arg Asn Leu Lys Ala Glu Leu
        675                 680                 685

Glu Lys Leu Lys Ala His Phe Gly Arg Gln Leu Ser Met Gln Phe Glu
    690                 695                 700

Ser Lys Asn Lys Gly Thr Glu Lys Ile Val Ala Glu Asn Glu Arg Leu
705                 710                 715                 720

Arg Lys Glu Leu Lys Lys Glu Ile Glu Ala Ser Glu Lys Leu Arg Ile
                725                 730                 735

Ala Lys Asn Asn Leu Glu Leu Val Asn Asp Lys Met Ala Ala Gln Leu
            740                 745                 750

Glu Glu Thr Gly Lys Arg Leu Gln Phe Ala Glu Ser Arg Ala Pro Gln
        755                 760                 765

Leu Glu Gly Ala Asp Ser Lys Ser Trp Lys Ser Ile Val Val Ser Arg
    770                 775                 780

Val Tyr Glu Thr Lys Met Lys Glu Leu Glu Ser Asp Ile Ala Lys Lys
785                 790                 795                 800

Asn Gln Ser Ile Thr Asp Leu Lys Gln Leu Val Arg Glu Ala Thr Glu
                805                 810                 815

Arg Glu Gln Lys Ala Lys Lys Tyr Thr Glu Asp Leu Glu Gln Gln Ile
            820                 825                 830

Glu Ile Leu Lys Asn Val Pro Glu Gly Ala Glu Thr Glu Gln Glu Leu
        835                 840                 845

Ile Arg Glu Leu Gln Leu Leu Arg Leu Ala Asn Asn Gln Met Asp Lys
    850                 855                 860

Glu Arg Ala Glu Leu Ile His Gln Ile Glu Ile Asn Lys Asp Gln Thr
865                 870                 875                 880

Arg Ala Asp Ser Ser Ile Pro Asp Ser Asp Gln Leu Lys Glu Lys Ile
                885                 890                 895

Asn Asp Leu Glu Thr Gln Leu Arg Lys Leu Glu Leu Glu Lys Gln His
            900                 905                 910

Ser Lys Glu Glu Val Lys Lys Leu Lys Lys Glu Leu Glu Asn Phe Asp
        915                 920                 925

Pro Ser Phe Phe Glu Glu Ile Glu Asp Leu Lys Tyr Asn Tyr Lys Glu
    930                 935                 940

Glu Val Lys Lys Asn Ile Leu Leu Glu Glu Lys Leu Lys Lys Leu Ser
945                 950                 955                 960

Glu Gln Phe Gly Phe Glu Leu Pro Ser Pro Leu Ala Ala Ser Glu His
                965                 970                 975

Ser Glu Asp Gly Glu Ser Pro His Ser Phe Pro Ile Tyr
            980                 985
```

<210> SEQ ID NO 6
<211> LENGTH: 2970
<212> TYPE: DNA
<213> ORGANISM: Mus musculus -continued

<400> SEQUENCE: 6

```
ctaataaata gggaaactat gaggactttc tccatcttcc gagtgttcag aagcagcaag     60
aggactaggc agttcaaatc caaactgttc cgacagtttt tttagcttct cttctaatag    120
gatattcttt ttcacttctt ccttataatt atacttcagg tcttcaattt cttcaaaaaa    180
tgaaggatca aaattttcca gttctttttt cagcttttta acttcctcct tcgaatgttg    240
cttttctagc tccaactttc tgagttgtgt ctccaggtca tttatctttt cctttagttg    300
atcagaatca ggtatgctac tgtcagctct ggtttggtcc ttgttaattt ctatctgatg    360
gattaattct gccctttctt tatccatctg attattggct aatctaagaa gctggagttc    420
ccgtataagc tcttgctctg tctcggcacc ttcaggaaca tttttgagga tctcaatctg    480
ttgttcaagg tcttcagtgt atttcttagc tttctgttct ctctctgttg cttctcttac    540
aagctgttta aggtcagtga tactttgatt ctttttggca atgtcacttt caagctcttt    600
catcttggtc tcatacactc ttgagaccac aattgacttc cagctcttgc tgtcagcacc    660
ttccagctgt ggggctctac tttctgcaaa ctgtagtctc ttcccagttt cttcgagttg    720
agctgccatc ttgtcgttca ccagctctaa gttgttctta gctatccgca gtttctcaga    780
ggcttctatt tctttcttaa gttctttccg aagccgttca ttttcggcaa caattttctc    840
agtacctttg ttcttagatt caaactgcat actcaactga cgtccaaagt gagctttaag    900
cttttctagt tcagccttta agtttctatt ttcttcctca atagtagcca ttttttcact    960
agtcagtatt cctgatgcct tttcaattg ttcattttct ctttggactt tttcaactac   1020
tttcttcatt aacccaatgg ttttttctag ttctgggatt gtcttcccac ttctaccagc   1080
ccctctgacc tgaccaagct tccgctcaag ttccagtttt cctttcttaa gaaattcaca   1140
catttccttc aaatctttca cttgattctt tagtcttggc aaatctttat ttgcttgttc   1200
aagttgaaat ttcagctcga tgttttcaga tgacaacttc aaattttcct tctgaagttc   1260
ttgttctttt tgacagtgat catctgactc tatttctgaa gtcaaagact gagaatattt   1320
ctcctttgaa agtttttttt ctaaagtatg aagtttttct tgaaggtatt tattttgtaa   1380
atgtaagtct tccacaacag aatctcgtgg aagagcctgc tgggtcctca tgtataaatat   1440
gtcattttct aggtccagat ttttcttttt tagctcttcc aactcttttt cagattccaa   1500
agctcgcact cctaaaacct ggtcaacagt cattcctgtt gttttcagtt tcttctgcaa   1560
agtaagtttc tctttatcag ctttggcaaa aagttccttt aaggtattca gctgctttgc   1620
caggccgtgg gcttctcctt ccttctcctt tagtctgttt cgtagtccct ctactttggt   1680
ttgccatttc ttaccttctt cccacctaat taattcttct ttactactct tttccttcac   1740
cggctttatg tctacgtcat ccacctttct ttccagttgg ctttcaagtt ttttaacttt   1800
cttttgaagt tcatcgatta aactttgctt gttatctatc aaagttttgc tctgcagtcc   1860
actggacagt cttttaatct gtcttctcag ttcatcattt tcttgatcaa ttccatcttt   1920
ctctctaagg attttattat aagctttttg cttttttgc agttcattat ttaattcatt   1980
taaatcatca gctagtgaat tttctttgtt cttacttgtt ttaagagctt ctttcaattt   2040
taaaagattt tcatttaaat cttcaatttg tgactttagc tctctagtat ggcgctcaac   2100
aacttgttga acattgagat ttgcctcttt ttgagaagtt acagcgatta tacgttcctc   2160
agctgctgct gtcatttccg accgaagttc caacagggct cgactaagtg ccttttgttg   2220
cttctctttc aaggctagtt ggctctttag cctgtctaca agattcctca ttgtggttgt   2280
```

-continued tggagctctg gagtttgctt ctttctgagc ctggagttca gactttaaac tctgggagtc 2340
cttgtgtgct tgggctagag catgccttaa gtcctctacc tctgctttca ctttctttac 2400
ctcactggca tgagtttctt ggagccgtag tttggtattt tcaaactctc tgacttttaa 2460
ctcagtgatt tctttttgtt tttccaaatc ttttgatact ttctttagtt tggtcaaaag 2520
tgaggacaga gagtcatctt gttctgctac tgtctgctcc atctcggcca gacgaatgaa 2580
atgtttgttg gtgggaactg gagcaggaga ctgcttaagt aaatcctgag ctgtctgtct 2640
gaatttattg agtgaattat cggcctgttg ttctaatttg tgatgaagaa catgaaggtc 2700
ttcctcatgc ttcttaacaa tttctctttg ctcctctctg gccttctcca gaaggtgctg 2760
gtatttcttc aatacttctt ccttgtgatt taaccttgcc tgcatgttgg caatagtttg 2820
gtgggcaatt ttcattgtgt gatgagattt cggctccagc tcttttcttt ctagctcagc 2880
tataagtttt tctcgatcag ccgtggcagg caatcgaagc ctcagttcat tgattacttt 2940
gtctcttgac agaatatttt gctctgccaa 2970

<210> SEQ ID NO 7
<211> LENGTH: 7440
<212> TYPE: DNA
<213> ORGANISM: Homo sapiens

<400> SEQUENCE: 7
atgccaccta atataaactg gaaagaaata atgaaagttg acccagatga cctgccccgt 60
caagaagaac tggcagataa tttattgatt tccttatcca aggtggaagt aaatgagcta 120
aaaagtgaaa agcaagaaaa tgtgatacac cttttcagaa ttactcagtc actaatgaag 180
atgaaagctc aagaagtgga gctggctttg gaagaagtag aaaaagctgg agaagaacaa 240
gcaaaatttg aaaatcaatt aaaaactaaa gtaatgaaac tggaaaatga actggagatg 300
gctcagcagt ctgcaggtgg acgagatact cggtttttac gtaatgaaat ttgccaactt 360
gaaaaacaat tagaacaaaa agatagagaa ttggaggaca tggaaaagga gttggagaaa 420
gagaagaaag ttaatgagca attggctctt cgaaatgagg aggcagaaaa tgaaaacagc 480
aaattaagaa gagagaacaa acgtctaaag aaaaagaatg aacaactttg tcaggatatt 540
attgactacc agaaacaaat agattcacag aaagaaacac ttttatcaag aagaggggaa 600
gacagtgact accgatcaca gttgtctaaa aaaaactatg agcttatcca atatcttgat 660
gaaattcaga ctttaacaga agctaatgag aaaattgaag ttcagaatca agaaatgaga 720
aaaaatttag aagagtctgt acaggaaatg gagaagatga ctgatgaata taatagaatg 780
aaagctattg tgcatcagac agataatgta atagatcagt taaaaaaaga aaacgatcat 840
tatcaacttc aagtgcagga gcttacagat cttctgaaat caaaaaatga agaagatgat 900
ccaattatgg tagctgtcaa tgcaaaagta gaagaatgga agctaatttt gtcttctaaa 960
gatgatgaaa ttattgagta tcagcaaatg ttacataacc taagggagaa acttaagaat 1020
gctcagcttg atgctgataa aagtaatgtt atggctctac agcagggtat acaggaacga 1080
gacagtcaaa ttaagatgct caccgaacaa gtagaacaat atacaaaaga aatggaaaag 1140
aatacttgta ttattgaaga tttgaaaaat gagctccaaa gaaacaaagg tgcttcaacc 1200
ctttctcaac agactcatat gaaaattcag tcaacgttag acattttaaa agagaaaact 1260
aaagaggctg agagaacagc tgaactggct gaggctgatg ctagggaaaa ggataaagaa 1320
ttagttgagg ctctgaagag gttaaaagat tatgaatcgg gagtatatgg tttagaagat 1380
gctgtcgttg aaataaagaa ttgtaaaaac caaattaaaa taagagatcg agagattgaa 1440

```
atattaacaa aggaaatcaa taaacttgaa ttgaagatca gtgatttcct tgatgaaaat   1500
gaggcactta gagagcgtgt gggccttgaa ccaaagacaa tgattgattt aactgaattt   1560
agaaatagca aacacttaaa acagcagcag tacagagctg aaaaccagat tcttttgaaa   1620
gagattgaaa gtctagagga agaacgactt gatctgaaaa aaaaaattcg tcaaatggct   1680
caagaaagag gaaaaagaag tgcaacttca ggattaacca ctgaggacct gaacctaact   1740
gaaaacattt ctcaaggaga tagaataagt gaaagaaaat tggatttatt gagcctcaaa   1800
aatatgagtg aagcacaatc aaagaatgaa tttctttcaa gagaactaat tgaaaaagaa   1860
agagatttag aaaggagtag gacagtgata gccaaatttc agaataaatt aaaagaatta   1920
gttgaagaaa ataagcaact tgaagaaggt atgaaagaaa tattgcaagc aattaaggaa   1980
atgcagaaag atcctgatgt taaaggagga gaaacatctc taattatccc tagccttgaa   2040
agactagtta atgctataga atcaaagaat gcagaaggaa tctttgatgc gagtctgcat   2100
ttgaaagccc aagttgatca gcttaccgga agaaatgaag aattaagaca ggagctcagg   2160
gaatctcgga aagaggctat aaattattca cagcagttgg caaaagctaa tttaaagata   2220
gaccatcttg aaaaagaaac tagtctttta cgacaatcag aaggatcgaa tgttgttttt   2280
aaaggaattg acttacctga tgggatagca ccatctagtg ccagtatcat taattctcag   2340
aatgaatatt taatacattt gttacaggaa ctagaaaata aagaaaaaaa gttaaagaat   2400
ttagaagatt ctcttgaaga ttacaacaga aaatttgctg taattcgtca tcaacaaagt   2460
ttgttgtata aagaatacct aagtgaaaag gagacctgga aaacagaatc taaaacaata   2520
aaagaggaaa agagaaaact tgaggatcaa gtccaacaag atgctataaa agtaaaagaa   2580
tataataatt tgctcaatgc tcttcagatg gattcggatg aaatgaaaaa aatacttgca   2640
gaaaatagta ggaaaattac tgttttgcaa gtgaatgaaa aatcacttat aaggcaatat   2700
acaaccttag tagaattgga gcgacaactt agaaaagaaa atgagaagca aaagaatgaa   2760
ttgttgtcaa tggaggctga agtttgtgaa aaaattgggt gtttgcaaag atttaaggaa   2820
atggccattt tcaagattgc agctctccaa aaagttgtag ataatagtgt ttctttgtct   2880
gaactagaac tggctaataa acagtacaat gaactgactg ctaagtacag ggacatcttg   2940
caaaaagata atatgcttgt tcaaagaaca agtaacttgg aacacctgga gtgtgaaaac   3000
atctccttaa aagaacaagt ggagtctata aataaagaac tggagattac caaggaaaaa   3060
cttcacacta ttgaacaagc ctgggaacag gaaactaaat taggtaatga atctagcatg   3120
gataaggcaa agaaatcaat aaccaacagt gacattgttt ccatttcaaa aaaaataact   3180
atgctggaaa tgaaggaatt aaatgaaagg cagcgggctg aacattgtca aaaaatgtat   3240
gaacacttac ggacttcgtt aaagcaaatg gaggaacgta attttgaatt ggaaaccaaa   3300
tttgctgagc ttaccaaaat caatttggat gcacagaagg tggaacagat gttaagagat   3360
gaattagctg atagtgtgag caaggcagta agtgatgctg ataggcaacg gattctagaa   3420
ttagagaaga atgaaatgga actaaaagtt gaagtgtcaa aactgagaga gatttctgat   3480
attgccagaa gacaagttga aattttgaat gcacaacaac aatctaggga caaggaagta   3540
gagtccctca gaatgcaact gctagactat caggcacagt ctgatgaaaa gtcgctcatt   3600
gccaagttgc accaacataa tgtctctctt caactgagtg aggctactgc tcttggtaag   3660
ttggagtcaa ttacatctaa actgcagaag atggaggcct acaacttgcg cttagagcag   3720
aaacttgatg aaaaagaaca ggctctctat tatgctcgtt tggagggaag aaacagagca   3780
```

-continued

```
aaacatctgc gccaaacaat tcagtctcta cgacgacagt ttagtggagc tttacccttg   3840
gcacaacagg aaaagttctc caaaacaatg attcaactac aaaatgacaa acttaagata   3900
atgcaagaaa tgaaaaattc tcaacaagaa catagaaata tggagaacaa aacattggag   3960
atggaattaa aattaaaggg cctggaagag ttaataagca ctttaaagga taccaaagga   4020
gcccaaaagg taatcaactg gcatatgaaa atagaagaac ttcgtcttca agaacttaaa   4080
ctaaatcggg aattagtcaa ggataaagaa gaaataaaat atttgaataa cataatttct   4140
gaatatgaac gtacaatcag cagtcttgaa gaagaaattg tgcaacagaa caagtttcat   4200
gaagaaagac aaatggcctg ggatcaaaga gaagttgacc tggaacgcca actagacatt   4260
tttgaccgtc agcaaaatga aatactaaat gcggcacaaa agtttgaaga agctacagga   4320
tcaatccctg accctagttt gccccttcca aatcaacttg agatcgctct aaggaaaatt   4380
aaggagaaca ttcgaataat tctagaaaca cgggcaactt gcaaatcact agaagagaaa   4440
ctaaaagaga aagaatctgc tttaaggtta gcagaacaaa atatactgtc aagagacaaa   4500
gtaatcaatg aactgaggct tcgattgcct gccactgcag aaagagaaaa gctcatagct   4560
gagctaggca gaaaagagat ggaaccaaaa tctcaccaca cattgaaaat tgctcatcaa   4620
accattgcaa acatgcaagc aaggttaaat caaaaagaag aagtattaaa gaagtatcaa   4680
cgtcttctag aaaaagccag agaggagcaa agagaaattg tgaagaaaca tgaggaagac   4740
cttcatattc ttcatcacag attagaacta caggctgata gttcactaaa taaattcaaa   4800
caaacggctt gggatttaat gaaacagtct cccactccag ttcctaccaa caagcatttt   4860
attcgtctgg ctgagatgga acagacagta gcagaacaag atgactctct ttcctcactc   4920
ttggtcaaac taaagaaagt atcacaagat ttggagagac aaagagaaat cactgaatta   4980
aaagtaaaag aatttgaaaa tatcaaatta cagcttcaag aaaaccatga agatgaagtg   5040
aaaaaagtaa aagcggaagt agaggattta aagtatcttc tggaccagtc acaaaaggag   5100
tcacagtgtt taaaatctga acttcaggct caaaaagaag caaattcaag agctccaaca   5160
actacaatga gaaatctagt agaacggcta aagagccaat tagccttgaa ggagaaacaa   5220
cagaaagcac ttagtcgggc acttttagaa ctccgggcag aaatgacagc agctgctgaa   5280
gaacgtatta tttctgcaac ttctcaaaaa gaggcccatc tcaatgttca acaaatcgtt   5340
gatcgacata ctagagagct aaagacacaa gttgaagatt taaatgaaaa tcttttaaaa   5400
ttgaaagaag cacttaaaac aagtaaaaac agagaaaact cactaactga taatttgaat   5460
gacttaaata atgaactgca aaagaaacaa aaagcctata ataaaatact tagagagaaa   5520
gaggaaattg atcaagagaa tgatgaactg aaaaggcaaa ttaaaagact aaccagtgga   5580
ttacagggca aacccctgac agataataaa caaagtctaa ttgaagaact ccaaaggaaa   5640
gttaaaaaac tagagaacca attagaggga aaggtggagg aagtagacct aaaacctatg   5700
aaagaaaaga atgctaaaga agaattaatt aggtgggaag aaggtaaaaa gtggcaagcc   5760
aaaatagaag gaattcgaaa caagttaaaa gagaaagagg gggaagtctt tactttaaca   5820
aagcagttga atactttgaa ggatcttttt gccaaagccg ataaagagaa acttactttg   5880
cagaggaaac taaaaacaac tggcatgact gttgatcagg ttttgggaat acgagctttg   5940
gagtcagaaa aagaattgga agaattaaaa aagagaaatc ttgacttaga aaatgatata   6000
ttgtatatga gggcccacca agctcttcct cgagattctg ttgtagaaga tttacattta   6060
caaaatagat acctccaaga aaaacttcat gctttagaaa aacagttttc aaaggataca   6120
tattctaagc cttcaatttc aggaatagag tcagatgatc attgtcagag agaacaggag   6180
```

-continued

```
cttcagaagg aaaacttgaa gttgtcatct gaaaatattg aactgaaatt tcagcttgaa   6240

caagcaaata aagatttgcc aagattaaag aatcaagtca gagatttgaa ggaaatgtgt   6300

gaatttctta agaaagaaaa agcagaagtt cagcggaaac ttggccatgt tagagggtct   6360

ggtagaagtg gaaagacaat cccagaactg gaaaaaacca ttggtttaat gaaaaaagta   6420

gttgaaaaag tccagagaga aaatgaacag ttgaaaaaag catcaggaat attgactagt   6480

gaaaaaatgg ctaatattga gcaggaaaat gaaaaattga aggctgaatt agaaaaactt   6540

aaagctcatc ttgggcatca gttgagcatg cactatgaat ccaagaccaa aggcacagaa   6600

aaaattattg ctgaaaatga aaggcttcgt aaagaactta aaaaagaaac tgatgctgca   6660

gagaaattac ggatagcaaa gaataattta gagatattaa atgagaagat gacagttcaa   6720

ctagaagaga ctggtaagag attgcagttt gcagaaagca gaggtccaca gcttgaaggt   6780

gctgacagta agagctggaa atccattgtg gttacaagaa tgtatgaaac caagttaaaa   6840

gaattggaaa ctgatattgc caaaaaaaat caaagcatta ctgaccttaa acagcttgta   6900

aaagaagcaa cagagagaga acaaaaagtt aacaaataca atgaagacct tgaacaacag   6960

attaagattc ttaaacatgt tcctgaaggt gctgagacag agcaaggcct taaacgggag   7020

cttcaagttc ttagattagc taatcatcag ctggataaag agaaagcaga attaatccat   7080

cagatagaag ctaacaagga ccaaagtgga gctgaaagca ccatacctga tgctgatcaa   7140

ctaaaggaaa aaataaaaga tctagagaca cagctcaaaa tgtcagatct agaaaagcag   7200

catttgaagg aggaaataaa gaagctgaaa aaagaactgg aaaattttga tccttcattt   7260

tttgaagaaa ttgaagatct taagtataat tacaaggaag aagtgaagaa gaatattctc   7320

ttagaagaga aggtaaaaaa actttcagaa caattgggag ttgaattaac tagccctgtt   7380

gctgcttctg aagagtttga agatgaagaa gaaagtcctg ttaatttccc catttactaa   7440
```

<210> SEQ ID NO 8
<211> LENGTH: 2479
<212> TYPE: PRT
<213> ORGANISM: Homo sapiens

<400> SEQUENCE: 8

```
Met Pro Pro Asn Ile Asn Trp Lys Glu Ile Met Lys Val Asp Pro Asp
1               5                   10                  15

Asp Leu Pro Arg Gln Glu Glu Leu Ala Asp Asn Leu Leu Ile Ser Leu
            20                  25                  30

Ser Lys Val Glu Val Asn Glu Leu Lys Ser Glu Lys Gln Glu Asn Val
        35                  40                  45

Ile His Leu Phe Arg Ile Thr Gln Ser Leu Met Lys Met Lys Ala Gln
    50                  55                  60

Glu Val Glu Leu Ala Leu Glu Glu Val Glu Lys Ala Gly Glu Glu Gln
65                  70                  75                  80

Ala Lys Phe Glu Asn Gln Leu Lys Thr Lys Val Met Lys Leu Glu Asn
                85                  90                  95

Glu Leu Glu Met Ala Gln Gln Ser Ala Gly Gly Arg Asp Thr Arg Phe
            100                 105                 110

Leu Arg Asn Glu Ile Cys Gln Leu Glu Lys Gln Leu Glu Gln Lys Asp
        115                 120                 125

Arg Glu Leu Glu Asp Met Glu Lys Glu Leu Glu Lys Glu Lys Lys Val
    130                 135                 140

Asn Glu Gln Leu Ala Leu Arg Asn Glu Glu Ala Glu Asn Glu Asn Ser
```

-continued

```
145                 150                 155                 160

Lys Leu Arg Arg Glu Asn Lys Arg Leu Lys Lys Lys Asn Glu Gln Leu
                165                 170                 175

Cys Gln Asp Ile Ile Asp Tyr Gln Lys Gln Ile Asp Ser Gln Lys Glu
            180                 185                 190

Thr Leu Leu Ser Arg Arg Gly Glu Asp Ser Asp Tyr Arg Ser Gln Leu
        195                 200                 205

Ser Lys Lys Asn Tyr Glu Leu Ile Gln Tyr Leu Asp Glu Ile Gln Thr
    210                 215                 220

Leu Thr Glu Ala Asn Glu Lys Ile Glu Val Gln Asn Gln Glu Met Arg
225                 230                 235                 240

Lys Asn Leu Glu Glu Ser Val Gln Glu Met Glu Lys Met Thr Asp Glu
                245                 250                 255

Tyr Asn Arg Met Lys Ala Ile Val His Gln Thr Asp Asn Val Ile Asp
            260                 265                 270

Gln Leu Lys Lys Glu Asn Asp His Tyr Gln Leu Gln Val Gln Glu Leu
        275                 280                 285

Thr Asp Leu Leu Lys Ser Lys Asn Glu Glu Asp Asp Pro Ile Met Val
    290                 295                 300

Ala Val Asn Ala Lys Val Glu Glu Trp Lys Leu Ile Leu Ser Ser Lys
305                 310                 315                 320

Asp Asp Glu Ile Ile Glu Tyr Gln Gln Met Leu His Asn Leu Arg Glu
                325                 330                 335

Lys Leu Lys Asn Ala Gln Leu Asp Ala Asp Lys Ser Asn Val Met Ala
            340                 345                 350

Leu Gln Gln Gly Ile Gln Glu Arg Asp Ser Gln Ile Lys Met Leu Thr
        355                 360                 365

Glu Gln Val Glu Gln Tyr Thr Lys Glu Met Glu Lys Asn Thr Cys Ile
    370                 375                 380

Ile Glu Asp Leu Lys Asn Glu Leu Gln Arg Asn Lys Gly Ala Ser Thr
385                 390                 395                 400

Leu Ser Gln Gln Thr His Met Lys Ile Gln Ser Thr Leu Asp Ile Leu
                405                 410                 415

Lys Glu Lys Thr Lys Glu Ala Glu Arg Thr Ala Glu Leu Ala Glu Ala
            420                 425                 430

Asp Ala Arg Glu Lys Asp Lys Glu Leu Val Glu Ala Leu Lys Arg Leu
        435                 440                 445

Lys Asp Tyr Glu Ser Gly Val Tyr Gly Leu Glu Asp Ala Val Val Glu
    450                 455                 460

Ile Lys Asn Cys Lys Asn Gln Ile Lys Ile Arg Asp Arg Glu Ile Glu
465                 470                 475                 480

Ile Leu Thr Lys Glu Ile Asn Lys Leu Glu Leu Lys Ile Ser Asp Phe
                485                 490                 495

Leu Asp Glu Asn Glu Ala Leu Arg Glu Arg Val Gly Leu Glu Pro Lys
            500                 505                 510

Thr Met Ile Asp Leu Thr Glu Phe Arg Asn Ser Lys His Leu Lys Gln
        515                 520                 525

Gln Gln Tyr Arg Ala Glu Asn Gln Ile Leu Leu Lys Glu Ile Glu Ser
    530                 535                 540

Leu Glu Glu Glu Arg Leu Asp Leu Lys Lys Lys Ile Arg Gln Met Ala
545                 550                 555                 560

Gln Glu Arg Gly Lys Arg Ser Ala Thr Ser Gly Leu Thr Thr Glu Asp
                565                 570                 575
```

-continued

```
Leu Asn Leu Thr Glu Asn Ile Ser Gln Gly Asp Arg Ile Ser Glu Arg
            580                 585                 590

Lys Leu Asp Leu Leu Ser Leu Lys Asn Met Ser Glu Ala Gln Ser Lys
        595                 600                 605

Asn Glu Phe Leu Ser Arg Glu Leu Ile Glu Lys Glu Arg Asp Leu Glu
    610                 615                 620

Arg Ser Arg Thr Val Ile Ala Lys Phe Gln Asn Lys Leu Lys Glu Leu
625                 630                 635                 640

Val Glu Glu Asn Lys Gln Leu Glu Glu Gly Met Lys Glu Ile Leu Gln
                645                 650                 655

Ala Ile Lys Glu Met Gln Lys Asp Pro Asp Val Lys Gly Gly Glu Thr
            660                 665                 670

Ser Leu Ile Ile Pro Ser Leu Glu Arg Leu Val Asn Ala Ile Glu Ser
        675                 680                 685

Lys Asn Ala Glu Gly Ile Phe Asp Ala Ser Leu His Leu Lys Ala Gln
    690                 695                 700

Val Asp Gln Leu Thr Gly Arg Asn Glu Glu Leu Arg Gln Glu Leu Arg
705                 710                 715                 720

Glu Ser Arg Lys Glu Ala Ile Asn Tyr Ser Gln Gln Leu Ala Lys Ala
                725                 730                 735

Asn Leu Lys Ile Asp His Leu Glu Lys Glu Thr Ser Leu Leu Arg Gln
            740                 745                 750

Ser Glu Gly Ser Asn Val Val Phe Lys Gly Ile Asp Leu Pro Asp Gly
        755                 760                 765

Ile Ala Pro Ser Ser Ala Ser Ile Ile Asn Ser Gln Asn Glu Tyr Leu
    770                 775                 780

Ile His Leu Leu Gln Glu Leu Glu Asn Lys Glu Lys Lys Leu Lys Asn
785                 790                 795                 800

Leu Glu Asp Ser Leu Glu Asp Tyr Asn Arg Lys Phe Ala Val Ile Arg
                805                 810                 815

His Gln Gln Ser Leu Leu Tyr Lys Glu Tyr Leu Ser Glu Lys Glu Thr
            820                 825                 830

Trp Lys Thr Glu Ser Lys Thr Ile Lys Glu Glu Lys Arg Lys Leu Glu
        835                 840                 845

Asp Gln Val Gln Gln Asp Ala Ile Lys Val Lys Glu Tyr Asn Asn Leu
    850                 855                 860

Leu Asn Ala Leu Gln Met Asp Ser Asp Glu Met Lys Lys Ile Leu Ala
865                 870                 875                 880

Glu Asn Ser Arg Lys Ile Thr Val Leu Gln Val Asn Glu Lys Ser Leu
                885                 890                 895

Ile Arg Gln Tyr Thr Thr Leu Val Glu Leu Glu Arg Gln Leu Arg Lys
            900                 905                 910

Glu Asn Glu Lys Gln Lys Asn Glu Leu Leu Ser Met Glu Ala Glu Val
        915                 920                 925

Cys Glu Lys Ile Gly Cys Leu Gln Arg Phe Lys Glu Met Ala Ile Phe
    930                 935                 940

Lys Ile Ala Ala Leu Gln Lys Val Val Asp Asn Ser Val Ser Leu Ser
945                 950                 955                 960

Glu Leu Glu Leu Ala Asn Lys Gln Tyr Asn Glu Leu Thr Ala Lys Tyr
                965                 970                 975

Arg Asp Ile Leu Gln Lys Asp Asn Met Leu Val Gln Arg Thr Ser Asn
            980                 985                 990
```

-continued

```
Leu Glu His Leu Glu Cys Glu Asn  Ile Ser Leu Lys Glu  Gln Val Glu
        995                 1000                 1005

Ser Ile  Asn Lys Glu Leu Glu  Ile Thr Lys Glu Lys  Leu His Thr
    1010                 1015                 1020

Ile Glu  Gln Ala Trp Glu Gln  Glu Thr Lys Leu Gly  Asn Glu Ser
    1025                 1030                 1035

Ser Met  Asp Lys Ala Lys Lys  Ser Ile Thr Asn Ser  Asp Ile Val
    1040                 1045                 1050

Ser Ile  Ser Lys Lys Ile Thr  Met Leu Glu Met Lys  Glu Leu Asn
    1055                 1060                 1065

Glu Arg  Gln Arg Ala Glu His  Cys Gln Lys Met Tyr  Glu His Leu
    1070                 1075                 1080

Arg Thr  Ser Leu Lys Gln Met  Glu Glu Arg Asn Phe  Glu Leu Glu
    1085                 1090                 1095

Thr Lys  Phe Ala Glu Leu Thr  Lys Ile Asn Leu Asp  Ala Gln Lys
    1100                 1105                 1110

Val Glu  Gln Met Leu Arg Asp  Glu Leu Ala Asp Ser  Val Ser Lys
    1115                 1120                 1125

Ala Val  Ser Asp Ala Asp Arg  Gln Arg Ile Leu Glu  Leu Glu Lys
    1130                 1135                 1140

Asn Glu  Met Glu Leu Lys Val  Glu Val Ser Lys Leu  Arg Glu Ile
    1145                 1150                 1155

Ser Asp  Ile Ala Arg Arg Gln  Val Glu Ile Leu Asn  Ala Gln Gln
    1160                 1165                 1170

Gln Ser  Arg Asp Lys Glu Val  Glu Ser Leu Arg Met  Gln Leu Leu
    1175                 1180                 1185

Asp Tyr  Gln Ala Gln Ser Asp  Glu Lys Ser Leu Ile  Ala Lys Leu
    1190                 1195                 1200

His Gln  His Asn Val Ser Leu  Gln Leu Ser Glu Ala  Thr Ala Leu
    1205                 1210                 1215

Gly Lys  Leu Glu Ser Ile Thr  Ser Lys Leu Gln Lys  Met Glu Ala
    1220                 1225                 1230

Tyr Asn  Leu Arg Leu Glu Gln  Lys Leu Asp Glu Lys  Glu Gln Ala
    1235                 1240                 1245

Leu Tyr  Tyr Ala Arg Leu Glu  Gly Arg Asn Arg Ala  Lys His Leu
    1250                 1255                 1260

Arg Gln  Thr Ile Gln Ser Leu  Arg Arg Gln Phe Ser  Gly Ala Leu
    1265                 1270                 1275

Pro Leu  Ala Gln Gln Glu Lys  Phe Ser Lys Thr Met  Ile Gln Leu
    1280                 1285                 1290

Gln Asn  Asp Lys Leu Lys Ile  Met Gln Glu Met Lys  Asn Ser Gln
    1295                 1300                 1305

Gln Glu  His Arg Asn Met Glu  Asn Lys Thr Leu Glu  Met Glu Leu
    1310                 1315                 1320

Lys Leu  Lys Gly Leu Glu Glu  Leu Ile Ser Thr Leu  Lys Asp Thr
    1325                 1330                 1335

Lys Gly  Ala Gln Lys Val Ile  Asn Trp His Met Lys  Ile Glu Glu
    1340                 1345                 1350

Leu Arg  Leu Gln Glu Leu Lys  Leu Asn Arg Glu Leu  Val Lys Asp
    1355                 1360                 1365

Lys Glu  Glu Ile Lys Tyr Leu  Asn Asn Ile Ile Ser  Glu Tyr Glu
    1370                 1375                 1380

Arg Thr  Ile Ser Ser Leu Glu  Glu Glu Ile Val Gln  Gln Asn Lys
```

```
    1385                1390                1395

Phe His  Glu Glu Arg Gln Met  Ala Trp Asp Gln Arg  Glu Val Asp
    1400                1405                1410

Leu Glu  Arg Gln Leu Asp Ile  Phe Asp Arg Gln Gln  Asn Glu Ile
    1415                1420                1425

Leu Asn  Ala Ala Gln Lys Phe  Glu Glu Ala Thr Gly  Ser Ile Pro
    1430                1435                1440

Asp Pro  Ser Leu Pro Leu Pro  Asn Gln Leu Glu Ile  Ala Leu Arg
    1445                1450                1455

Lys Ile  Lys Glu Asn Ile Arg  Ile Ile Leu Glu Thr  Arg Ala Thr
    1460                1465                1470

Cys Lys  Ser Leu Glu Glu Lys  Leu Lys Glu Lys Glu  Ser Ala Leu
    1475                1480                1485

Arg Leu  Ala Glu Gln Asn Ile  Leu Ser Arg Asp Lys  Val Ile Asn
    1490                1495                1500

Glu Leu  Arg Leu Arg Leu Pro  Ala Thr Ala Glu Arg  Glu Lys Leu
    1505                1510                1515

Ile Ala  Glu Leu Gly Arg Lys  Glu Met Glu Pro Lys  Ser His His
    1520                1525                1530

Thr Leu  Lys Ile Ala His Gln  Thr Ile Ala Asn Met  Gln Ala Arg
    1535                1540                1545

Leu Asn  Gln Lys Glu Glu Val  Leu Lys Lys Tyr Gln  Arg Leu Leu
    1550                1555                1560

Glu Lys  Ala Arg Glu Glu Gln  Arg Glu Ile Val Lys  Lys His Glu
    1565                1570                1575

Glu Asp  Leu His Ile Leu His  His Arg Leu Glu Leu  Gln Ala Asp
    1580                1585                1590

Ser Ser  Leu Asn Lys Phe Lys  Gln Thr Ala Trp Asp  Leu Met Lys
    1595                1600                1605

Gln Ser  Pro Thr Pro Val Pro  Thr Asn Lys His Phe  Ile Arg Leu
    1610                1615                1620

Ala Glu  Met Glu Gln Thr Val  Ala Glu Gln Asp Asp  Ser Leu Ser
    1625                1630                1635

Ser Leu  Leu Val Lys Leu Lys  Lys Val Ser Gln Asp  Leu Glu Arg
    1640                1645                1650

Gln Arg  Glu Ile Thr Glu Leu  Lys Val Lys Glu Phe  Glu Asn Ile
    1655                1660                1665

Lys Leu  Gln Leu Gln Glu Asn  His Glu Asp Glu Val  Lys Lys Val
    1670                1675                1680

Lys Ala  Glu Val Glu Asp Leu  Lys Tyr Leu Leu Asp  Gln Ser Gln
    1685                1690                1695

Lys Glu  Ser Gln Cys Leu Lys  Ser Glu Leu Gln Ala  Gln Lys Glu
    1700                1705                1710

Ala Asn  Ser Arg Ala Pro Thr  Thr Thr Met Arg Asn  Leu Val Glu
    1715                1720                1725

Arg Leu  Lys Ser Gln Leu Ala  Leu Lys Glu Lys Gln  Gln Lys Ala
    1730                1735                1740

Leu Ser  Arg Ala Leu Leu Glu  Leu Arg Ala Glu Met  Thr Ala Ala
    1745                1750                1755

Ala Glu  Glu Arg Ile Ile Ser  Ala Thr Ser Gln Lys  Glu Ala His
    1760                1765                1770

Leu Asn  Val Gln Gln Ile Val  Asp Arg His Thr Arg  Glu Leu Lys
    1775                1780                1785
```

```
Thr Gln  Val Glu Asp Leu Asn  Glu Asn Leu Leu Lys  Leu Lys Glu
    1790                 1795                 1800

Ala Leu  Lys Thr Ser Lys Asn  Arg Glu Asn Ser Leu  Thr Asp Asn
    1805                 1810                 1815

Leu Asn  Asp Leu Asn Asn Glu  Leu Gln Lys Lys Gln  Lys Ala Tyr
    1820                 1825                 1830

Asn Lys  Ile Leu Arg Glu Lys  Glu Glu Ile Asp Gln  Glu Asn Asp
    1835                 1840                 1845

Glu Leu  Lys Arg Gln Ile Lys  Arg Leu Thr Ser Gly  Leu Gln Gly
    1850                 1855                 1860

Lys Pro  Leu Thr Asp Asn Lys  Gln Ser Leu Ile Glu  Glu Leu Gln
    1865                 1870                 1875

Arg Lys  Val Lys Lys Leu Glu  Asn Gln Leu Glu Gly  Lys Val Glu
    1880                 1885                 1890

Glu Val  Asp Leu Lys Pro Met  Lys Glu Lys Asn Ala  Lys Glu Glu
    1895                 1900                 1905

Leu Ile  Arg Trp Glu Glu Gly  Lys Lys Trp Gln Ala  Lys Ile Glu
    1910                 1915                 1920

Gly Ile  Arg Asn Lys Leu Lys  Glu Lys Glu Gly Glu  Val Phe Thr
    1925                 1930                 1935

Leu Thr  Lys Gln Leu Asn Thr  Leu Lys Asp Leu Phe  Ala Lys Ala
    1940                 1945                 1950

Asp Lys  Glu Lys Leu Thr Leu  Gln Arg Lys Leu Lys  Thr Thr Gly
    1955                 1960                 1965

Met Thr  Val Asp Gln Val Leu  Gly Ile Arg Ala Leu  Glu Ser Glu
    1970                 1975                 1980

Lys Glu  Leu Glu Glu Leu Lys  Lys Arg Asn Leu Asp  Leu Glu Asn
    1985                 1990                 1995

Asp Ile  Leu Tyr Met Arg Ala  His Gln Ala Leu Pro  Arg Asp Ser
    2000                 2005                 2010

Val Val  Glu Asp Leu His Leu  Gln Asn Arg Tyr Leu  Gln Glu Lys
    2015                 2020                 2025

Leu His  Ala Leu Glu Lys Gln  Phe Ser Lys Asp Thr  Tyr Ser Lys
    2030                 2035                 2040

Pro Ser  Ile Ser Gly Ile Glu  Ser Asp Asp His Cys  Gln Arg Glu
    2045                 2050                 2055

Gln Glu  Leu Gln Lys Glu Asn  Leu Lys Leu Ser Ser  Glu Asn Ile
    2060                 2065                 2070

Glu Leu  Lys Phe Gln Leu Glu  Gln Ala Asn Lys Asp  Leu Pro Arg
    2075                 2080                 2085

Leu Lys  Asn Gln Val Arg Asp  Leu Lys Glu Met Cys  Glu Phe Leu
    2090                 2095                 2100

Lys Lys  Glu Lys Ala Glu Val  Gln Arg Lys Leu Gly  His Val Arg
    2105                 2110                 2115

Gly Ser  Gly Arg Ser Gly Lys  Thr Ile Pro Glu Leu  Glu Lys Thr
    2120                 2125                 2130

Ile Gly  Leu Met Lys Lys Val  Val Glu Lys Val Gln  Arg Glu Asn
    2135                 2140                 2145

Glu Gln  Leu Lys Lys Ala Ser  Gly Ile Leu Thr Ser  Glu Lys Met
    2150                 2155                 2160

Ala Asn  Ile Glu Gln Glu Asn  Glu Lys Leu Lys Ala  Glu Leu Glu
    2165                 2170                 2175
```

-continued

```
Lys Leu  Lys Ala His Leu Gly  His Gln Leu Ser Met  His Tyr Glu
    2180                 2185                 2190

Ser Lys  Thr Lys Gly Thr Glu  Lys Ile Ile Ala Glu  Asn Glu Arg
    2195                 2200                 2205

Leu Arg  Lys Glu Leu Lys Lys  Glu Thr Asp Ala Ala  Glu Lys Leu
    2210                 2215                 2220

Arg Ile  Ala Lys Asn Asn Leu  Glu Ile Leu Asn Glu  Lys Met Thr
    2225                 2230                 2235

Val Gln  Leu Glu Glu Thr Gly  Lys Arg Leu Gln Phe  Ala Glu Ser
    2240                 2245                 2250

Arg Gly  Pro Gln Leu Glu Gly  Ala Asp Ser Lys Ser  Trp Lys Ser
    2255                 2260                 2265

Ile Val  Val Thr Arg Met Tyr  Glu Thr Lys Leu Lys  Glu Leu Glu
    2270                 2275                 2280

Thr Asp  Ile Ala Lys Lys Asn  Gln Ser Ile Thr Asp  Leu Lys Gln
    2285                 2290                 2295

Leu Val  Lys Glu Ala Thr Glu  Arg Glu Gln Lys Val  Asn Lys Tyr
    2300                 2305                 2310

Asn Glu  Asp Leu Glu Gln Gln  Ile Lys Ile Leu Lys  His Val Pro
    2315                 2320                 2325

Glu Gly  Ala Glu Thr Glu Gln  Gly Leu Lys Arg Glu  Leu Gln Val
    2330                 2335                 2340

Leu Arg  Leu Ala Asn His Gln  Leu Asp Lys Glu Lys  Ala Glu Leu
    2345                 2350                 2355

Ile His  Gln Ile Glu Ala Asn  Lys Asp Gln Ser Gly  Ala Glu Ser
    2360                 2365                 2370

Thr Ile  Pro Asp Ala Asp Gln  Leu Lys Glu Lys Ile  Lys Asp Leu
    2375                 2380                 2385

Glu Thr  Gln Leu Lys Met Ser  Asp Leu Glu Lys Gln  His Leu Lys
    2390                 2395                 2400

Glu Glu  Ile Lys Lys Leu Lys  Lys Glu Leu Glu Asn  Phe Asp Pro
    2405                 2410                 2415

Ser Phe  Phe Glu Glu Ile Glu  Asp Leu Lys Tyr Asn  Tyr Lys Glu
    2420                 2425                 2430

Glu Val  Lys Lys Asn Ile Leu  Leu Glu Glu Lys Val  Lys Lys Leu
    2435                 2440                 2445

Ser Glu  Gln Leu Gly Val Glu  Leu Thr Ser Pro Val  Ala Ala Ser
    2450                 2455                 2460

Glu Glu  Phe Glu Asp Glu Glu  Glu Ser Pro Val Asn  Phe Pro Ile
    2465                 2470                 2475

Tyr
```

<210> SEQ ID NO 9
<211> LENGTH: 7440
<212> TYPE: DNA
<213> ORGANISM: Homo sapiens

<400> SEQUENCE: 9

```
ttagtaaatg gggaaattaa caggactttc ttcttcatct tcaaactctt cagaagcagc      60

aacagggcta gttaattcaa ctcccaattg ttctgaaagt ttttttacct tctcttctaa     120

gagaatattc ttcttcactt cttccttgta attatactta agatcttcaa tttcttcaaa     180

aaatgaagga tcaaaatttt ccagttcttt tttcagcttc tttatttcct ccttcaaatg     240

ctgcttttct agatctgaca ttttgagctg tgtctctaga tcttttattt tttcctttag     300
```

-continued

```
ttgatcagca tcaggtatgg tgctttcagc tccactttgg tccttgttag cttctatctg    360
atggattaat tctgctttct ctttatccag ctgatgatta gctaatctaa gaacttgaag    420
ctcccgttta aggccttgct ctgtctcagc accttcagga acatgtttaa gaatcttaat    480
ctgttgttca aggtcttcat tgtatttgtt aactttttgt tctctctctg ttgcttcttt    540
tacaagctgt ttaaggtcag taatgctttg atttttttg gcaatatcag tttccaattc    600
ttttaacttg gtttcataca ttcttgtaac cacaatggat ttccagctct tactgtcagc    660
accttcaagc tgtggacctc tgctttctgc aaactgcaat ctcttaccag tctcttctag    720
ttgaactgtc atcttctcat ttaatatctc taaattattc tttgctatcc gtaatttctc    780
tgcagcatca gtttcttttt taagttcttt acgaagcctt tcattttcag caataatttt    840
ttctgtgcct ttggtcttgg attcatagtg catgctcaac tgatgcccaa gatgagcttt    900
aagtttttct aattcagcct tcaatttttc attttcctgc tcaatattag ccatttttc    960
actagtcaat attcctgatg ctttttcaa ctgttcattt tctctctgga cttttcaac   1020
tactttttc attaaaccaa tggtttttc cagttctggg attgtctttc cacttctacc   1080
agaccctcta acatggccaa gtttccgctg aacttctgct ttttctttct taagaaattc   1140
acacatttcc ttcaaatctc tgacttgatt ctttaatctt ggcaaatctt tatttgcttg   1200
ttcaagctga aatttcagtt caatattttc agatgacaac ttcaagtttt ccttctgaag   1260
ctcctgttct ctctgacaat gatcatctga ctctattcct gaaattgaag gcttagaata   1320
tgtatccttt gaaaactgtt tttctaaagc atgaagtttt tcttggaggt atctattttg   1380
taaatgtaaa tcttctacaa cagaatctcg aggaagagct tggtgggccc tcatatacaa   1440
tatatcattt tctaagtcaa gatttctctt ttttaattct tccaattctt tttctgactc   1500
caaagctcgt attcccaaaa cctgatcaac agtcatgcca gttgttttta gtttcctctg   1560
caaagtaagt ttctctttat cggctttggc aaaaagatcc ttcaaagtat tcaactgctt   1620
tgttaaagta aagacttccc cctctttctc ttttaacttg tttcgaattc cttctatttt   1680
ggcttgccac tttttacctt cttcccacct aattaattct tctttagcat tcttttcttt   1740
cataggtttt aggtctactt cctccacctt tccctctaat tggttctcta gtttttaac   1800
tttcctttgg agttcttcaa ttagactttg tttattatct gtcaggggtt tgccctgtaa   1860
tccactggtt agtcttttaa tttgcctttt cagttcatca ttctcttgat caatttcctc   1920
tttctctcta agtattttat tataggcttt ttgtttcttt tgcagttcat tatttaagtc   1980
attcaaatta tcagttagtg agttttctct gtttttactt gttttaagtg cttctttcaa   2040
ttttaaaaga ttttcattta aatcttcaac ttgtgtcttt agctctctag tatgtcgatc   2100
aacgatttgt tgaacattga gatgggcctc tttttgagaa gttgcagaaa taatacgttc   2160
ttcagcagct gctgtcattt ctgcccggag ttctaaaagt gcccgactaa gtgctttctg   2220
ttgtttctcc ttcaaggcta attggctctt tagccgttct actagatttc tcattgtagt   2280
tgttggagct cttgaatttg cttctttttg agcctgaagt tcagatttta aacactgtga   2340
ctccttttgt gactggtcca gaagatactt taaatcctct acttccgctt ttactttttt   2400
cacttcatct tcatggtttt cttgaagctg taatttgata ttttcaaatt cttttacttt   2460
taattcagtg atttctcttt gtctctccaa atcttgtgat actttcttta gtttgaccaa   2520
gagtgaggaa agagagtcat cttgttctgc tactgtctgt tccatctcag ccagacgaat   2580
aaaatgcttg ttggtaggaa ctggagtggg agactgtttc attaaatccc aagccgtttg   2640
```

-continued

```
tttgaattta tttagtgaac tatcagcctg tagttctaat ctgtgatgaa gaatatgaag   2700
gtcttcctca tgtttcttca caatttctct ttgctcctct ctggcttttt ctagaagacg   2760
ttgatacttc tttaatactt cttcttttg atttaacctt gcttgcatgt ttgcaatggt   2820
ttgatgagca attttcaatg tgtggtgaga ttttggttcc atctcttttc tgcctagctc   2880
agctatgagc ttttctcttt ctgcagtggc aggcaatcga agcctcagtt cattgattac   2940
tttgtctctt gacagtatat tttgttctgc taaccttaaa gcagattctt tctcttttag   3000
tttctcttct agtgatttgc aagttgcccg tgtttctaga attattcgaa tgttctcctt   3060
aattttcctt agagcgatct caagttgatt tggaaggggc aaactagggt cagggattga   3120
tcctgtagct tcttcaaact tttgtgccgc atttagtatt tcattttgct gacggtcaaa   3180
aatgtctagt tggcgttcca ggtcaacttc tctttgatcc caggccattt gtctttcttc   3240
atgaaacttg ttctgttgca caatttcttc ttcaagactg ctgattgtac gttcatattc   3300
agaaattatg ttattcaaat atttatttc ttctttatcc ttgactaatt cccgatttag   3360
tttaagttct tgaagacgaa gttcttctat tttcatatgc cagttgatta cctttgggc   3420
tcctttggta tcctttaaag tgcttattaa ctcttccagg ccctttaatt ttaattccat   3480
ctccaatgtt ttgttctcca tatttctatg ttcttgttga gaatttttca tttcttgcat   3540
tatcttaagt ttgtcatttt gtagttgaat cattgttttg gagaactttt cctgttgtgc   3600
caagggtaaa gctccactaa actgtcgtcg tagagactga attgtttggc gcagatgttt   3660
tgctctgttt cttccctcca aacgagcata atagagagcc tgttcttttt catcaagttt   3720
ctgctctaag cgcaagttgt aggcctccat cttctgcagt ttagatgtaa ttgactccaa   3780
cttaccaaga gcagtagcct cactcagttg aagagagaca ttatgttggt gcaacttggc   3840
aatgagcgac ttttcatcag actgtgcctg atagtctagc agttgcattc tgagggactc   3900
tacttccttg tccctagatt gttgttgtgc attcaaaatt tcaacttgtc ttctggcaat   3960
atcagaaatc tctctcagtt ttgacacttc aacttttagt tccatttcat tcttctctaa   4020
ttctagaatc cgttgcctat cagcatcact tactgccttg ctcacactat cagctaattc   4080
atctcttaac atctgttcca ccttctgtgc atccaaattg attttggtaa gctcagcaaa   4140
tttggtttcc aattcaaaat tacgttcctc catttgcttt aacgaagtcc gtaagtgttc   4200
atacattttt tgacaatgtt cagcccgctg cctttcattt aattccttca tttccagcat   4260
agttattttt tttgaaatgg aaacaatgtc actgttggtt attgatttct ttgccttatc   4320
catgctagat tcattaccta atttagtttc ctgttcccag gcttgttcaa tagtgtgaag   4380
tttttccttg gtaatctcca gttctttatt tatagactcc acttgttctt ttaaggagat   4440
gttttcacac tccaggtgtt ccaagttact tgttctttga acaagcatat tatcttttg   4500
caagatgtcc ctgtacttag cagtcagttc attgtactgt ttattagcca gttctagttc   4560
agacaaagaa acactattat ctacaacttt ttggagagct gcaatcttga aaatggccat   4620
ttccttaaat ctttgcaaac acccaatttt ttcacaaact tcagcctcca ttgacaacaa   4680
ttcattcttt tgcttctcat tttcttttct aagttgtcgc tccaattcta ctaaggttgt   4740
atattgcctt ataagtgatt tttcattcac ttgcaaaaca gtaattttcc tactattttc   4800
tgcaagtatt tttttcattt catccgaatc catctgaaga gcattgagca aattattata   4860
ttcttttact tttatagcat cttgttggac ttgatcctca agttttctct tttcctcttt   4920
tattgtttta gattctgttt tccaggtctc cttttcactt aggtattctt tatacaacaa   4980
actttgttga tgacgaatta cagcaaattt tctgttgtaa tcttcaagag aatcttctaa   5040
```

-continued

```
attctttaac ttttttttctt tattttctag ttcctgtaac aaatgtatta aatattcatt   5100
ctgagaatta atgatactgg cactagatgg tgctatccca tcaggtaagt caattccttt   5160
aaaaacaaca ttcgatcctt ctgattgtcg taaaagacta gtttcttttt caagatggtc   5220
tatctttaaa ttagcttttg ccaactgctg tgaataattt atagcctctt tccgagattc   5280
cctgagctcc tgtcttaatt cttcatttct tccggtaagc tgatcaactt gggctttcaa   5340
atgcagactc gcatcaaaga ttccttctgc attctttgat tctatagcat taactagtct   5400
ttcaaggcta gggataatta gagatgtttc tcctccttta acatcaggat ctttctgcat   5460
ttccttaatt gcttgcaata tttctttcat accttcttca agttgcttat tttcttcaac   5520
taattctttt aatttattct gaaatttggc tatcactgtc ctactccttt ctaaatctct   5580
ttctttttca attagttctc ttgaaagaaa ttcattcttt gattgtgctt cactcatatt   5640
tttgaggctc aataaatcca attttctttc acttattcta tctccttgag aaatgttttc   5700
agttaggttc aggtcctcag tggttaatcc tgaagttgca cttctttttc ctctttcttg   5760
agccatttga cgaatttttt ttttcagatc aagtcgttct tcctctagac tttcaatctc   5820
tttcaaaaga atctggtttt cagctctgta ctgctgctgt tttaagtgtt tgctatttct   5880
aaattcagtt aaatcaatca ttgtctttgg ttcaaggccc acacgctctc taagtgcctc   5940
attttcatca aggaaatcac tgatcttcaa ttcaagttta ttgatttcct ttgttaatat   6000
ttcaatctct cgatctctta ttttaatttg gtttttacaa ttctttattt caacgacagc   6060
atcttctaaa ccatatactc ccgattcata atcttttaac ctcttcagag cctcaactaa   6120
ttctttatcc ttttccctag catcagcctc agccagttca gctgttctct cagcctcttt   6180
agttttctct tttaaaatgt ctaacgttga ctgaattttc atatgagtct gttgagaaag   6240
ggttgaagca cctttgtttc tttggagctc atttttcaaa tcttcaataa tacaagtatt   6300
cttttccatt tcttttgtat attgttctac ttgttcggtg agcatcttaa tttgactgtc   6360
tcgttcctgt ataccctgct gtagagccat aacattactt ttatcagcat caagctgagc   6420
attcttaagt ttctccctta ggttatgtaa catttgctga tactcaataa tttcatcatc   6480
tttagaagac aaaattagct tccattcttc tacttttgca ttgacagcta ccataattgg   6540
atcatcttct tcatttttttg atttcagaag atctgtaagc tcctgcactt gaagttgata   6600
atgatcgttt tcttttttta actgatctat tacattatct gtctgatgca caatagcttt   6660
cattctatta tattcatcag tcatcttctc catttcctgt acagactctt ctaaattttt   6720
tctcatttct tgattctgaa cttcaatttt ctcattagct tctgttaaag tctgaatttc   6780
atcaagatat tggataagct catagttttt tttagacaac tgtgatcggt agtcactgtc   6840
ttcccctctt cttgataaaa gtgtttcttt ctgtgaatct atttgtttct ggtagtcaat   6900
aatatcctga caaagttgtt cattcttttt ctttagacgt ttgttctctc ttcttaattt   6960
gctgttttca ttttctgcct cctcatttcg aagagccaat tgctcattaa ctttcttctc   7020
tttctccaac tccttttcca tgtcctccaa ttctctatct ttttgttcta attgtttttc   7080
aagttggcaa atttcattac gtaaaaaccg agtatctcgt ccacctgcag actgctgagc   7140
catctccagt tcattttcca gtttcattac tttagttttt aattgatttt caaattttgc   7200
ttgttcttct ccagcttttt ctacttcttc caaagccagc tccacttctt gagctttcat   7260
cttcattagt gactgagtaa ttctgaaaag gtgtatcaca ttttcttgct tttcactttt   7320
tagctcattt acttccacct tggataagga aatcaataaa ttatctgcca gttcttcttg   7380
```

acggggcagg tcatctgggt caactttcat tatttctttc cagtttatat taggtggcat 7440

<210> SEQ ID NO 10
<211> LENGTH: 2973
<212> TYPE: DNA
<213> ORGANISM: Homo sapiens

<400> SEQUENCE: 10
ttagcagaac aaaatatact gtcaagagac aaagtaatca atgaactgag gcttcgattg 60
cctgccactg cagaaagaga aaagctcata gctgagctag gcagaaaaga gatggaacca 120
aaatctcacc acacattgaa aattgctcat caaaccattg caaacatgca agcaaggtta 180
aatcaaaaag aagaagtatt aaagaagtat caacgtcttc tagaaaaagc cagagaggag 240
caaagagaaa ttgtgaagaa acatgaggaa gaccttcata ttcttcatca cagattagaa 300
ctacaggctg atagttcact aaataaattc aaacaaacgg cttgggattt aatgaaacag 360
tctcccactc cagttcctac caacaagcat tttattcgtc tggctgagat ggaacagaca 420
gtagcagaac aagatgactc tctttcctca ctcttggtca aactaaagaa agtatcacaa 480
gatttggaga gacaaagaga aatcactgaa ttaaaagtaa aagaatttga aaatatcaaa 540
ttacagcttc aagaaaacca tgaagatgaa gtgaaaaaag taaaagcgga agtagaggat 600
ttaaagtatc ttctggacca gtcacaaaag gagtcacagt gtttaaaatc tgaacttcag 660
gctcaaaaag aagcaaattc aagagctcca acaactacaa tgagaaatct agtagaacgg 720
ctaaagagcc aattagcctt gaaggagaaa caacagaaag cacttagtcg ggcactttta 780
gaactccggg cagaaatgac agcagctgct gaagaacgta ttatttctgc aacttctcaa 840
aaagaggccc atctcaatgt tcaacaaatc gttgatcgac atactagaga gctaaagaca 900
caagttgaag atttaaatga aaatctttta aaattgaaag aagcacttaa aacaagtaaa 960
aacagagaaa actcactaac tgataatttg aatgacttaa ataatgaact gcaaaagaaa 1020
caaaaagcct ataataaaat acttagagag aaagaggaaa ttgatcaaga gaatgatgaa 1080
ctgaaaaggc aaattaaaag actaaccagt ggattacagg gcaaacccct gacagataat 1140
aaacaaagtc taattgaaga actccaaagg aaagttaaaa aactagagaa ccaattagag 1200
ggaaaggtgg aggaagtaga cctaaaacct atgaaagaaa agaatgctaa agaagaatta 1260
attaggtggg aagaaggtaa aaagtggcaa gccaaaatag aaggaattcg aaacaagtta 1320
aaagagaaag agggggaagt ctttacttta acaaagcagt tgaatacttt gaaggatctt 1380
tttgccaaag ccgataaaga gaaacttact ttgcagagga aactaaaaac aactggcatg 1440
actgttgatc aggttttggg aatacgagct ttggagtcag aaaaagaatt ggaagaatta 1500
aaaaagagaa atcttgactt agaaaatgat atattgtata tgagggccca ccaagctctt 1560
cctcgagatt ctgttgtaga agatttacat ttacaaaata gatacctcca agaaaaactt 1620
catgctttag aaaaacagtt ttcaaaggat acatattcta agccttcaat ttcaggaata 1680
gagtcagatg atcattgtca gagagaacag gagcttcaga aggaaaactt gaagttgtca 1740
tctgaaaata ttgaactgaa atttcagctt gaacaagcaa ataaagattt gccaagatta 1800
aagaatcaag tcagagattt gaaggaaatg tgtgaatttc ttaagaaaga aaaagcagaa 1860
gttcagcgga aacttggcca tgttagaggg tctggtagaa gtggaaagac aatcccagaa 1920
ctggaaaaaa ccattggttt aatgaaaaaa gtagttgaaa aagtccagag agaaaatgaa 1980
cagttgaaaa aagcatcagg aatattgact agtgaaaaaa tggctaatat tgagcaggaa 2040
aatgaaaaat tgaaggctga attagaaaaa cttaaagctc atcttgggca tcagttgagc 2100

-continued

```
atgcactatg aatccaagac caaaggcaca gaaaaaatta ttgctgaaaa tgaaaggctt   2160

cgtaaagaac ttaaaaaaga aactgatgct gcagagaaat tacggatagc aaagaataat   2220

ttagagatat taaatgagaa gatgacagtt caactagaag agactggtaa gagattgcag   2280

tttgcagaaa gcagaggtcc acagcttgaa ggtgctgaca gtaagagctg gaaatccatt   2340

gtggttacaa gaatgtatga aaccaagtta aaagaattgg aaactgatat tgccaaaaaa   2400

aatcaaagca ttactgacct taaacagctt gtaaaagaag caacagagag agaacaaaaa   2460

gttaacaaat acaatgaaga ccttgaacaa cagattaaga ttcttaaaca tgttcctgaa   2520

ggtgctgaga cagagcaagg ccttaaacgg gagcttcaag ttcttagatt agctaatcat   2580

cagctggata aagagaaagc agaattaatc catcagatag aagctaacaa ggaccaaagt   2640

ggagctgaaa gcaccatacc tgatgctgat caactaaagg aaaaaataaa agatctagag   2700

acacagctca aaatgtcaga tctagaaaag cagcatttga aggaggaaat aaagaagctg   2760

aaaaaagaac tggaaaattt tgatccttca ttttttgaag aaattgaaga tcttaagtat   2820

aattacaagg aagaagtgaa gaagaatatt ctcttagaag agaaggtaaa aaaactttca   2880

gaacaattgg gagttgaatt aactagccct gttgctgctt ctgaagagtt tgaagatgaa   2940

gaagaaagtc ctgttaattt ccccatttac taa                                2973
```

<210> SEQ ID NO 11
<211> LENGTH: 990
<212> TYPE: PRT
<213> ORGANISM: Homo sapiens

<400> SEQUENCE: 11

```
Leu Ala Glu Gln Asn Ile Leu Ser Arg Asp Lys Val Ile Asn Glu Leu
1               5                   10                  15

Arg Leu Arg Leu Pro Ala Thr Ala Glu Arg Glu Lys Leu Ile Ala Glu
            20                  25                  30

Leu Gly Arg Lys Glu Met Glu Pro Lys Ser His His Thr Leu Lys Ile
        35                  40                  45

Ala His Gln Thr Ile Ala Asn Met Gln Ala Arg Leu Asn Gln Lys Glu
    50                  55                  60

Glu Val Leu Lys Lys Tyr Gln Arg Leu Leu Glu Lys Ala Arg Glu Glu
65                  70                  75                  80

Gln Arg Glu Ile Val Lys Lys His Glu Glu Asp Leu His Ile Leu His
                85                  90                  95

His Arg Leu Glu Leu Gln Ala Asp Ser Ser Leu Asn Lys Phe Lys Gln
            100                 105                 110

Thr Ala Trp Asp Leu Met Lys Gln Ser Pro Thr Pro Val Pro Thr Asn
        115                 120                 125

Lys His Phe Ile Arg Leu Ala Glu Met Glu Gln Thr Val Ala Glu Gln
    130                 135                 140

Asp Asp Ser Leu Ser Ser Leu Leu Val Lys Leu Lys Lys Val Ser Gln
145                 150                 155                 160

Asp Leu Glu Arg Gln Arg Glu Ile Thr Glu Leu Lys Val Lys Glu Phe
                165                 170                 175

Glu Asn Ile Lys Leu Gln Leu Gln Glu Asn His Glu Asp Glu Val Lys
            180                 185                 190

Lys Val Lys Ala Glu Val Glu Asp Leu Lys Tyr Leu Leu Asp Gln Ser
        195                 200                 205

Gln Lys Glu Ser Gln Cys Leu Lys Ser Glu Leu Gln Ala Gln Lys Glu
```

-continued

```
    210                 215                 220

Ala Asn Ser Arg Ala Pro Thr Thr Thr Met Arg Asn Leu Val Glu Arg
225                 230                 235                 240

Leu Lys Ser Gln Leu Ala Leu Lys Glu Lys Gln Gln Lys Ala Leu Ser
                245                 250                 255

Arg Ala Leu Leu Glu Leu Arg Ala Glu Met Thr Ala Ala Ala Glu Glu
            260                 265                 270

Arg Ile Ile Ser Ala Thr Ser Gln Lys Glu Ala His Leu Asn Val Gln
        275                 280                 285

Gln Ile Val Asp Arg His Thr Arg Glu Leu Lys Thr Gln Val Glu Asp
    290                 295                 300

Leu Asn Glu Asn Leu Leu Lys Leu Lys Glu Ala Leu Lys Thr Ser Lys
305                 310                 315                 320

Asn Arg Glu Asn Ser Leu Thr Asp Asn Leu Asn Asp Leu Asn Asn Glu
                325                 330                 335

Leu Gln Lys Lys Gln Lys Ala Tyr Asn Lys Ile Leu Arg Glu Lys Glu
            340                 345                 350

Glu Ile Asp Gln Glu Asn Asp Glu Leu Lys Arg Gln Ile Lys Arg Leu
        355                 360                 365

Thr Ser Gly Leu Gln Gly Lys Pro Leu Thr Asp Asn Lys Gln Ser Leu
    370                 375                 380

Ile Glu Glu Leu Gln Arg Lys Val Lys Lys Leu Glu Asn Gln Leu Glu
385                 390                 395                 400

Gly Lys Val Glu Glu Val Asp Leu Lys Pro Met Lys Glu Lys Asn Ala
                405                 410                 415

Lys Glu Glu Leu Ile Arg Trp Glu Glu Gly Lys Lys Trp Gln Ala Lys
            420                 425                 430

Ile Glu Gly Ile Arg Asn Lys Leu Lys Glu Lys Glu Gly Glu Val Phe
        435                 440                 445

Thr Leu Thr Lys Gln Leu Asn Thr Leu Lys Asp Leu Phe Ala Lys Ala
    450                 455                 460

Asp Lys Glu Lys Leu Thr Leu Gln Arg Lys Leu Lys Thr Thr Gly Met
465                 470                 475                 480

Thr Val Asp Gln Val Leu Gly Ile Arg Ala Leu Glu Ser Glu Lys Glu
                485                 490                 495

Leu Glu Glu Leu Lys Lys Arg Asn Leu Asp Leu Glu Asn Asp Ile Leu
            500                 505                 510

Tyr Met Arg Ala His Gln Ala Leu Pro Arg Asp Ser Val Val Glu Asp
        515                 520                 525

Leu His Leu Gln Asn Arg Tyr Leu Gln Glu Lys Leu His Ala Leu Glu
    530                 535                 540

Lys Gln Phe Ser Lys Asp Thr Tyr Ser Lys Pro Ser Ile Ser Gly Ile
545                 550                 555                 560

Glu Ser Asp Asp His Cys Gln Arg Glu Gln Glu Leu Gln Lys Glu Asn
                565                 570                 575

Leu Lys Leu Ser Ser Glu Asn Ile Glu Leu Lys Phe Gln Leu Glu Gln
            580                 585                 590

Ala Asn Lys Asp Leu Pro Arg Leu Lys Asn Gln Val Arg Asp Leu Lys
        595                 600                 605

Glu Met Cys Glu Phe Leu Lys Lys Glu Lys Ala Glu Val Gln Arg Lys
    610                 615                 620

Leu Gly His Val Arg Gly Ser Gly Arg Ser Gly Lys Thr Ile Pro Glu
625                 630                 635                 640
```

Leu Glu Lys Thr Ile Gly Leu Met Lys Lys Val Val Glu Lys Val Gln
645 650 655

Arg Glu Asn Glu Gln Leu Lys Lys Ala Ser Gly Ile Leu Thr Ser Glu
660 665 670

Lys Met Ala Asn Ile Glu Gln Glu Asn Glu Lys Leu Lys Ala Glu Leu
675 680 685

Glu Lys Leu Lys Ala His Leu Gly His Gln Leu Ser Met His Tyr Glu
690 695 700

Ser Lys Thr Lys Gly Thr Glu Lys Ile Ile Ala Glu Asn Glu Arg Leu
705 710 715 720

Arg Lys Glu Leu Lys Lys Glu Thr Asp Ala Ala Glu Lys Leu Arg Ile
725 730 735

Ala Lys Asn Asn Leu Glu Ile Leu Asn Glu Lys Met Thr Val Gln Leu
740 745 750

Glu Glu Thr Gly Lys Arg Leu Gln Phe Ala Glu Ser Arg Gly Pro Gln
755 760 765

Leu Glu Gly Ala Asp Ser Lys Ser Trp Lys Ser Ile Val Val Thr Arg
770 775 780

Met Tyr Glu Thr Lys Leu Lys Glu Leu Glu Thr Asp Ile Ala Lys Lys
785 790 795 800

Asn Gln Ser Ile Thr Asp Leu Lys Gln Leu Val Lys Glu Ala Thr Glu
805 810 815

Arg Glu Gln Lys Val Asn Lys Tyr Asn Glu Asp Leu Glu Gln Gln Ile
820 825 830

Lys Ile Leu Lys His Val Pro Glu Gly Ala Glu Thr Glu Gln Gly Leu
835 840 845

Lys Arg Glu Leu Gln Val Leu Arg Leu Ala Asn His Gln Leu Asp Lys
850 855 860

Glu Lys Ala Glu Leu Ile His Gln Ile Glu Ala Asn Lys Asp Gln Ser
865 870 875 880

Gly Ala Glu Ser Thr Ile Pro Asp Ala Asp Gln Leu Lys Glu Lys Ile
885 890 895

Lys Asp Leu Glu Thr Gln Leu Lys Met Ser Asp Leu Glu Lys Gln His
900 905 910

Leu Lys Glu Glu Ile Lys Lys Leu Lys Lys Glu Leu Glu Asn Phe Asp
915 920 925

Pro Ser Phe Phe Glu Glu Ile Glu Asp Leu Lys Tyr Asn Tyr Lys Glu
930 935 940

Glu Val Lys Lys Asn Ile Leu Leu Glu Glu Lys Val Lys Lys Leu Ser
945 950 955 960

Glu Gln Leu Gly Val Glu Leu Thr Ser Pro Val Ala Ala Ser Glu Glu
965 970 975

Phe Glu Asp Glu Glu Glu Ser Pro Val Asn Phe Pro Ile Tyr
980 985 990

<210> SEQ ID NO 12
<211> LENGTH: 2973
<212> TYPE: DNA
<213> ORGANISM: Homo sapiens

<400> SEQUENCE: 12
ttagtaaatg gggaaattaa caggactttc ttcttcatct tcaaactctt cagaagcagc 60
aacagggcta gttaattcaa ctcccaattg ttctgaaagt ttttttacct tctcttctaa 120

-continued

```
gagaatattc ttcttcactt cttccttgta attatactta agatcttcaa tttcttcaaa    180
aaatgaagga tcaaaatttt ccagttcttt tttcagcttc tttatttcct ccttcaaatg    240
ctgcttttct agatctgaca ttttgagctg tgtctctaga tcttttattt tttcctttag    300
ttgatcagca tcaggtatgg tgctttcagc tccactttgg tccttgttag cttctatctg    360
atggattaat tctgctttct ctttatccag ctgatgatta gctaatctaa gaacttgaag    420
ctcccgttta aggccttgct ctgtctcagc accttcagga acatgtttaa gaatcttaat    480
ctgttgttca aggtcttcat tgtatttgtt aactttttgt tctctctctg ttgcttcttt    540
tacaagctgt ttaaggtcag taatgctttg atttttttg gcaatatcag tttccaattc     600
ttttaacttg gtttcataca ttcttgtaac cacaatggat ttccagctct tactgtcagc    660
accttcaagc tgtggacctc tgctttctgc aaactgcaat ctcttaccag tctcttctag    720
ttgaactgtc atcttctcat ttaatatctc taaattattc tttgctatcc gtaatttctc    780
tgcagcatca gtttcttttt taagttcttt acgaagcctt tcattttcag caataatttt    840
ttctgtgcct ttggtcttgg attcatagtg catgctcaac tgatgcccaa gatgagcttt    900
aagtttttct aattcagcct tcaatttttc attttcctgc tcaatattag ccatttttc     960
actagtcaat attcctgatg ctttttcaa ctgttcattt tctctctgga cttttcaac     1020
tacttttttc attaaaccaa tggtttttc cagttctggg attgtctttc cacttctacc    1080
agaccctcta acatggccaa gtttccgctg aacttctgct ttttctttct taagaaattc   1140
acacatttcc ttcaaatctc tgacttgatt ctttaatctt ggcaaatctt tatttgcttg   1200
ttcaagctga aatttcagtt caatattttc agatgacaac ttcaagtttt ccttctgaag   1260
ctcctgttct ctctgacaat gatcatctga ctctattcct gaaattgaag gcttagaata   1320
tgtatccttt gaaaactgtt tttctaaagc atgaagtttt tcttggaggt atctattttg   1380
taaatgtaaa tcttctacaa cagaatctcg aggaagagct tggtgggccc tcatatacaa   1440
tatatcattt tctaagtcaa gatttctctt ttttaattct tccaattctt tttctgactc   1500
caaagctcgt attcccaaaa cctgatcaac agtcatgcca gttgttttta gtttcctctg   1560
caaagtaagt ttctctttat cggctttggc aaaaagatcc ttcaaagtat tcaactgctt   1620
tgttaaagta aagacttccc cctctttctc ttttaacttg tttcgaattc cttctatttt   1680
ggcttgccac tttttacctt cttcccacct aattaattct tctttagcat tcttttcttt   1740
cataggtttt aggtctactt cctccacctt tccctctaat tggttctcta gtttttaac    1800
tttcctttgg agttcttcaa ttagactttg tttattatct gtcaggggtt tgccctgtaa   1860
tccactggtt agtcttttaa tttgcctttt cagttcatca ttctcttgat caatttcctc   1920
tttctctcta agtattttat tataggcttt ttgtttcttt tgcagttcat tatttaagtc   1980
attcaaatta tcagttagtg agttttctct gtttttactt gttttaagtg cttctttcaa   2040
ttttaaaaga ttttcattta aatcttcaac ttgtgtcttt agctctctag tatgtcgatc   2100
aacgatttgt tgaacattga gatgggcctc tttttgagaa gttgcagaaa taatacgttc   2160
ttcagcagct gctgtcattt ctgcccggag ttctaaaagt gcccgactaa gtgctttctg   2220
ttgtttctcc ttcaaggcta attggctctt tagccgttct actagatttc tcattgtagt   2280
tgttggagct cttgaatttg cttctttttg agcctgaagt tcagatttta aacactgtga   2340
ctccttttgt gactggtcca gaagatactt taaatcctct acttccgctt ttactttttt   2400
cacttcatct tcatggtttt cttgaagctg taatttgata ttttcaaatt cttttacttt   2460
taattcagtg atttctcttt gtctctccaa atcttgtgat actttcttta gtttgaccaa   2520
```

```
gagtgaggaa agagagtcat cttgttctgc tactgtctgt tccatctcag ccagacgaat   2580

aaaatgcttg ttggtaggaa ctggagtggg agactgtttc attaaatccc aagccgtttg   2640

tttgaattta tttagtgaac tatcagcctg tagttctaat ctgtgatgaa gaatatgaag   2700

gtcttcctca tgtttcttca caatttctct ttgctcctct ctggcttttt ctagaagacg   2760

ttgatacttc tttaatactt cttcttttg atttaacctt gcttgcatgt ttgcaatggt   2820

ttgatgagca attttcaatg tgtggtgaga ttttggttcc atctcttttc tgcctagctc   2880

agctatgagc ttttctcttt ctgcagtggc aggcaatcga agcctcagtt cattgattac   2940

tttgtctctt gacagtatat tttgttctgc taa                                 2973
```

<210> SEQ ID NO 13
<211> LENGTH: 130
<212> TYPE: DNA
<213> ORGANISM: adeno-associated virus 2

<400> SEQUENCE: 13

```
ctgcgcgctc gctcgctcac tgaggccgcc cgggcaaagc ccgggcgtcg ggcgaccttt     60

ggtcgcccgg cctcagtgag cgagcgagcg cgcagagagg gagtggccaa ctccatcact    120

aggggttcct                                                           130
```

<210> SEQ ID NO 14
<211> LENGTH: 130
<212> TYPE: DNA
<213> ORGANISM: adeno-associated virus 2

<400> SEQUENCE: 14

```
aggaacccct agtgatggag ttggccactc cctctctgcg cgctcgctcg ctcactgagg     60

ccgggcgacc aaaggtcgcc cgacgcccgg gctttgcccg ggcggcctca gtgagcgagc    120

gagcgcgcag                                                           130
```

<210> SEQ ID NO 15
<211> LENGTH: 6
<212> TYPE: DNA
<213> ORGANISM: adeno-associated virus 2

<400> SEQUENCE: 15

```
agttgg                                                                 6
```

<210> SEQ ID NO 16
<211> LENGTH: 16
<212> TYPE: DNA
<213> ORGANISM: adeno-associated virus 2

<400> SEQUENCE: 16

```
gcgcgctcgc tcgctc                                                     16
```

<210> SEQ ID NO 17
<211> LENGTH: 294
<212> TYPE: DNA
<213> ORGANISM: Homo sapiens

<400> SEQUENCE: 17

```
gggccccaga agcctggtgg ttgtttgtcc ttctcagggg aaaagtgagg cggccccttg     60

gaggaagggg ccgggcagaa tgatctaatc ggattccaag cagctcaggg gattgtcttt    120

ttctagcacc ttcttgccac tcctaagcgt cctccgtgac cccggctggg atttagcctg    180
```

gtgctgtgtc agccccgggc tcccaggggc ttcccagtgg tccccaggaa ccctcgacag 240
ggccagggcg tctctctcgt ccagcaaggg cagggacggg ccacaggcca aggg 294

<210> SEQ ID NO 18
<211> LENGTH: 660
<212> TYPE: DNA
<213> ORGANISM: Cytomegalovirus

<400> SEQUENCE: 18
cgcgtggagc tagttattaa tagtaatcaa ttacggggtc attagttcat agcccatata 60
tggagttccg cgttacataa cttacggtaa atggcccgcc tggctgaccg cccaacgacc 120
cccgcccatt gacgtcaata atgacgtatg ttcccatagt aacgtcaata gggactttcc 180
attgacgtca atgggtggag tatttacggt aaactgccca cttggcagta catcaagtgt 240
atcatatgcc aagtacgccc cctattgacg tcaatgacgg taaatggccc gcctggcatt 300
atgcccagta catgacctta tgggactttc ctacttggca gtacatctac gtattagtca 360
tcgctattac catggtgatg cggttttggc agtacatcaa tgggcgtgga tagcggtttg 420
actcacgggg atttccaagt ctccacccca ttgacgtcaa tgggagtttg ttttgcacca 480
aaatcaacgg gactttccaa aatgtcgtaa caactccgcc ccattgacgc aaatgggcgg 540
taggcgtgta cggtgggagg tctatataag cagagctcgt ttagtgaacc gtcagatcgc 600
ctggagacgc catccacgct gttttgacct ccatagaaga caccgggacc gatccagcct 660

<210> SEQ ID NO 19
<211> LENGTH: 2217
<212> TYPE: DNA
<213> ORGANISM: Adeno-associated virus type 8

<400> SEQUENCE: 19
atggctgccg atggttatct tccagattgg ctcgaggaca acctctctga gggcattcgc 60
gagtggtggg cgctgaaacc tggagccccg aagcccaaag ccaaccagca aaagcaggac 120
gacggccggg gtctggtgct tcctggctac aagtacctcg gacccttcaa cggactcgac 180
aagggggagc ccgtcaacgc ggcggacgca gcggccctcg agcacgacaa ggcctacgac 240
cagcagctgc aggcgggtga caatccgtac ctgcggtata accacgccga cgccgagttt 300
caggagcgtc tgcaagaaga tacgtctttt gggggcaacc tcgggcgagc agtcttccag 360
gccaagaagc gggttctcga acctctcggt ctggttgagg aaggcgctaa gacggctcct 420
ggaaagaaga gaccggtaga gccatcaccc cagcgttctc cagactcctc tacgggcatc 480
ggcaagaaag gccaacagcc cgccagaaaa agactcaatt ttggtcagac tggcgactca 540
gagtcagttc cagaccctca acctctcgga gaacctccag cagcgccctc tggtgtggga 600
cctaatacaa tggctgcagg cggtggcgca ccaatggcag acaataacga aggcgccgac 660
ggagtgggta gttcctcggg aaattggcat tgcgattcca catggctggg cgacagagtc 720
atcaccacca gcacccgaac ctgggccctg cccacctaca acaaccacct ctacaagcaa 780
atctccaacg ggacatcggg aggagccacc aacgacaaca cctacttcgg ctacagcacc 840
ccctgggggt attttgactt taacagattc cactgccact tttcaccacg tgactggcag 900
cgactcatca acaacaactg gggattccgg cccaagagac tcagcttcaa gctcttcaac 960
atccaggtca aggaggtcac gcagaatgaa ggcaccaaga ccatcgccaa taacctcacc 1020
agcaccatcc aggtgtttac ggactcggag taccagctgc cgtacgttct cggctctgcc 1080
caccagggct gcctgcctcc gttcccggcg gacgtgttca tgattcccca gtacggctac 1140

-continued ctaacactca acaacggtag tcaggccgtg ggacgctcct ccttctactg cctggaatac 1200
tttccttcgc agatgctgag aaccggcaac aacttccagt ttacttacac cttcgaggac 1260
gtgcctttcc acagcagcta cgcccacagc cagagcttgg accggctgat gaatcctctg 1320
attgaccagt acctgtacta cttgtctcgg actcaaacaa caggaggcac ggcaaatacg 1380
cagactctgg gcttcagcca aggtgggcct aatacaatgg ccaatcaggc aaagaactgg 1440
ctgccaggac cctgttaccg ccaacaacgc gtctcaacga caaccgggca aaacaacaat 1500
agcaactttg cctggactgc tgggaccaaa taccatctga atggaagaaa ttcattggct 1560
aatcctggca tcgctatggc aacacacaaa gacgacgagg agcgtttttt tcccagtaac 1620
gggatcctga tttttggcaa acaaaatgct gccagagaca atgcggatta cagcgatgtc 1680
atgctcacca gcgaggaaga aatcaaaacc actaaccctg tggctacaga ggaatacggt 1740
atcgtggcag ataacttgca gcagcaaaac acggctcctc aaattggaac tgtcaacagc 1800
cagggggcct tacccggtat ggtctggcag aaccgggacg tgtacctgca gggtcccatc 1860
tgggccaaga ttcctcacac ggacggcaac ttccacccgt ctccgctgat gggcggcttt 1920
ggcctgaaac atcctccgcc tcagatcctg atcaagaaca cgcctgtacc tgcggatcct 1980
ccgaccacct tcaaccagtc aaagctgaac tctttcatca cgcaatacag caccggacag 2040
gtcagcgtgg aaattgaatg ggagctgcag aaggaaaaca gcaagcgctg gaaccccgag 2100
atccagtaca cctccaacta ctacaaatct acaagtgtgg actttgctgt taatacagaa 2160
ggcgtgtact ctgaaccccg ccccattggc acccgttacc tcacccgtaa tctgtaa 2217

<210> SEQ ID NO 20
<211> LENGTH: 738
<212> TYPE: PRT
<213> ORGANISM: Adeno-associated virus type 8

<400> SEQUENCE: 20

Met Ala Ala Asp Gly Tyr Leu Pro Asp Trp Leu Glu Asp Asn Leu Ser
1 5 10 15

Glu Gly Ile Arg Glu Trp Trp Ala Leu Lys Pro Gly Ala Pro Lys Pro
20 25 30

Lys Ala Asn Gln Gln Lys Gln Asp Asp Gly Arg Gly Leu Val Leu Pro
35 40 45

Gly Tyr Lys Tyr Leu Gly Pro Phe Asn Gly Leu Asp Lys Gly Glu Pro
50 55 60

Val Asn Ala Ala Asp Ala Ala Ala Leu Glu His Asp Lys Ala Tyr Asp
65 70 75 80

Gln Gln Leu Gln Ala Gly Asp Asn Pro Tyr Leu Arg Tyr Asn His Ala
85 90 95

Asp Ala Glu Phe Gln Glu Arg Leu Gln Glu Asp Thr Ser Phe Gly Gly
100 105 110

Asn Leu Gly Arg Ala Val Phe Gln Ala Lys Lys Arg Val Leu Glu Pro
115 120 125

Leu Gly Leu Val Glu Glu Gly Ala Lys Thr Ala Pro Gly Lys Lys Arg
130 135 140

Pro Val Glu Pro Ser Pro Gln Arg Ser Pro Asp Ser Ser Thr Gly Ile
145 150 155 160

Gly Lys Lys Gly Gln Gln Pro Ala Arg Lys Arg Leu Asn Phe Gly Gln
165 170 175

Thr Gly Asp Ser Glu Ser Val Pro Asp Pro Gln Pro Leu Gly Glu Pro

-continued

```
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525

His Lys Asp Asp Glu Glu Arg Phe Phe Pro Ser Asn Gly Ile Leu Ile
    530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
        595                 600                 605
```

```
Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu


<210> SEQ ID NO 21
<211> LENGTH: 294
<212> TYPE: DNA
<213> ORGANISM: Adeno-associated virus type 8

<400> SEQUENCE: 21

cccttggcct gtggcccgtc cctgcccttg ctggacgaga gagacgccct ggccctgtcg      60

agggttcctg ggaccactgg ggaagcccct gggagcccgg ggctgacaca gcaccaggct     120

aaatcccagc cggggtcacg gaggacgctt aggagtggca agaaggtgct agaaaaagac     180

aatcccctga gctgcttgga atccgattag atcattctgc ccggcccctt cctccaaggg     240

gccgcctcac ttttcccctg agaaggacaa acaaccacca ggcttctggg gccc           294


<210> SEQ ID NO 22
<211> LENGTH: 897
<212> TYPE: DNA
<213> ORGANISM: Mus musculus

<400> SEQUENCE: 22

gatttactta agcagtctcc tgctccagtt cccaccaaca aacatttcat tcgtctggcc      60

gagatggagc agacagtagc agaacaagat gactctctgt cctcactttt gaccaaacta     120

aagaaagtat caaaagattt ggaaaaacaa aaagaaatca ctgagttaaa agtcagagag     180

tttgaaaata ccaaactacg gctccaagaa actcatgcca gtgaggtaaa gaaagtgaaa     240

gcagaggtag aggacttaag gcatgctcta gcccaagcac acaaggactc ccagagttta     300

aagtctgaac tccaggctca gaaagaagca aactccagag ctccaacaac cacaatgagg     360

aatcttgtag acaggctaaa gagccaacta gccttgaaag agaagcaaca aaaggcactt     420

agtcgagccc tgttggaact tcggtcggaa atgacagcag cagctgagga acgtataatc     480

gctgtaactt ctcaaaaaga ggcaaatctc aatgttcaac aagttgttga gcgccatact     540

agagagctaa agtcacaaat tgaagattta aatgaaaatc ttttaaaatt gaaagaagct     600

cttaaaacaa gtaagaacaa agaaaattca ctagctgatg atttaaatga attaaataat     660

gaactgcaaa aaaagcaaaa agcttataat aaaatcctta gagagaaaga tggaattgat     720

caagaaaatg atgaactgag aagacagatt aaaagactgt ccagtggact gcagagcaaa     780
```

actttgatag ataacaagca aagtttaatc gatgaacttc aaaagaaagt taaaaaactt 840
gaaagccaac tggaaagaaa ggtggatgac gtagacataa agccggtgaa ggaaaag 897

<210> SEQ ID NO 23
<211> LENGTH: 299
<212> TYPE: PRT
<213> ORGANISM: Mus musculus

<400> SEQUENCE: 23

Asp Leu Leu Lys Gln Ser Pro Ala Pro Val Pro Thr Asn Lys His Phe
1 5 10 15

Ile Arg Leu Ala Glu Met Glu Gln Thr Val Ala Glu Gln Asp Asp Ser
20 25 30

Leu Ser Ser Leu Leu Thr Lys Leu Lys Lys Val Ser Lys Asp Leu Glu
35 40 45

Lys Gln Lys Glu Ile Thr Glu Leu Lys Val Arg Glu Phe Glu Asn Thr
50 55 60

Lys Leu Arg Leu Gln Glu Thr His Ala Ser Glu Val Lys Lys Val Lys
65 70 75 80

Ala Glu Val Glu Asp Leu Arg His Ala Leu Ala Gln Ala His Lys Asp
85 90 95

Ser Gln Ser Leu Lys Ser Glu Leu Gln Ala Gln Lys Glu Ala Asn Ser
100 105 110

Arg Ala Pro Thr Thr Thr Met Arg Asn Leu Val Asp Arg Leu Lys Ser
115 120 125

Gln Leu Ala Leu Lys Glu Lys Gln Gln Lys Ala Leu Ser Arg Ala Leu
130 135 140

Leu Glu Leu Arg Ser Glu Met Thr Ala Ala Ala Glu Glu Arg Ile Ile
145 150 155 160

Ala Val Thr Ser Gln Lys Glu Ala Asn Leu Asn Val Gln Gln Val Val
165 170 175

Glu Arg His Thr Arg Glu Leu Lys Ser Gln Ile Glu Asp Leu Asn Glu
180 185 190

Asn Leu Leu Lys Leu Lys Glu Ala Leu Lys Thr Ser Lys Asn Lys Glu
195 200 205

Asn Ser Leu Ala Asp Asp Leu Asn Glu Leu Asn Asn Glu Leu Gln Lys
210 215 220

Lys Gln Lys Ala Tyr Asn Lys Ile Leu Arg Glu Lys Asp Gly Ile Asp
225 230 235 240

Gln Glu Asn Asp Glu Leu Arg Arg Gln Ile Lys Arg Leu Ser Ser Gly
245 250 255

Leu Gln Ser Lys Thr Leu Ile Asp Asn Lys Gln Ser Leu Ile Asp Glu
260 265 270

Leu Gln Lys Lys Val Lys Lys Leu Glu Ser Gln Leu Glu Arg Lys Val
275 280 285

Asp Asp Val Asp Ile Lys Pro Val Lys Glu Lys
290 295

<210> SEQ ID NO 24
<211> LENGTH: 897
<212> TYPE: DNA
<213> ORGANISM: Mus musculus

<400> SEQUENCE: 24
cttttccttc accggcttta tgtctacgtc atccaccttt ctttccagtt ggctttcaag 60

-continued

```
tttttaact ttcttttgaa gttcatcgat taaactttgc ttgttatcta tcaaagtttt    120

gctctgcagt ccactggaca gtcttttaat ctgtcttctc agttcatcat tttcttgatc    180

aattccatct ttctctctaa ggattttatt ataagctttt tgcttttttt gcagttcatt    240

atttaattca tttaaatcat cagctagtga attttctttg ttcttacttg ttttaagagc    300

ttctttcaat tttaaaagat tttcatttaa atcttcaatt tgtgacttta gctctctagt    360

atggcgctca acaacttgtt gaacattgag atttgcctct ttttgagaag ttacagcgat    420

tatacgttcc tcagctgctg ctgtcatttc cgaccgaagt tccaacaggg ctcgactaag    480

tgcctttgt tgcttctctt tcaaggctag ttggctcttt agcctgtcta caagattcct    540

cattgtggtt gttggagctc tggagtttgc ttctttctga gcctggagtt cagactttaa    600

actctgggag tccttgtgtg cttgggctag agcatgcctt aagtcctcta cctctgcttt    660

cactttcttt acctcactgg catgagtttc ttggagccgt agtttggtat tttcaaactc    720

tctgactttt aactcagtga tttctttttg tttttccaaa tcttttgata ctttctttag    780

tttggtcaaa agtgaggaca gagagtcatc ttgttctgct actgtctgct ccatctcggc    840

cagacgaatg aaatgtttgt tggtgggaac tggagcagga gactgcttaa gtaaatc       897
```

<210> SEQ ID NO 25
<211> LENGTH: 897
<212> TYPE: DNA
<213> ORGANISM: Homo sapiens

<400> SEQUENCE: 25

```
gatttaatga aacagtctcc cactccagtt cctaccaaca agcattttat tcgtctggct     60

gagatggaac agacagtagc agaacaagat gactctcttt cctcactctt ggtcaaacta    120

aagaaagtat cacaagattt ggagagacaa agagaaatca ctgaattaaa agtaaaagaa    180

tttgaaaata tcaaattaca gcttcaagaa aaccatgaag atgaagtgaa aaaagtaaaa    240

gcggaagtag aggatttaaa gtatcttctg gaccagtcac aaaaggagtc acagtgttta    300

aaatctgaac ttcaggctca aaaagaagca aattcaagag ctccaacaac tacaatgaga    360

aatctagtag aacggctaaa gagccaatta gccttgaagg agaaacaaca gaaagcactt    420

agtcgggcac ttttagaact ccgggcagaa atgacagcag ctgctgaaga acgtattatt    480

tctgcaactt ctcaaaaaga ggcccatctc aatgttcaac aaatcgttga tcgacatact    540

agagagctaa agacacaagt tgaagattta aatgaaaatc ttttaaaatt gaaagaagca    600

cttaaaacaa gtaaaaacag agaaaactca ctaactgata atttgaatga cttaaataat    660

gaactgcaaa agaaacaaaa agcctataat aaaatactta gagagaaaga ggaaattgat    720

caagagaatg atgaactgaa aaggcaaatt aaaagactaa ccagtggatt acagggcaaa    780

cccctgacag ataataaaca aagtctaatt gaagaactcc aaaggaaagt taaaaaacta    840

gagaaccaat tagagggaaa ggtggaggaa gtagacctaa aacctatgaa agaaaag       897
```

<210> SEQ ID NO 26
<211> LENGTH: 299
<212> TYPE: PRT
<213> ORGANISM: Homo sapiens

<400> SEQUENCE: 26

```
Asp Leu Met Lys Gln Ser Pro Thr Pro Val Pro Thr Asn Lys His Phe
1               5                   10                  15

Ile Arg Leu Ala Glu Met Glu Gln Thr Val Ala Glu Gln Asp Asp Ser
            20                  25                  30
```

```
Leu Ser Ser Leu Leu Val Lys Leu Lys Lys Val Ser Gln Asp Leu Glu
        35                  40                  45

Arg Gln Arg Glu Ile Thr Glu Leu Lys Val Lys Glu Phe Glu Asn Ile
    50                  55                  60

Lys Leu Gln Leu Gln Glu Asn His Glu Asp Glu Val Lys Lys Val Lys
65                  70                  75                  80

Ala Glu Val Glu Asp Leu Lys Tyr Leu Leu Asp Gln Ser Gln Lys Glu
                85                  90                  95

Ser Gln Cys Leu Lys Ser Glu Leu Gln Ala Gln Lys Glu Ala Asn Ser
            100                 105                 110

Arg Ala Pro Thr Thr Thr Met Arg Asn Leu Val Glu Arg Leu Lys Ser
        115                 120                 125

Gln Leu Ala Leu Lys Glu Lys Gln Gln Lys Ala Leu Ser Arg Ala Leu
    130                 135                 140

Leu Glu Leu Arg Ala Glu Met Thr Ala Ala Ala Glu Glu Arg Ile Ile
145                 150                 155                 160

Ser Ala Thr Ser Gln Lys Glu Ala His Leu Asn Val Gln Gln Ile Val
                165                 170                 175

Asp Arg His Thr Arg Glu Leu Lys Thr Gln Val Glu Asp Leu Asn Glu
            180                 185                 190

Asn Leu Leu Lys Leu Lys Glu Ala Leu Lys Thr Ser Lys Asn Arg Glu
        195                 200                 205

Asn Ser Leu Thr Asp Asn Leu Asn Asp Leu Asn Asn Glu Leu Gln Lys
    210                 215                 220

Lys Gln Lys Ala Tyr Asn Lys Ile Leu Arg Glu Lys Glu Glu Ile Asp
225                 230                 235                 240

Gln Glu Asn Asp Glu Leu Lys Arg Gln Ile Lys Arg Leu Thr Ser Gly
                245                 250                 255

Leu Gln Gly Lys Pro Leu Thr Asp Asn Lys Gln Ser Leu Ile Glu Glu
            260                 265                 270

Leu Gln Arg Lys Val Lys Lys Leu Glu Asn Gln Leu Glu Gly Lys Val
        275                 280                 285

Glu Glu Val Asp Leu Lys Pro Met Lys Glu Lys
    290                 295
```

<210> SEQ ID NO 27
<211> LENGTH: 897
<212> TYPE: DNA
<213> ORGANISM: Homo sapiens

<400> SEQUENCE: 27

```
cttttctttc ataggtttta ggtctacttc ctccaccttt ccctctaatt ggttctctag      60

tttttaact ttcctttgga gttcttcaat tagactttgt ttattatctg tcaggggttt      120

gccctgtaat ccactggtta gtcttttaat ttgccttttc agttcatcat tctcttgatc     180

aatttcctct ttctctctaa gtattttatt ataggctttt tgtttctttt gcagttcatt     240

atttaagtca ttcaaattat cagttagtga gttttctctg tttttacttg ttttaagtgc     300

ttctttcaat tttaaaagat tttcatttaa atcttcaact tgtgtcttta gctctctagt     360

atgtcgatca acgatttgtt gaacattgag atgggcctct ttttgagaag ttgcagaaat     420

aatacgttct tcagcagctg ctgtcatttc tgcccggagt tctaaaagtg cccgactaag     480

tgctttctgt tgtttctcct tcaaggctaa ttggctcttt agccgttcta ctagatttct     540

cattgtagtt gttggagctc ttgaatttgc ttctttttga gcctgaagtt cagattttaa     600
```

acactgtgac tccttttgtg actggtccag aagatacttt aaatcctcta cttccgcttt 660
tacttttttc acttcatctt catggttttc ttgaagctgt aatttgatat tttcaaattc 720
ttttactttt aattcagtga tttctctttg tctctccaaa tcttgtgata ctttctttag 780
tttgaccaag agtgaggaaa gagagtcatc ttgttctgct actgtctgtt ccatctcagc 840
cagacgaata aaatgcttgt tggtaggaac tggagtggga gactgtttca ttaaatc 897

<210> SEQ ID NO 28
<211> LENGTH: 3924
<212> TYPE: DNA
<213> ORGANISM: Mus musculus

<400> SEQUENCE: 28
caacaacagt ccagggaaaa ggaagtggaa tccctcagaa cgcagctgct ggacttccag 60
gcacaatctg acgaaaaggc tctaattgcc aaattgcacc aacatgttgt ctctcttcaa 120
attagtgagg ccactgccct cggtaagtta gagtcagtta cgtccaaact ccagaagatg 180
gaagcctaca atttgcgctt agaacagaaa ctggatgaaa aagagcaggc gctctactat 240
gctcgtttgg aaggtagaaa cagagcaaaa cacctgcgcc aaaccattca gtcgcttcga 300
agacagttca gtggagctct acccttagca cagcaggaaa agttctccaa aacgatgatt 360
cagttgcaaa atgacaaact taagataatg caagaaatga agaattcgca acaggaacac 420
agaaatatgg aaaacaaaac actggagttg gaattaaaat taaaaggctt agaagaattg 480
atcagtactt taaaggatgc caggggagcc cagaaggtaa tcaattggca tgtgaaaata 540
gaagaacttc gcctccaaga acttaagcta aatagagaac tagtcaaggg taaagaagaa 600
atcaaatatt tgaataatat catctctgaa tatgagcata caatcaacag tctagaggaa 660
gaaattgttc agcaaagcaa gttccatgaa gaaagacaga tggcttggga tcaaagagaa 720
gttgagctgg aacgccagtt agacattttt gatcatcagc aaaatgaaat actcagtgca 780
gcacaaaagt ttgaagactc tacaggatca atgccagacc ccagcttgcc tcttccaaac 840
caacttgaaa ttgctctaag aaaaattaag gagaatattc aagtaattct taaaacacaa 900
gcaacttgca agtcactaga agagaaacta aaagaaaaag aatctgcttt acggttggca 960
gagcaaaata ttctgtcaag agacaaagta atcaatgaac tgaggcttcg attgcctgcc 1020
acggctgatc gagaaaaact tatagctgag ctagaaagaa aagagctgga gccgaaatct 1080
catcacacaa tgaaaattgc ccaccaaact attgccaaca tgcaggcaag gttaaatcac 1140
aaggaagaag tattgaagaa ataccagcac cttctggaga aggccagaga ggagcaaaga 1200
gaaattgtta agaagcatga ggaagacctt catgttcttc atcacaaatt agaacaacag 1260
gccgataatt cactcaataa attcagacag acagctcagg atttacttaa gcagtctcct 1320
gctccagttc ccaccaacaa acatttcatt cgtctggccg agatggagca gacagtagca 1380
gaacaagatg actctctgtc ctcacttttg accaaactaa agaaagtatc aaaagatttg 1440
gaaaaacaaa aagaaatcac tgagttaaaa gtcagagagt ttgaaaatac caaactacgg 1500
ctccaagaaa ctcatgccag tgaggtaaag aaagtgaaag cagaggtaga ggacttaagg 1560
catgctctag cccaagcaca caaggactcc cagagtttaa agtctgaact ccaggctcag 1620
aaagaagcaa actccagagc tccaacaacc acaatgagga atcttgtaga caggctaaag 1680
agccaactag ccttgaaaga gaagcaacaa aaggcactta gtcgagccct gttggaactt 1740
cggtcggaaa tgacagcagc agctgaggaa cgtataatcg ctgtaacttc tcaaaaagag 1800

-continued gcaaatctca atgttcaaca agttgttgag cgccatacta gagagctaaa gtcacaaatt 1860
gaagatttaa atgaaaatct tttaaaattg aaagaagctc ttaaaacaag taagaacaaa 1920
gaaaattcac tagctgatga tttaaatgaa ttaaataatg aactgcaaaa aaagcaaaaa 1980
gcttataata aaatccttag agagaaagat ggaattgatc aagaaaatga tgaactgaga 2040
agacagatta aaagactgtc cagtggactg cagagcaaaa ctttgataga taacaagcaa 2100
agtttaatcg atgaacttca aaagaaagtt aaaaaacttg aaagccaact ggaaagaaag 2160
gtggatgacg tagacataaa gccggtgaag gaaaagagta gtaaagaaga attaattagg 2220
tgggaagaag gtaagaaatg gcaaaccaaa gtagagggac tacgaaacag actaaaggag 2280
aaggaaggag aagcccacgg cctggcaaag cagctgaata ccttaaagga actttttgcc 2340
aaagctgata aagagaaact tactttgcag aagaaactga aaacaacagg aatgactgtt 2400
gaccaggttt taggagtgcg agctttggaa tctgaaaaag agttggaaga gctaaaaaag 2460
aaaaatctgg acctagaaaa tgacatatta tacatgagga cccagcaggc tcttccacga 2520
gattctgttg tggaagactt acatttacaa aataaatacc ttcaagaaaa acttcatact 2580
ttagaaaaaa aactttcaaa ggagaaatat tctcagtctt tgacttcaga aatagagtca 2640
gatgatcact gtcaaaaaga acaagaactt cagaaggaaa atttgaagtt gtcatctgaa 2700
aacatcgagc tgaaatttca acttgaacaa gcaaataaag atttgccaag actaaagaat 2760
caagtgaaag atttgaagga aatgtgtgaa tttcttaaga aaggaaaact ggaacttgag 2820
cggaagcttg gtcaggtcag aggggctggt agaagtggga agacaatccc agaactagaa 2880
aaaaccattg ggttaatgaa gaaagtagtt gaaaaagtcc aaagagaaaa tgaacaattg 2940
aaaaaggcat caggaatact gactagtgaa aaaatggcta ctattgagga agaaaataga 3000
aacttaaagg ctgaactaga aaagcttaaa gctcactttg gacgtcagtt gagtatgcag 3060
tttgaatcta agaacaaagg tactgagaaa attgttgccg aaaatgaacg gcttcggaaa 3120
gaacttaaga aagaaataga agcctctgag aaactgcgga tagctaagaa caacttagag 3180
ctggtgaacg acaagatggc agctcaactc gaagaaactg ggaagagact acagtttgca 3240
gaaagtagag ccccacagct ggaaggtgct gacagcaaga gctggaagtc aattgtggtc 3300
tcaagagtgt atgagaccaa gatgaaagag cttgaaagtg acattgccaa aaagaatcaa 3360
agtatcactg accttaaaca gcttgtaaga gaagcaacag agagagaaca gaaagctaag 3420
aaatacactg aagaccttga acaacagatt gagatcctca aaaatgttcc tgaaggtgcc 3480
gagacagagc aagagcttat acgggaactc cagcttctta gattagccaa taatcagatg 3540
gataaagaaa gggcagaatt aatccatcag atagaaatta acaaggacca aaccagagct 3600
gacagtagca tacctgattc tgatcaacta aaggaaaaga taaatgacct ggagacacaa 3660
ctcagaaagt tggagctaga aaagcaacat tcgaaggagg aagttaaaaa gctgaaaaaa 3720
gaactggaaa attttgatcc ttcatttttt gaagaaattg aagacctgaa gtataattat 3780
aaggaagaag tgaaaaagaa tatcctatta gaagagaagc taaaaaaact gtcggaacag 3840
tttggatttg aactgcctag tcctcttgct gcttctgaac actcggaaga tggagaaagt 3900
cctcatagtt tccctattta ttag 3924

<210> SEQ ID NO 29
<211> LENGTH: 1307
<212> TYPE: PRT
<213> ORGANISM: Mus musculus

<400> SEQUENCE: 29

-continued

```
Gln Gln Gln Ser Arg Glu Lys Glu Val Glu Ser Leu Arg Thr Gln Leu
1               5                   10                  15

Leu Asp Phe Gln Ala Gln Ser Asp Glu Lys Ala Leu Ile Ala Lys Leu
            20                  25                  30

His Gln His Val Val Ser Leu Gln Ile Ser Glu Ala Thr Ala Leu Gly
        35                  40                  45

Lys Leu Glu Ser Val Thr Ser Lys Leu Gln Lys Met Glu Ala Tyr Asn
    50                  55                  60

Leu Arg Leu Glu Gln Lys Leu Asp Glu Lys Glu Gln Ala Leu Tyr Tyr
65                  70                  75                  80

Ala Arg Leu Glu Gly Arg Asn Arg Ala Lys His Leu Arg Gln Thr Ile
                85                  90                  95

Gln Ser Leu Arg Arg Gln Phe Ser Gly Ala Leu Pro Leu Ala Gln Gln
            100                 105                 110

Glu Lys Phe Ser Lys Thr Met Ile Gln Leu Gln Asn Asp Lys Leu Lys
        115                 120                 125

Ile Met Gln Glu Met Lys Asn Ser Gln Gln Glu His Arg Asn Met Glu
    130                 135                 140

Asn Lys Thr Leu Glu Leu Glu Leu Lys Leu Lys Gly Leu Glu Glu Leu
145                 150                 155                 160

Ile Ser Thr Leu Lys Asp Ala Arg Gly Ala Gln Lys Val Ile Asn Trp
                165                 170                 175

His Val Lys Ile Glu Glu Leu Arg Leu Gln Glu Leu Lys Leu Asn Arg
            180                 185                 190

Glu Leu Val Lys Gly Lys Glu Glu Ile Lys Tyr Leu Asn Asn Ile Ile
        195                 200                 205

Ser Glu Tyr Glu His Thr Ile Asn Ser Leu Glu Glu Glu Ile Val Gln
    210                 215                 220

Gln Ser Lys Phe His Glu Glu Arg Gln Met Ala Trp Asp Gln Arg Glu
225                 230                 235                 240

Val Glu Leu Glu Arg Gln Leu Asp Ile Phe Asp His Gln Gln Asn Glu
                245                 250                 255

Ile Leu Ser Ala Ala Gln Lys Phe Glu Asp Ser Thr Gly Ser Met Pro
            260                 265                 270

Asp Pro Ser Leu Pro Leu Pro Asn Gln Leu Glu Ile Ala Leu Arg Lys
        275                 280                 285

Ile Lys Glu Asn Ile Gln Val Ile Leu Lys Thr Gln Ala Thr Cys Lys
    290                 295                 300

Ser Leu Glu Glu Lys Leu Lys Glu Lys Glu Ser Ala Leu Arg Leu Ala
305                 310                 315                 320

Glu Gln Asn Ile Leu Ser Arg Asp Lys Val Ile Asn Glu Leu Arg Leu
                325                 330                 335

Arg Leu Pro Ala Thr Ala Asp Arg Glu Lys Leu Ile Ala Glu Leu Glu
            340                 345                 350

Arg Lys Glu Leu Glu Pro Lys Ser His His Thr Met Lys Ile Ala His
        355                 360                 365

Gln Thr Ile Ala Asn Met Gln Ala Arg Leu Asn His Lys Glu Glu Val
    370                 375                 380

Leu Lys Lys Tyr Gln His Leu Leu Glu Lys Ala Arg Glu Glu Gln Arg
385                 390                 395                 400

Glu Ile Val Lys Lys His Glu Glu Asp Leu His Val Leu His His Lys
                405                 410                 415
```

-continued

```
Leu Glu Gln Gln Ala Asp Asn Ser Leu Asn Lys Phe Arg Gln Thr Ala
            420                 425                 430

Gln Asp Leu Leu Lys Gln Ser Pro Ala Pro Val Pro Thr Asn Lys His
        435                 440                 445

Phe Ile Arg Leu Ala Glu Met Glu Gln Thr Val Ala Glu Gln Asp Asp
    450                 455                 460

Ser Leu Ser Ser Leu Leu Thr Lys Leu Lys Lys Val Ser Lys Asp Leu
465                 470                 475                 480

Glu Lys Gln Lys Glu Ile Thr Glu Leu Lys Val Arg Glu Phe Glu Asn
                485                 490                 495

Thr Lys Leu Arg Leu Gln Glu Thr His Ala Ser Glu Val Lys Lys Val
            500                 505                 510

Lys Ala Glu Val Glu Asp Leu Arg His Ala Leu Ala Gln Ala His Lys
        515                 520                 525

Asp Ser Gln Ser Leu Lys Ser Glu Leu Gln Ala Gln Lys Glu Ala Asn
    530                 535                 540

Ser Arg Ala Pro Thr Thr Thr Met Arg Asn Leu Val Asp Arg Leu Lys
545                 550                 555                 560

Ser Gln Leu Ala Leu Lys Glu Lys Gln Gln Lys Ala Leu Ser Arg Ala
                565                 570                 575

Leu Leu Glu Leu Arg Ser Glu Met Thr Ala Ala Ala Glu Glu Arg Ile
            580                 585                 590

Ile Ala Val Thr Ser Gln Lys Glu Ala Asn Leu Asn Val Gln Gln Val
        595                 600                 605

Val Glu Arg His Thr Arg Glu Leu Lys Ser Gln Ile Glu Asp Leu Asn
    610                 615                 620

Glu Asn Leu Leu Lys Leu Lys Glu Ala Leu Lys Thr Ser Lys Asn Lys
625                 630                 635                 640

Glu Asn Ser Leu Ala Asp Asp Leu Asn Glu Leu Asn Asn Glu Leu Gln
                645                 650                 655

Lys Lys Gln Lys Ala Tyr Asn Lys Ile Leu Arg Glu Lys Asp Gly Ile
            660                 665                 670

Asp Gln Glu Asn Asp Glu Leu Arg Arg Gln Ile Lys Arg Leu Ser Ser
        675                 680                 685

Gly Leu Gln Ser Lys Thr Leu Ile Asp Asn Lys Gln Ser Leu Ile Asp
    690                 695                 700

Glu Leu Gln Lys Lys Val Lys Lys Leu Glu Ser Gln Leu Glu Arg Lys
705                 710                 715                 720

Val Asp Asp Val Asp Ile Lys Pro Val Lys Glu Lys Ser Ser Lys Glu
                725                 730                 735

Glu Leu Ile Arg Trp Glu Glu Gly Lys Lys Trp Gln Thr Lys Val Glu
            740                 745                 750

Gly Leu Arg Asn Arg Leu Lys Glu Lys Glu Gly Glu Ala His Gly Leu
        755                 760                 765

Ala Lys Gln Leu Asn Thr Leu Lys Glu Leu Phe Ala Lys Ala Asp Lys
    770                 775                 780

Glu Lys Leu Thr Leu Gln Lys Lys Leu Lys Thr Thr Gly Met Thr Val
785                 790                 795                 800

Asp Gln Val Leu Gly Val Arg Ala Leu Glu Ser Glu Lys Glu Leu Glu
                805                 810                 815

Glu Leu Lys Lys Lys Asn Leu Asp Leu Glu Asn Asp Ile Leu Tyr Met
            820                 825                 830

Arg Thr Gln Gln Ala Leu Pro Arg Asp Ser Val Val Glu Asp Leu His
```

-continued

```
        835                 840                 845

Leu Gln Asn Lys Tyr Leu Gln Glu Lys Leu His Thr Leu Glu Lys Lys
    850                 855                 860

Leu Ser Lys Glu Lys Tyr Ser Gln Ser Leu Thr Ser Glu Ile Glu Ser
865                 870                 875                 880

Asp Asp His Cys Gln Lys Glu Gln Glu Leu Gln Lys Glu Asn Leu Lys
                885                 890                 895

Leu Ser Ser Glu Asn Ile Glu Leu Lys Phe Gln Leu Glu Gln Ala Asn
            900                 905                 910

Lys Asp Leu Pro Arg Leu Lys Asn Gln Val Lys Asp Leu Lys Glu Met
        915                 920                 925

Cys Glu Phe Leu Lys Lys Gly Lys Leu Glu Leu Glu Arg Lys Leu Gly
    930                 935                 940

Gln Val Arg Gly Ala Gly Arg Ser Gly Lys Thr Ile Pro Glu Leu Glu
945                 950                 955                 960

Lys Thr Ile Gly Leu Met Lys Lys Val Val Glu Lys Val Gln Arg Glu
                965                 970                 975

Asn Glu Gln Leu Lys Lys Ala Ser Gly Ile Leu Thr Ser Glu Lys Met
            980                 985                 990

Ala Thr Ile Glu Glu Glu Asn Arg  Asn Leu Lys Ala Glu  Leu Glu Lys
        995                 1000                 1005

Leu Lys  Ala His Phe Gly Arg  Gln Leu Ser Met Gln  Phe Glu Ser
    1010                 1015                 1020

Lys Asn  Lys Gly Thr Glu Lys  Ile Val Ala Glu Asn  Glu Arg Leu
    1025                 1030                 1035

Arg Lys  Glu Leu Lys Lys Glu  Ile Glu Ala Ser Glu  Lys Leu Arg
    1040                 1045                 1050

Ile Ala  Lys Asn Asn Leu Glu  Leu Val Asn Asp Lys  Met Ala Ala
    1055                 1060                 1065

Gln Leu  Glu Glu Thr Gly Lys  Arg Leu Gln Phe Ala  Glu Ser Arg
    1070                 1075                 1080

Ala Pro  Gln Leu Glu Gly Ala  Asp Ser Lys Ser Trp  Lys Ser Ile
    1085                 1090                 1095

Val Val  Ser Arg Val Tyr Glu  Thr Lys Met Lys Glu  Leu Glu Ser
    1100                 1105                 1110

Asp Ile  Ala Lys Lys Asn Gln  Ser Ile Thr Asp Leu  Lys Gln Leu
    1115                 1120                 1125

Val Arg  Glu Ala Thr Glu Arg  Glu Gln Lys Ala Lys  Lys Tyr Thr
    1130                 1135                 1140

Glu Asp  Leu Glu Gln Gln Ile  Glu Ile Leu Lys Asn  Val Pro Glu
    1145                 1150                 1155

Gly Ala  Glu Thr Glu Gln Glu  Leu Ile Arg Glu Leu  Gln Leu Leu
    1160                 1165                 1170

Arg Leu  Ala Asn Asn Gln Met  Asp Lys Glu Arg Ala  Glu Leu Ile
    1175                 1180                 1185

His Gln  Ile Glu Ile Asn Lys  Asp Gln Thr Arg Ala  Asp Ser Ser
    1190                 1195                 1200

Ile Pro  Asp Ser Asp Gln Leu  Lys Glu Lys Ile Asn  Asp Leu Glu
    1205                 1210                 1215

Thr Gln  Leu Arg Lys Leu Glu  Leu Glu Lys Gln His  Ser Lys Glu
    1220                 1225                 1230

Glu Val  Lys Lys Leu Lys Lys  Glu Leu Glu Asn Phe  Asp Pro Ser
    1235                 1240                 1245
```

```
Phe Phe  Glu Glu Ile Glu Asp  Leu Lys Tyr Asn Tyr  Lys Glu Glu
    1250                1255                1260

Val Lys  Lys Asn Ile Leu Leu  Glu Glu Lys Leu Lys  Lys Leu Ser
    1265                1270                1275

Glu Gln  Phe Gly Phe Glu Leu  Pro Ser Pro Leu Ala  Ala Ser Glu
    1280                1285                1290

His Ser  Glu Asp Gly Glu Ser  Pro His Ser Phe Pro  Ile Tyr
    1295                1300                1305
```

<210> SEQ ID NO 30
<211> LENGTH: 3924
<212> TYPE: DNA
<213> ORGANISM: Mus musculus

<400> SEQUENCE: 30

```
ctaataaata gggaaactat gaggactttc tccatcttcc gagtgttcag aagcagcaag     60
aggactaggc agttcaaatc caaactgttc cgacagtttt tttagcttct cttctaatag    120
gatattcttt ttcacttctt ccttataatt atacttcagg tcttcaattt cttcaaaaaa    180
tgaaggatca aaattttcca gttctttttt cagcttttta acttcctcct tcgaatgttg    240
cttttctagc tccaactttc tgagttgtgt ctccaggtca tttatctttt cctttagttg    300
atcagaatca ggtatgctac tgtcagctct ggtttggtcc ttgttaattt ctatctgatg    360
gattaattct gccctttctt tatccatctg attattggct aatctaagaa gctggagttc    420
ccgtataagc tcttgctctg tctcggcacc ttcaggaaca tttttgagga tctcaatctg    480
ttgttcaagg tcttcagtgt atttcttagc tttctgttct ctctctgttg cttctcttac    540
aagctgttta aggtcagtga tactttgatt ctttttggca atgtcacttt caagctcttt    600
catcttggtc tcatacactc ttgagaccac aattgacttc cagctcttgc tgtcagcacc    660
ttccagctgt ggggctctac tttctgcaaa ctgtagtctc ttcccagttt cttcgagttg    720
agctgccatc ttgtcgttca ccagctctaa gttgttctta gctatccgca gtttctcaga    780
ggcttctatt tctttcttaa gttctttccg aagccgttca ttttcggcaa caattttctc    840
agtacctttg ttcttagatt caaactgcat actcaactga cgtccaaagt gagctttaag    900
cttttctagt tcagccttta agtttctatt ttcttcctca atagtagcca ttttttcact    960
agtcagtatt cctgatgcct ttttcaattg ttcattttct ctttggactt tttcaactac   1020
tttcttcatt aacccaatgg ttttttctag ttctgggatt gtcttcccac ttctaccagc   1080
ccctctgacc tgaccaagct tccgctcaag ttccagtttt cctttcttaa gaaattcaca   1140
catttccttc aaatctttca cttgattctt tagtcttggc aaatctttat ttgcttgttc   1200
aagttgaaat ttcagctcga tgttttcaga tgacaacttc aaattttcct tctgaagttc   1260
ttgttctttt tgacagtgat catctgactc tatttctgaa gtcaaagact gagaatattt   1320
ctcctttgaa agtttttttt ctaaagtatg aagtttttct tgaaggtatt tattttgtaa   1380
atgtaagtct tccacaacag aatctcgtgg aagagcctgc tgggtcctca tgtataaatat  1440
gtcattttct aggtccagat ttttcttttt tagctcttcc aactcttttt cagattccaa   1500
agctcgcact cctaaaacct ggtcaacagt cattcctgtt gttttcagtt tcttctgcaa   1560
agtaagtttc tctttatcag ctttggcaaa aagttccttt aaggtattca gctgctttgc   1620
caggccgtgg gcttctcctt ccttctcctt tagtctgttt cgtagtccct ctactttggt   1680
ttgccatttc ttaccttctt cccacctaat taattcttct ttactactct tttccttcac   1740
```

-continued

```
cggctttatg tctacgtcat ccacctttct ttccagttgg ctttcaagtt ttttaacttt   1800

cttttgaagt tcatcgatta aactttgctt gttatctatc aaagttttgc tctgcagtcc   1860

actggacagt cttttaatct gtcttctcag ttcatcattt tcttgatcaa ttccatcttt   1920

ctctctaagg attttattat aagctttttg cttttttttgc agttcattat ttaattcatt   1980

taaatcatca gctagtgaat tttctttgtt cttacttgtt ttaagagctt ctttcaattt   2040

taaaagattt tcatttaaat cttcaatttg tgactttagc tctctagtat ggcgctcaac   2100

aacttgttga acattgagat ttgcctcttt ttgagaagtt acagcgatta tacgttcctc   2160

agctgctgct gtcatttccg accgaagttc caacagggct cgactaagtg ccttttgttg   2220

cttctctttc aaggctagtt ggctctttag cctgtctaca agattcctca ttgtggttgt   2280

tggagctctg gagtttgctt ctttctgagc ctggagttca gactttaaac tctgggagtc   2340

cttgtgtgct tgggctagag catgccttaa gtcctctacc tctgctttca ctttctttac   2400

ctcactggca tgagtttctt ggagccgtag tttggtattt tcaaactctc tgacttttaa   2460

ctcagtgatt tctttttgtt tttccaaatc ttttgatact ttctttagtt tggtcaaaag   2520

tgaggacaga gagtcatctt gttctgctac tgtctgctcc atctcggcca gacgaatgaa   2580

atgtttgttg gtgggaactg gagcaggaga ctgcttaagt aaatcctgag ctgtctgtct   2640

gaatttattg agtgaattat cggcctgttg ttctaatttg tgatgaagaa catgaaggtc   2700

ttcctcatgc ttcttaacaa tttctctttg ctcctctctg gccttctcca gaaggtgctg   2760

gtatttcttc aatacttctt ccttgtgatt taaccttgcc tgcatgttgg caatagtttg   2820

gtgggcaatt ttcattgtgt gatgagattt cggctccagc tcttttcttt ctagctcagc   2880

tataagtttt tctcgatcag ccgtggcagg caatcgaagc ctcagttcat tgattacttt   2940

gtctcttgac agaatatttt gctctgccaa ccgtaaagca gattcttttt cttttagttt   3000

ctcttctagt gacttgcaag ttgcttgtgt tttaagaatt acttgaatat tctccttaat   3060

ttttcttaga gcaatttcaa gttggtttgg aagaggcaag ctggggtctg gcattgatcc   3120

tgtagagtct tcaaactttt gtgctgcact gagtatttca ttttgctgat gatcaaaaat   3180

gtctaactgg cgttccagct caacttctct ttgatcccaa gccatctgtc tttcttcatg   3240

gaacttgctt tgctgaacaa tttcttcctc tagactgttg attgtatgct catattcaga   3300

gatgatatta ttcaaatatt tgatttcttc tttacccttg actagttctc tatttagctt   3360

aagttcttgg aggcgaagtt cttctatttt cacatgccaa ttgattacct tctgggctcc   3420

cctggcatcc tttaaagtac tgatcaattc ttctaagcct tttaatttta attccaactc   3480

cagtgttttg ttttccatat ttctgtgttc ctgttgcgaa ttcttcattt cttgcattat   3540

cttaagtttg tcattttgca actgaatcat cgttttggag aacttttcct gctgtgctaa   3600

gggtagagct ccactgaact gtcttcgaag cgactgaatg gtttggcgca ggtgttttgc   3660

tctgtttcta ccttccaaac gagcatagta gagcgcctgc tctttttcat ccagtttctg   3720

ttctaagcgc aaattgtagg cttccatctt ctggagtttg gacgtaactg actctaactt   3780

accgagggca gtggcctcac taatttgaag agagacaaca tgttggtgca atttggcaat   3840

tagagccttt tcgtcagatt gtgcctggaa gtccagcagc tgcgttctga gggattccac   3900

ttccttttcc ctggactgtt gttg                                           3924
```

```
<210> SEQ ID NO 31
<211> LENGTH: 3924
<212> TYPE: DNA
<213> ORGANISM: Homo sapiens
```

<400> SEQUENCE: 31

```
caacaatcta gggacaagga agtagagtcc ctcagaatgc aactgctaga ctatcaggca     60
cagtctgatg aaaagtcgct cattgccaag ttgcaccaac ataatgtctc tcttcaactg    120
agtgaggcta ctgctcttgg taagttggag tcaattacat ctaaactgca gaagatggag    180
gcctacaact tgcgcttaga gcagaaactt gatgaaaaag aacaggctct ctattatgct    240
cgtttggagg gaagaaacag agcaaaaacat ctgcgccaaa caattcagtc tctacgacga    300
cagtttagtg gagctttacc cttggcacaa caggaaaagt tctccaaaac aatgattcaa    360
ctacaaaatg acaaacttaa gataatgcaa gaaatgaaaa attctcaaca agaacataga    420
aatatggaga acaaaacatt ggagatggaa ttaaaattaa agggcctgga agagttaata    480
agcactttaa aggataccaa aggagcccaa aaggtaatca actggcatat gaaaatagaa    540
gaacttcgtc ttcaagaact taaactaaat cgggaattag tcaaggataa agaagaaata    600
aaatatttga ataacataat ttctgaatat gaacgtacaa tcagcagtct tgaagaagaa    660
attgtgcaac agaacaagtt tcatgaagaa agacaaatgg cctgggatca aagagaagtt    720
gacctggaac gccaactaga catttttgac cgtcagcaaa atgaaatact aaatgcggca    780
caaaagtttg aagaagctac aggatcaatc cctgacccta gtttgcccct tccaaatcaa    840
cttgagatcg ctctaaggaa aattaaggag aacattcgaa taattctaga aacacgggca    900
acttgcaaat cactagaaga gaaactaaaa gagaaagaat ctgctttaag gttagcagaa    960
caaaatatac tgtcaagaga caaagtaatc aatgaactga ggcttcgatt gcctgccact   1020
gcagaaagag aaaagctcat agctgagcta ggcagaaaag agatggaacc aaaatctcac   1080
cacacattga aaattgctca tcaaaccatt gcaaacatgc aagcaaggtt aaatcaaaaa   1140
gaagaagtat taaagaagta tcaacgtctt ctagaaaaag ccagagagga gcaaagagaa   1200
attgtgaaga aacatgagga agaccttcat attcttcatc acagattaga actacaggct   1260
gatagttcac taaataaatt caaacaaacg gcttgggatt taatgaaaca gtctcccact   1320
ccagttccta ccaacaagca ttttattcgt ctggctgaga tggaacagac agtagcagaa   1380
caagatgact ctctttcctc actcttggtc aaactaaaga aagtatcaca agatttggag   1440
agacaaagag aaatcactga attaaaagta aaagaatttg aaaatatcaa attacagctt   1500
caagaaaacc atgaagatga agtgaaaaaa gtaaaagcgg aagtagagga tttaaagtat   1560
cttctggacc agtcacaaaa ggagtcacag tgtttaaaat ctgaacttca ggctcaaaaa   1620
gaagcaaatt caagagctcc aacaactaca atgagaaatc tagtagaacg gctaaagagc   1680
caattagcct tgaaggagaa acaacagaaa gcacttagtc gggcactttt agaactccgg   1740
gcagaaatga cagcagctgc tgaagaacgt attatttctg caacttctca aaaagaggcc   1800
catctcaatg ttcaacaaat cgttgatcga catactagag agctaaagac acaagttgaa   1860
gatttaaatg aaaatctttt aaaattgaaa gaagcactta aaacaagtaa aaacagagaa   1920
aactcactaa ctgataattt gaatgactta aataatgaac tgcaaaagaa acaaaaagcc   1980
tataataaaa tacttagaga gaaagaggaa attgatcaag agaatgatga actgaaaagg   2040
caaattaaaa gactaaccag tggattacag ggcaaacccc tgacagataa taaacaaagt   2100
ctaattgaag aactccaaag gaaagttaaa aaactagaga accaattaga gggaaaggtg   2160
gaggaagtag acctaaaacc tatgaaagaa aagaatgcta aagaagaatt aattaggtgg   2220
gaagaaggta aaaagtggca agccaaaata gaaggaattc gaaacaagtt aaaagagaaa   2280
```

-continued

```
gagggggaag tctttacttt aacaaagcag ttgaatactt tgaaggatct ttttgccaaa   2340
gccgataaag agaaacttac tttgcagagg aaactaaaaa caactggcat gactgttgat   2400
caggttttgg gaatacgagc tttggagtca gaaaaagaat tggaagaatt aaaaaagaga   2460
aatcttgact tagaaaatga tatattgtat atgagggccc accaagctct tcctcgagat   2520
tctgttgtag aagatttaca tttacaaaat agatacctcc aagaaaaact tcatgcttta   2580
gaaaaacagt tttcaaagga tacatattct aagccttcaa tttcaggaat agagtcagat   2640
gatcattgtc agagagaaca ggagcttcag aaggaaaact tgaagttgtc atctgaaaat   2700
attgaactga aatttcagct tgaacaagca aataaagatt tgccaagatt aaagaatcaa   2760
gtcagagatt tgaaggaaat gtgtgaattt cttaagaaag aaaaagcaga agttcagcgg   2820
aaacttggcc atgttagagg gtctggtaga agtggaaaga caatcccaga actggaaaaa   2880
accattggtt taatgaaaaa agtagttgaa aaagtccaga gagaaaatga acagttgaaa   2940
aaagcatcag gaatattgac tagtgaaaaa atggctaata ttgagcagga aaatgaaaaa   3000
ttgaaggctg aattagaaaa acttaaagct catcttgggc atcagttgag catgcactat   3060
gaatccaaga ccaaaggcac agaaaaaatt attgctgaaa atgaaaggct tcgtaaagaa   3120
cttaaaaaag aaactgatgc tgcagagaaa ttacggatag caaagaataa tttagagata   3180
ttaaatgaga agatgacagt tcaactagaa gagactggta agagattgca gtttgcagaa   3240
agcagaggtc cacagcttga aggtgctgac agtaagagct ggaaatccat tgtggttaca   3300
agaatgtatg aaaccaagtt aaaagaattg gaaactgata ttgccaaaaa aaatcaaagc   3360
attactgacc ttaaacagct tgtaaaagaa gcaacagaga gagaacaaaa agttaacaaa   3420
tacaatgaag accttgaaca acagattaag attcttaaac atgttcctga aggtgctgag   3480
acagagcaag gccttaaacg ggagcttcaa gttcttagat tagctaatca tcagctggat   3540
aaagagaaag cagaattaat ccatcagata gaagctaaca aggaccaaag tggagctgaa   3600
agcaccatac ctgatgctga tcaactaaag gaaaaaataa aagatctaga gacacagctc   3660
aaaatgtcag atctagaaaa gcagcatttg aaggaggaaa taaagaagct gaaaaaagaa   3720
ctggaaaatt ttgatccttc atttttgaa gaaattgaag atcttaagta taattacaag    3780
gaagaagtga agaagaatat tctcttagaa gagaaggtaa aaaaactttc agaacaattg   3840
ggagttgaat taactagccc tgttgctgct tctgaagagt ttgaagatga agaagaaagt   3900
cctgttaatt tccccattta ctaa                                          3924
```

<210> SEQ ID NO 32
<211> LENGTH: 1307
<212> TYPE: PRT
<213> ORGANISM: Homo sapiens

<400> SEQUENCE: 32

```
Gln Gln Ser Arg Asp Lys Glu Val Glu Ser Leu Arg Met Gln Leu Leu
1               5                   10                  15

Asp Tyr Gln Ala Gln Ser Asp Glu Lys Ser Leu Ile Ala Lys Leu His
            20                  25                  30

Gln His Asn Val Ser Leu Gln Leu Ser Glu Ala Thr Ala Leu Gly Lys
        35                  40                  45

Leu Glu Ser Ile Thr Ser Lys Leu Gln Lys Met Glu Ala Tyr Asn Leu
    50                  55                  60

Arg Leu Glu Gln Lys Leu Asp Glu Lys Glu Gln Ala Leu Tyr Tyr Ala
65                  70                  75                  80
```

-continued

```
Arg Leu Glu Gly Arg Asn Arg Ala Lys His Leu Arg Gln Thr Ile Gln
                85                  90                  95

Ser Leu Arg Arg Gln Phe Ser Gly Ala Leu Pro Leu Ala Gln Gln Glu
            100                 105                 110

Lys Phe Ser Lys Thr Met Ile Gln Leu Gln Asn Asp Lys Leu Lys Ile
        115                 120                 125

Met Gln Glu Met Lys Asn Ser Gln Gln Glu His Arg Asn Met Glu Asn
    130                 135                 140

Lys Thr Leu Glu Met Glu Leu Lys Leu Lys Gly Leu Glu Glu Leu Ile
145                 150                 155                 160

Ser Thr Leu Lys Asp Thr Lys Gly Ala Gln Lys Val Ile Asn Trp His
                165                 170                 175

Met Lys Ile Glu Glu Leu Arg Leu Gln Glu Leu Lys Leu Asn Arg Glu
            180                 185                 190

Leu Val Lys Asp Lys Glu Glu Ile Lys Tyr Leu Asn Asn Ile Ile Ser
        195                 200                 205

Glu Tyr Glu Arg Thr Ile Ser Ser Leu Glu Glu Glu Ile Val Gln Gln
    210                 215                 220

Asn Lys Phe His Glu Glu Arg Gln Met Ala Trp Asp Gln Arg Glu Val
225                 230                 235                 240

Asp Leu Glu Arg Gln Leu Asp Ile Phe Asp Arg Gln Gln Asn Glu Ile
                245                 250                 255

Leu Asn Ala Ala Gln Lys Phe Glu Glu Ala Thr Gly Ser Ile Pro Asp
            260                 265                 270

Pro Ser Leu Pro Leu Pro Asn Gln Leu Glu Ile Ala Leu Arg Lys Ile
        275                 280                 285

Lys Glu Asn Ile Arg Ile Ile Leu Glu Thr Arg Ala Thr Cys Lys Ser
    290                 295                 300

Leu Glu Glu Lys Leu Lys Glu Lys Glu Ser Ala Leu Arg Leu Ala Glu
305                 310                 315                 320

Gln Asn Ile Leu Ser Arg Asp Lys Val Ile Asn Glu Leu Arg Leu Arg
                325                 330                 335

Leu Pro Ala Thr Ala Glu Arg Glu Lys Leu Ile Ala Glu Leu Gly Arg
            340                 345                 350

Lys Glu Met Glu Pro Lys Ser His His Thr Leu Lys Ile Ala His Gln
        355                 360                 365

Thr Ile Ala Asn Met Gln Ala Arg Leu Asn Gln Lys Glu Glu Val Leu
    370                 375                 380

Lys Lys Tyr Gln Arg Leu Leu Glu Lys Ala Arg Glu Glu Gln Arg Glu
385                 390                 395                 400

Ile Val Lys Lys His Glu Glu Asp Leu His Ile Leu His His Arg Leu
                405                 410                 415

Glu Leu Gln Ala Asp Ser Ser Leu Asn Lys Phe Lys Gln Thr Ala Trp
            420                 425                 430

Asp Leu Met Lys Gln Ser Pro Thr Pro Val Pro Thr Asn Lys His Phe
        435                 440                 445

Ile Arg Leu Ala Glu Met Glu Gln Thr Val Ala Glu Gln Asp Asp Ser
    450                 455                 460

Leu Ser Ser Leu Leu Val Lys Leu Lys Lys Val Ser Gln Asp Leu Glu
465                 470                 475                 480

Arg Gln Arg Glu Ile Thr Glu Leu Lys Val Lys Glu Phe Glu Asn Ile
                485                 490                 495

Lys Leu Gln Leu Gln Glu Asn His Glu Asp Glu Val Lys Lys Val Lys
```

-continued

```
            500                 505                 510

Ala Glu Val Glu Asp Leu Lys Tyr Leu Leu Asp Gln Ser Gln Lys Glu
        515                 520                 525

Ser Gln Cys Leu Lys Ser Glu Leu Gln Ala Gln Lys Glu Ala Asn Ser
    530                 535                 540

Arg Ala Pro Thr Thr Thr Met Arg Asn Leu Val Glu Arg Leu Lys Ser
545                 550                 555                 560

Gln Leu Ala Leu Lys Glu Lys Gln Gln Lys Ala Leu Ser Arg Ala Leu
                565                 570                 575

Leu Glu Leu Arg Ala Glu Met Thr Ala Ala Ala Glu Glu Arg Ile Ile
            580                 585                 590

Ser Ala Thr Ser Gln Lys Glu Ala His Leu Asn Val Gln Gln Ile Val
        595                 600                 605

Asp Arg His Thr Arg Glu Leu Lys Thr Gln Val Glu Asp Leu Asn Glu
    610                 615                 620

Asn Leu Leu Lys Leu Lys Glu Ala Leu Lys Thr Ser Lys Asn Arg Glu
625                 630                 635                 640

Asn Ser Leu Thr Asp Asn Leu Asn Asp Leu Asn Asn Glu Leu Gln Lys
                645                 650                 655

Lys Gln Lys Ala Tyr Asn Lys Ile Leu Arg Glu Lys Glu Glu Ile Asp
            660                 665                 670

Gln Glu Asn Asp Glu Leu Lys Arg Gln Ile Lys Arg Leu Thr Ser Gly
        675                 680                 685

Leu Gln Gly Lys Pro Leu Thr Asp Asn Lys Gln Ser Leu Ile Glu Glu
    690                 695                 700

Leu Gln Arg Lys Val Lys Lys Leu Glu Asn Gln Leu Glu Gly Lys Val
705                 710                 715                 720

Glu Glu Val Asp Leu Lys Pro Met Lys Glu Lys Asn Ala Lys Glu Glu
                725                 730                 735

Leu Ile Arg Trp Glu Glu Gly Lys Lys Trp Gln Ala Lys Ile Glu Gly
            740                 745                 750

Ile Arg Asn Lys Leu Lys Glu Lys Glu Gly Glu Val Phe Thr Leu Thr
        755                 760                 765

Lys Gln Leu Asn Thr Leu Lys Asp Leu Phe Ala Lys Ala Asp Lys Glu
    770                 775                 780

Lys Leu Thr Leu Gln Arg Lys Leu Lys Thr Thr Gly Met Thr Val Asp
785                 790                 795                 800

Gln Val Leu Gly Ile Arg Ala Leu Glu Ser Glu Lys Glu Leu Glu Glu
                805                 810                 815

Leu Lys Lys Arg Asn Leu Asp Leu Glu Asn Asp Ile Leu Tyr Met Arg
            820                 825                 830

Ala His Gln Ala Leu Pro Arg Asp Ser Val Val Glu Asp Leu His Leu
        835                 840                 845

Gln Asn Arg Tyr Leu Gln Glu Lys Leu His Ala Leu Glu Lys Gln Phe
    850                 855                 860

Ser Lys Asp Thr Tyr Ser Lys Pro Ser Ile Ser Gly Ile Glu Ser Asp
865                 870                 875                 880

Asp His Cys Gln Arg Glu Gln Glu Leu Gln Lys Glu Asn Leu Lys Leu
                885                 890                 895

Ser Ser Glu Asn Ile Glu Leu Lys Phe Gln Leu Glu Gln Ala Asn Lys
            900                 905                 910

Asp Leu Pro Arg Leu Lys Asn Gln Val Arg Asp Leu Lys Glu Met Cys
        915                 920                 925
```

```
Glu Phe Leu Lys Lys Glu Lys Ala Glu Val Gln Arg Lys Leu Gly His
    930                 935                 940

Val Arg Gly Ser Gly Arg Ser Gly Lys Thr Ile Pro Glu Leu Glu Lys
945                 950                 955                 960

Thr Ile Gly Leu Met Lys Lys Val Val Glu Lys Val Gln Arg Glu Asn
                965                 970                 975

Glu Gln Leu Lys Lys Ala Ser Gly Ile Leu Thr Ser Glu Lys Met Ala
            980                 985                 990

Asn Ile Glu Gln Glu Asn Glu Lys  Leu Lys Ala Glu Leu  Glu Lys Leu
        995                 1000                 1005

Lys Ala  His Leu Gly His Gln  Leu Ser Met His Tyr  Glu Ser Lys
    1010                 1015                 1020

Thr Lys  Gly Thr Glu Lys Ile  Ile Ala Glu Asn Glu  Arg Leu Arg
    1025                 1030                 1035

Lys Glu  Leu Lys Lys Glu Thr  Asp Ala Ala Glu Lys  Leu Arg Ile
    1040                 1045                 1050

Ala Lys  Asn Asn Leu Glu Ile  Leu Asn Glu Lys Met  Thr Val Gln
    1055                 1060                 1065

Leu Glu  Glu Thr Gly Lys Arg  Leu Gln Phe Ala Glu  Ser Arg Gly
    1070                 1075                 1080

Pro Gln  Leu Glu Gly Ala Asp  Ser Lys Ser Trp Lys  Ser Ile Val
    1085                 1090                 1095

Val Thr  Arg Met Tyr Glu Thr  Lys Leu Lys Glu Leu  Glu Thr Asp
    1100                 1105                 1110

Ile Ala  Lys Lys Asn Gln Ser  Ile Thr Asp Leu Lys  Gln Leu Val
    1115                 1120                 1125

Lys Glu  Ala Thr Glu Arg Glu  Gln Lys Val Asn Lys  Tyr Asn Glu
    1130                 1135                 1140

Asp Leu  Glu Gln Gln Ile Lys  Ile Leu Lys His Val  Pro Glu Gly
    1145                 1150                 1155

Ala Glu  Thr Glu Gln Gly Leu  Lys Arg Glu Leu Gln  Val Leu Arg
    1160                 1165                 1170

Leu Ala  Asn His Gln Leu Asp  Lys Glu Lys Ala Glu  Leu Ile His
    1175                 1180                 1185

Gln Ile  Glu Ala Asn Lys Asp  Gln Ser Gly Ala Glu  Ser Thr Ile
    1190                 1195                 1200

Pro Asp  Ala Asp Gln Leu Lys  Glu Lys Ile Lys Asp  Leu Glu Thr
    1205                 1210                 1215

Gln Leu  Lys Met Ser Asp Leu  Glu Lys Gln His Leu  Lys Glu Glu
    1220                 1225                 1230

Ile Lys  Lys Leu Lys Lys Glu  Leu Glu Asn Phe Asp  Pro Ser Phe
    1235                 1240                 1245

Phe Glu  Glu Ile Glu Asp Leu  Lys Tyr Asn Tyr Lys  Glu Glu Val
    1250                 1255                 1260

Lys Lys  Asn Ile Leu Leu Glu  Glu Lys Val Lys Lys  Leu Ser Glu
    1265                 1270                 1275

Gln Leu  Gly Val Glu Leu Thr  Ser Pro Val Ala Ala  Ser Glu Glu
    1280                 1285                 1290

Phe Glu  Asp Glu Glu Glu Ser  Pro Val Asn Phe Pro  Ile Tyr
    1295                 1300                 1305
```

<210> SEQ ID NO 33
<211> LENGTH: 3924

-continued

<212> TYPE: DNA
<213> ORGANISM: Homo sapiens

<400> SEQUENCE: 33
ttagtaaatg gggaaattaa caggactttc ttcttcatct tcaaactctt cagaagcagc 60
aacagggcta gttaattcaa ctcccaattg ttctgaaagt ttttttacct tctcttctaa 120
gagaatattc ttcttcactt cttccttgta attatactta agatcttcaa tttcttcaaa 180
aaatgaagga tcaaaatttt ccagttcttt tttcagcttc tttatttcct ccttcaaatg 240
ctgcttttct agatctgaca ttttgagctg tgtctctaga tcttttattt tttcctttag 300
ttgatcagca tcaggtatgg tgctttcagc tccactttgg tccttgttag cttctatctg 360
atggattaat tctgctttct ctttatccag ctgatgatta gctaatctaa gaacttgaag 420
ctcccgttta aggccttgct ctgtctcagc accttcagga acatgtttaa gaatcttaat 480
ctgttgttca aggtcttcat tgtatttgtt aactttttgt tctctctctg ttgcttcttt 540
tacaagctgt ttaaggtcag taatgctttg attttttttg gcaatatcag tttccaattc 600
ttttaacttg gtttcataca ttcttgtaac cacaatggat ttccagctct tactgtcagc 660
accttcaagc tgtggacctc tgctttctgc aaactgcaat ctcttaccag tctcttctag 720
ttgaactgtc atcttctcat ttaatatctc taaattattc tttgctatcc gtaatttctc 780
tgcagcatca gtttcttttt taagttcttt acgaagcctt tcattttcag caataatttt 840
ttctgtgcct ttggtcttgg attcatagtg catgctcaac tgatgcccaa gatgagcttt 900
aagtttttct aattcagcct tcaatttttc attttcctgc tcaatattag ccattttttc 960
actagtcaat attcctgatg ctttttttcaa ctgttcattt tctctctgga ctttttcaac 1020
tactttttttc attaaaccaa tggtttttttc cagttctggg attgtctttc cacttctacc 1080
agaccctcta acatggccaa gtttccgctg aacttctgct ttttctttct taagaaattc 1140
acacatttcc ttcaaatctc tgacttgatt ctttaatctt ggcaaatctt tatttgcttg 1200
ttcaagctga aatttcagtt caatattttc agatgacaac ttcaagtttt ccttctgaag 1260
ctcctgttct ctctgacaat gatcatctga ctctattcct gaaattgaag gcttagaata 1320
tgtatccttt gaaaactgtt tttctaaagc atgaagtttt tcttggaggt atctattttg 1380
taaatgtaaa tcttctacaa cagaatctcg aggaagagct tggtgggccc tcatatacaa 1440
tatatcattt tctaagtcaa gatttctctt ttttaattct tccaattctt tttctgactc 1500
caaagctcgt attcccaaaa cctgatcaac agtcatgcca gttgttttta gtttcctctg 1560
caaagtaagt ttctctttat cggctttggc aaaaagatcc ttcaaagtat tcaactgctt 1620
tgttaaagta aagacttccc cctctttctc ttttaacttg tttcgaattc cttctatttt 1680
ggcttgccac tttttacctt cttcccacct aattaattct tctttagcat tcttttcttt 1740
cataggtttt aggtctactt cctccacctt tccctctaat tggttctcta gtttttttaac 1800
tttcctttgg agttcttcaa ttagactttg tttattatct gtcaggggtt tgccctgtaa 1860
tccactggtt agtcttttaa tttgcctttt cagttcatca ttctcttgat caatttcctc 1920
tttctctcta agtattttat tataggcttt ttgtttcttt tgcagttcat tatttaagtc 1980
attcaaatta tcagttagtg agttttctct gtttttactt gttttaagtg cttctttcaa 2040
ttttaaaaga ttttcattta aatcttcaac ttgtgtcttt agctctctag tatgtcgatc 2100
aacgatttgt tgaacattga gatgggcctc tttttgagaa gttgcagaaa taatacgttc 2160
ttcagcagct gctgtcattt ctgcccggag ttctaaaagt gcccgactaa gtgctttctg 2220

-continued

```
ttgtttctcc ttcaaggcta attggctctt tagccgttct actagatttc tcattgtagt   2280

tgttggagct cttgaatttg cttctttttg agcctgaagt tcagatttta aacactgtga   2340

ctccttttgt gactggtcca gaagatactt taaatcctct acttccgctt ttactttttt   2400

cacttcatct tcatggtttt cttgaagctg taatttgata ttttcaaatt cttttacttt   2460

taattcagtg atttctcttt gtctctccaa atcttgtgat actttcttta gtttgaccaa   2520

gagtgaggaa agagagtcat cttgttctgc tactgtctgt tccatctcag ccagacgaat   2580

aaaatgcttg ttggtaggaa ctggagtggg agactgtttc attaaatccc aagccgtttg   2640

tttgaattta tttagtgaac tatcagcctg tagttctaat ctgtgatgaa gaatatgaag   2700

gtcttcctca tgtttcttca caatttctct ttgctcctct ctggcttttt ctagaagacg   2760

ttgatacttc tttaatactt cttctttttg atttaacctt gcttgcatgt ttgcaatggt   2820

ttgatgagca attttcaatg tgtggtgaga ttttggttcc atctcttttc tgcctagctc   2880

agctatgagc ttttctcttt ctgcagtggc aggcaatcga agcctcagtt cattgattac   2940

tttgtctctt gacagtatat tttgttctgc taaccttaaa gcagattctt tctcttttag   3000

tttctcttct agtgatttgc aagttgcccg tgtttctaga attattcgaa tgttctcctt   3060

aattttcctt agagcgatct caagttgatt tggaaggggc aaactagggt cagggattga   3120

tcctgtagct tcttcaaact tttgtgccgc atttagtatt tcattttgct gacggtcaaa   3180

aatgtctagt tggcgttcca ggtcaacttc tctttgatcc caggccattt gtctttcttc   3240

atgaaacttg ttctgttgca caatttcttc ttcaagactg ctgattgtac gttcatattc   3300

agaaattatg ttattcaaat atttatttc ttctttatcc ttgactaatt cccgatttag    3360

tttaagttct tgaagacgaa gttcttctat tttcatatgc cagttgatta cctttttgggc  3420

tcctttggta tcctttaaag tgcttattaa ctcttccagg ccctttaatt ttaattccat   3480

ctccaatgtt ttgttctcca tatttctatg ttcttgttga gaatttttca tttcttgcat   3540

tatcttaagt ttgtcatttt gtagttgaat cattgttttg gagaactttt cctgttgtgc   3600

caagggtaaa gctccactaa actgtcgtcg tagagactga attgtttggc gcagatgttt   3660

tgctctgttt cttccctcca aacgagcata atagagagcc tgttcttttt catcaagttt   3720

ctgctctaag cgcaagttgt aggcctccat cttctgcagt ttagatgtaa ttgactccaa   3780

cttaccaaga gcagtagcct cactcagttg aagagagaca ttatgttggt gcaacttggc   3840

aatgagcgac ttttcatcag actgtgcctg atagtctagc agttgcattc tgagggactc   3900

tacttccttg tccctagatt gttg                                          3924
```

<210> SEQ ID NO 34
<211> LENGTH: 3888
<212> TYPE: DNA
<213> ORGANISM: Artificial sequence
<220> FEATURE:
<223> OTHER INFORMATION: Sequence of expression cassette-CMV-mouse Myo tail-polyA

<400> SEQUENCE: 34

```
acgcgtggag ctagttatta atagtaatca attacggggt cattagttca tagcccatat     60

atggagttcc gcgttacata acttacggta aatggcccgc ctggctgacc gcccaacgac    120

ccccgcccat tgacgtcaat aatgacgtat gttcccatag taacgtcaat agggactttc    180

cattgacgtc aatgggtgga gtatttacgg taaactgccc acttggcagt acatcaagtg    240

tatcatatgc caagtacgcc ccctattgac gtcaatgacg gtaaatggcc cgcctggcat    300
```

-continued

```
tatgcccagt acatgacctt atgggacttt cctacttggc agtacatcta cgtattagtc    360
atcgctatta ccatggtgat gcggttttgg cagtacatca atgggcgtgg atagcggttt    420
gactcacggg gatttccaag tctccacccc attgacgtca atgggagttt gttttgcacc    480
aaaatcaacg ggactttcca aaatgtcgta acaactccgc cccattgacg caaatgggcg    540
gtaggcgtgt acggtgggag gtctatataa gcagagctcg tttagtgaac cgtcagatcg    600
cctggagacg ccatccacgc tgttttgacc tccatagaag acaccgggac cgatccagcc    660
tccgcggcca ccatgttggc agagcaaaat attctgtcaa gagacaaagt aatcaatgaa    720
ctgaggcttc gattgcctgc cacggctgat cgagaaaaac ttatagctga gctagaaaga    780
aaagagctgg agccgaaatc tcatcacaca atgaaaattg cccaccaaac tattgccaac    840
atgcaggcaa ggttaaatca caaggaagaa gtattgaaga aataccagca ccttctggag    900
aaggccagag aggagcaaag agaaattgtt aagaagcatg aggaagacct tcatgttctt    960
catcacaaat tagaacaaca ggccgataat tcactcaata aattcagaca gacagctcag   1020
gatttactta agcagtctcc tgctccagtt cccaccaaca aacatttcat tcgtctggcc   1080
gagatggagc agacagtagc agaacaagat gactctctgt cctcactttt gaccaaacta   1140
aagaaagtat caaaagattt ggaaaaacaa aaagaaatca ctgagttaaa agtcagagag   1200
tttgaaaata ccaaactacg gctccaagaa actcatgcca gtgaggtaaa gaaagtgaaa   1260
gcagaggtag aggacttaag gcatgctcta gcccaagcac acaaggactc ccagagttta   1320
aagtctgaac tccaggctca gaaagaagca aactccagag ctccaacaac cacaatgagg   1380
aatcttgtag acaggctaaa gagccaacta gccttgaaag agaagcaaca aaaggcactt   1440
agtcgagccc tgttggaact tcggtcggaa atgacagcag cagctgagga acgtataatc   1500
gctgtaactt ctcaaaaaga ggcaaatctc aatgttcaac aagttgttga gcgccatact   1560
agagagctaa agtcacaaat tgaagattta aatgaaaatc ttttaaaatt gaaagaagct   1620
cttaaaacaa gtaagaacaa agaaaattca ctagctgatg atttaaatga attaaataat   1680
gaactgcaaa aaaagcaaaa agcttataat aaaatcctta gagagaaaga tggaattgat   1740
caagaaaatg atgaactgag aagacagatt aaaagactgt ccagtggact gcagagcaaa   1800
actttgatag ataacaagca aagtttaatc gatgaacttc aaaagaaagt taaaaaactt   1860
gaaagccaac tggaaagaaa ggtggatgac gtagacataa agccggtgaa ggaaaagagt   1920
agtaaagaag aattaattag gtgggaagaa ggtaagaaat ggcaaaccaa agtagaggga   1980
ctacgaaaca gactaaagga gaaggaagga gaagcccacg gcctggcaaa gcagctgaat   2040
accttaaagg aactttttgc caaagctgat aaagagaaac ttactttgca gaagaaactg   2100
aaaacaacag gaatgactgt tgaccaggtt ttaggagtgc gagctttgga atctgaaaaa   2160
gagttggaag agctaaaaaa gaaaaatctg gacctagaaa atgacatatt atacatgagg   2220
acccagcagg ctcttccacg agattctgtt gtggaagact tacatttaca aaataaatac   2280
cttcaagaaa aacttcatac tttagaaaaa aaactttcaa aggagaaata ttctcagtct   2340
ttgacttcag aaatagagtc agatgatcac tgtcaaaaag aacaagaact tcagaaggaa   2400
aatttgaagt tgtcatctga aaacatcgag ctgaaatttc aacttgaaca agcaaataaa   2460
gatttgccaa gactaaagaa tcaagtgaaa gatttgaagg aaatgtgtga atttcttaag   2520
aaaggaaaac tggaacttga gcggaagctt ggtcaggtca gaggggctgg tagaagtggg   2580
aagacaatcc cagaactaga aaaaaccatt gggttaatga agaaagtagt tgaaaaagtc   2640
caaagagaaa atgaacaatt gaaaaaggca tcaggaatac tgactagtga aaaaatggct   2700
```

-continued

```
actattgagg aagaaaatag aaacttaaag gctgaactag aaaagcttaa agctcacttt   2760

ggacgtcagt tgagtatgca gtttgaatct aagaacaaag gtactgagaa aattgttgcc   2820

gaaaatgaac ggcttcggaa agaacttaag aaagaaatag aagcctctga gaaactgcgg   2880

atagctaaga acaacttaga gctggtgaac gacaagatgg cagctcaact cgaagaaact   2940

gggaagagac tacagtttgc agaaagtaga gccccacagc tggaaggtgc tgacagcaag   3000

agctggaagt caattgtggt ctcaagagtg tatgagacca agatgaaaga gcttgaaagt   3060

gacattgcca aaaagaatca aagtatcact gaccttaaac agcttgtaag agaagcaaca   3120

gagagagaac agaaagctaa gaaatacact gaagaccttg aacaacagat tgagatcctc   3180

aaaaatgttc ctgaaggtgc cgagacagag caagagctta tacgggaact ccagcttctt   3240

agattagcca ataatcagat ggataaagaa agggcagaat taatccatca gatagaaatt   3300

aacaaggacc aaaccagagc tgacagtagc atacctgatt ctgatcaact aaaggaaaag   3360

ataaatgacc tggagacaca actcagaaag ttggagctag aaaagcaaca ttcgaaggag   3420

gaagttaaaa agctgaaaaa agaactggaa aattttgatc cttcattttt tgaagaaatt   3480

gaagacctga agtataatta taaggaagaa gtgaaaaaga atatcctatt agaagagaag   3540

ctaaaaaaac tgtcggaaca gtttggattt gaactgccta gtcctcttgc tgcttctgaa   3600

cactcggaag atggagaaag tcctcatagt ttccctattt attagagatc tacatctcgc   3660

tttcttgctg tccaatttct attaaaggtt cctttgttcc ctaagtccaa ctactaaact   3720

gggggatatt atgaagggcc ttgagcatct ggattctgcc taataaaaaa catttatttt   3780

cattgcaatg atgtatttaa attatttctg aatattttac taaaaaggga atgtgggagg   3840

tcagtgcatt taaaacataa agaaagtagg taaccacgtg cggaccga                 3888
```

<210> SEQ ID NO 35
<211> LENGTH: 3891
<212> TYPE: DNA
<213> ORGANISM: Artificial sequence
<220> FEATURE:
<223> OTHER INFORMATION: Sequence of expression cassette-CMV-human Myo tail-polyA

<400> SEQUENCE: 35

```
acgcgtggag ctagttatta atagtaatca attacggggt cattagttca tagcccatat     60

atggagttcc gcgttacata acttacggta aatggcccgc ctggctgacc gcccaacgac    120

ccccgcccat tgacgtcaat aatgacgtat gttcccatag taacgtcaat agggactttc    180

cattgacgtc aatgggtgga gtatttacgg taaactgccc acttggcagt acatcaagtg    240

tatcatatgc caagtacgcc ccctattgac gtcaatgacg gtaaatggcc cgcctggcat    300

tatgcccagt acatgacctt atgggacttt cctacttggc agtacatcta cgtattagtc    360

atcgctatta ccatggtgat gcggttttgg cagtacatca atgggcgtgg atagcggttt    420

gactcacggg gatttccaag tctccacccc attgacgtca atgggagttt gttttgcacc    480

aaaatcaacg ggactttcca aaatgtcgta acaactccgc cccattgacg caaatgggcg    540

gtaggcgtgt acggtgggag gtctatataa gcagagctcg tttagtgaac cgtcagatcg    600

cctggagacg ccatccacgc tgttttgacc tccatagaag acaccgggac cgatccagcc    660

tccgcggcca ccatgttagc agaacaaaat atactgtcaa gagacaaagt aatcaatgaa    720

ctgaggcttc gattgcctgc cactgcagaa agagaaaagc tcatagctga gctaggcaga    780

aaagagatgg aaccaaaatc tcaccacaca ttgaaaattg ctcatcaaac cattgcaaac    840
```

```
atgcaagcaa ggttaaatca aaaagaagaa gtattaaaga agtatcaacg tcttctagaa    900
aaagccagag aggagcaaag agaaattgtg aagaaacatg aggaagacct tcatattctt    960
catcacagat tagaactaca ggctgatagt tcactaaata aattcaaaca aacggcttgg   1020
gatttaatga aacagtctcc cactccagtt cctaccaaca agcattttat tcgtctggct   1080
gagatggaac agacagtagc agaacaagat gactctcttt cctcactctt ggtcaaacta   1140
aagaaagtat cacaagattt ggagagacaa agagaaatca ctgaattaaa agtaaaagaa   1200
tttgaaaata tcaaattaca gcttcaagaa aaccatgaag atgaagtgaa aaaagtaaaa   1260
gcggaagtag aggatttaaa gtatcttctg gaccagtcac aaaaggagtc acagtgttta   1320
aaatctgaac ttcaggctca aaaagaagca aattcaagag ctccaacaac tacaatgaga   1380
aatctagtag aacggctaaa gagccaatta gccttgaagg agaaacaaca gaaagcactt   1440
agtcgggcac ttttagaact ccgggcagaa atgacagcag ctgctgaaga acgtattatt   1500
tctgcaactt ctcaaaaaga ggcccatctc aatgttcaac aaatcgttga tcgacatact   1560
agagagctaa agacacaagt tgaagattta aatgaaaatc ttttaaaatt gaaagaagca   1620
cttaaaacaa gtaaaaacag agaaaactca ctaactgata atttgaatga cttaaataat   1680
gaactgcaaa agaaacaaaa agcctataat aaaatactta gagagaaaga ggaaattgat   1740
caagagaatg atgaactgaa aaggcaaatt aaaagactaa ccagtggatt acagggcaaa   1800
cccctgacag ataataaaca aagtctaatt gaagaactcc aaaggaaagt taaaaaacta   1860
gagaaccaat tagagggaaa ggtggaggaa gtagacctaa aacctatgaa agaaaagaat   1920
gctaaagaag aattaattag gtgggaagaa ggtaaaaagt ggcaagccaa aatagaagga   1980
attcgaaaca agttaaaaga gaaagagggg gaagtcttta ctttaacaaa gcagttgaat   2040
actttgaagg atctttttgc caaagccgat aaagagaaac ttactttgca gaggaaacta   2100
aaaacaactg gcatgactgt tgatcaggtt ttgggaatac gagctttgga gtcagaaaaa   2160
gaattggaag aattaaaaaa gagaaatctt gacttagaaa atgatatatt gtatatgagg   2220
gcccaccaag ctcttcctcg agattctgtt gtagaagatt tacatttaca aaatagatac   2280
ctccaagaaa aacttcatgc tttagaaaaa cagttttcaa aggatacata ttctaagcct   2340
tcaatttcag gaatagagtc agatgatcat tgtcagagag aacaggagct tcagaaggaa   2400
aacttgaagt tgtcatctga aaatattgaa ctgaaatttc agcttgaaca agcaaataaa   2460
gatttgccaa gattaaagaa tcaagtcaga gatttgaagg aaatgtgtga atttcttaag   2520
aaagaaaaag cagaagttca gcggaaactt ggccatgtta gagggtctgg tagaagtgga   2580
aagacaatcc cagaactgga aaaaaccatt ggtttaatga aaaaagtagt tgaaaaagtc   2640
cagagagaaa atgaacagtt gaaaaaagca tcaggaatat tgactagtga aaaaatggct   2700
aatattgagc aggaaaatga aaaattgaag gctgaattag aaaaacttaa agctcatctt   2760
gggcatcagt tgagcatgca ctatgaatcc aagaccaaag gcacagaaaa aattattgct   2820
gaaaatgaaa ggcttcgtaa agaacttaaa aaagaaactg atgctgcaga gaaattacgg   2880
atagcaaaga ataatttaga gatattaaat gagaagatga cagttcaact agaagagact   2940
ggtaagagat tgcagtttgc agaaagcaga ggtccacagc ttgaaggtgc tgacagtaag   3000
agctggaaat ccattgtggt tacaagaatg tatgaaacca agttaaaaga attggaaact   3060
gatattgcca aaaaaaatca aagcattact gaccttaaac agcttgtaaa agaagcaaca   3120
gagagagaac aaaaagttaa caaatacaat gaagaccttg aacaacagat taagattctt   3180
```

-continued

```
aaacatgttc ctgaaggtgc tgagacagag caaggcctta aacgggagct tcaagttctt   3240

agattagcta atcatcagct ggataaagag aaagcagaat taatccatca gatagaagct   3300

aacaaggacc aaagtggagc tgaaagcacc atacctgatg ctgatcaact aaaggaaaaa   3360

ataaaagatc tagagacaca gctcaaaatg tcagatctag aaaagcagca tttgaaggag   3420

gaaataaaga agctgaaaaa agaactggaa aattttgatc cttcattttt tgaagaaatt   3480

gaagatctta agtataatta caaggaagaa gtgaagaaga atattctctt agaagagaag   3540

gtaaaaaaac tttcagaaca attgggagtt gaattaacta gccctgttgc tgcttctgaa   3600

gagtttgaag atgaagaaga aagtcctgtt aatttcccca tttactaaag atctacatct   3660

cgctttcttg ctgtccaatt tctattaaag gttcctttgt tccctaagtc caactactaa   3720

actgggggat attatgaagg gccttgagca tctggattct gcctaataaa aaacatttat   3780

tttcattgca atgatgtatt taaattattt ctgaatattt tactaaaaag ggaatgtggg   3840

aggtcagtgc atttaaaaca taaagaaagt aggtaaccac gtgcggaccg a            3891
```

<210> SEQ ID NO 36
<211> LENGTH: 1818
<212> TYPE: DNA
<213> ORGANISM: Artificial sequence
<220> FEATURE:
<223> OTHER INFORMATION: Sequence of expression cassette-CMV-mouse DSD-polyA

<400> SEQUENCE: 36

```
acgcgtggag ctagttatta atagtaatca attacggggt cattagttca tagcccatat     60

atggagttcc gcgttacata acttacggta aatggcccgc ctggctgacc gcccaacgac    120

ccccgcccat tgacgtcaat aatgacgtat gttcccatag taacgtcaat agggactttc    180

cattgacgtc aatgggtgga gtatttacgg taaactgccc acttggcagt acatcaagtg    240

tatcatatgc caagtacgcc ccctattgac gtcaatgacg gtaaatggcc cgcctggcat    300

tatgcccagt acatgacctt atgggacttt cctacttggc agtacatcta cgtattagtc    360

atcgctatta ccatggtgat gcggttttgg cagtacatca atgggcgtgg atagcggttt    420

gactcacggg gatttccaag tctccacccc attgacgtca atgggagttt gttttgcacc    480

aaaatcaacg ggactttcca aaatgtcgta acaactccgc cccattgacg caaatgggcg    540

gtaggcgtgt acggtgggag gtctatataa gcagagctcg tttagtgaac cgtcagatcg    600

cctggagacg ccatccacgc tgttttgacc tccatagaag acaccgggac cgatccagcc    660

tccgcggcca ccatggattt acttaagcag tctcctgctc cagttcccac caacaaacat    720

ttcattcgtc tggccgagat ggagcagaca gtagcagaac aagatgactc tctgtcctca    780

cttttgacca aactaaagaa agtatcaaaa gatttggaaa aacaaaaaga aatcactgag    840

ttaaaagtca gagagtttga aaataccaaa ctacggctcc aagaaactca tgccagtgag    900

gtaaagaaag tgaaagcaga ggtagaggac ttaaggcatg ctctagccca agcacacaag    960

gactcccaga gtttaaagtc tgaactccag gctcagaaag aagcaaactc cagagctcca   1020

acaaccacaa tgaggaatct tgtagacagg ctaaagagcc aactagcctt gaaagagaag   1080

caacaaaagg cacttagtcg agccctgttg gaacttcggt cggaaatgac agcagcagct   1140

gaggaacgta taatcgctgt aacttctcaa aaagaggcaa atctcaatgt tcaacaagtt   1200

gttgagcgcc atactagaga gctaaagtca caaattgaag atttaaatga aaatctttta   1260

aaattgaaag aagctcttaa aacaagtaag aacaaagaaa attcactagc tgatgattta   1320
```

```
aatgaattaa ataatgaact gcaaaaaaag caaaaagctt ataataaaat ccttagagag   1380

aaagatggaa ttgatcaaga aaatgatgaa ctgagaagac agattaaaag actgtccagt   1440

ggactgcaga gcaaaacttt gatagataac aagcaaagtt taatcgatga acttcaaaag   1500

aaagttaaaa aacttgaaag ccaactggaa agaaaggtgg atgacgtaga cataaagccg   1560

gtgaaggaaa agtagagatc tacatctcgc tttcttgctg tccaatttct attaaaggtt   1620

cctttgttcc ctaagtccaa ctactaaact gggggatatt atgaagggcc ttgagcatct   1680

ggattctgcc taataaaaaa catttatttt cattgcaatg atgtatttaa attatttctg   1740

aatattttac taaaaaggga atgtgggagg tcagtgcatt taaaacataa agaaagtagg   1800

taaccacgtg cggaccga                                                 1818
```

<210> SEQ ID NO 37
<211> LENGTH: 1818
<212> TYPE: DNA
<213> ORGANISM: Artificial sequence
<220> FEATURE:
<223> OTHER INFORMATION: Sequence of expression cassette-CMV-human DSD-polyA

<400> SEQUENCE: 37

```
acgcgtggag ctagttatta atagtaatca attacggggt cattagttca tagcccatat     60

atggagttcc gcgttacata acttacggta aatggcccgc ctggctgacc gcccaacgac    120

ccccgcccat tgacgtcaat aatgacgtat gttcccatag taacgtcaat agggactttc    180

cattgacgtc aatgggtgga gtatttacgg taaactgccc acttggcagt acatcaagtg    240

tatcatatgc caagtacgcc ccctattgac gtcaatgacg gtaaatggcc cgcctggcat    300

tatgcccagt acatgacctt atgggacttt cctacttggc agtacatcta cgtattagtc    360

atcgctatta ccatggtgat gcggttttgg cagtacatca atgggcgtgg atagcggttt    420

gactcacggg gatttccaag tctccacccc attgacgtca atgggagttt gttttgcacc    480

aaaatcaacg ggactttcca aaatgtcgta acaactccgc cccattgacg caaatgggcg    540

gtaggcgtgt acggtgggag gtctatataa gcagagctcg tttagtgaac cgtcagatcg    600

cctggagacg ccatccacgc tgttttgacc tccatagaag acaccgggac cgatccagcc    660

tccgcggcca ccatggattt aatgaaacag tctcccactc cagttcctac caacaagcat    720

tttattcgtc tggctgagat ggaacagaca gtagcagaac aagatgactc tctttcctca    780

ctcttggtca aactaaagaa agtatcacaa gatttggaga gacaaagaga aatcactgaa    840

ttaaaagtaa aagaatttga aaatatcaaa ttacagcttc aagaaaacca tgaagatgaa    900

gtgaaaaaag taaaagcgga agtagaggat ttaaagtatc ttctggacca gtcacaaaag    960

gagtcacagt gtttaaaatc tgaacttcag gctcaaaaag aagcaaattc aagagctcca   1020

acaactacaa tgagaaatct agtagaacgg ctaaagagcc aattagcctt gaaggagaaa   1080

caacagaaag cacttagtcg ggcactttta gaactccggg cagaaatgac agcagctgct   1140

gaagaacgta ttatttctgc aacttctcaa aaagaggccc atctcaatgt tcaacaaatc   1200

gttgatcgac atactagaga gctaaagaca caagttgaag atttaaatga aaatctttta   1260

aaattgaaag aagcacttaa aacaagtaaa aacagagaaa actcactaac tgataatttg   1320

aatgacttaa ataatgaact gcaaaagaaa caaaaagcct ataataaaat acttagagag   1380

aaagaggaaa ttgatcaaga gaatgatgaa ctgaaaaggc aaattaaaag actaaccagt   1440

ggattacagg gcaaacccct gacagataat aaacaaagtc taattgaaga actccaaagg   1500
```

aaagttaaaa aactagagaa ccaattagag ggaaaggtgg aggaagtaga cctaaaacct 1560
atgaaagaaa agtagagatc tacatctcgc tttcttgctg tccaatttct attaaaggtt 1620
cctttgttcc ctaagtccaa ctactaaact gggggatatt atgaagggcc ttgagcatct 1680
ggattctgcc taataaaaaa catttatttt cattgcaatg atgtatttaa attatttctg 1740
aatattttac taaaaaggga atgtgggagg tcagtgcatt taaaacataa agaaagtagg 1800
taaccacgtg cggaccga 1818

<210> SEQ ID NO 38
<211> LENGTH: 4842
<212> TYPE: DNA
<213> ORGANISM: Artificial sequence
<220> FEATURE:
<223> OTHER INFORMATION: Sequence of expression cassette-CMV-mouse C-terminal-polyA

<400> SEQUENCE: 38
acgcgtggag ctagttatta atagtaatca attacggggt cattagttca tagcccatat 60
atggagttcc gcgttacata acttacggta aatggcccgc ctggctgacc gcccaacgac 120
ccccgcccat tgacgtcaat aatgacgtat gttcccatag taacgtcaat agggactttc 180
cattgacgtc aatgggtgga gtatttacgg taaactgccc acttggcagt acatcaagtg 240
tatcatatgc caagtacgcc ccctattgac gtcaatgacg gtaaatggcc cgcctggcat 300
tatgcccagt acatgacctt atgggacttt cctacttggc agtacatcta cgtattagtc 360
atcgctatta ccatggtgat gcggttttgg cagtacatca atgggcgtgg atagcggttt 420
gactcacggg gatttccaag tctccacccc attgacgtca atgggagttt gttttgcacc 480
aaaatcaacg ggactttcca aaatgtcgta acaactccgc cccattgacg caaatgggcg 540
gtaggcgtgt acggtgggag gtctatataa gcagagctcg tttagtgaac cgtcagatcg 600
cctggagacg ccatccacgc tgttttgacc tccatagaag acaccgggac cgatccagcc 660
tccgcggcca ccatgcaaca acagtccagg gaaaaggaag tggaatccct cagaacgcag 720
ctgctggact tccaggcaca atctgacgaa aaggctctaa ttgccaaatt gcaccaacat 780
gttgtctctc ttcaaattag tgaggccact gccctcggta agttagagtc agttacgtcc 840
aaactccaga agatggaagc ctacaatttg cgcttagaac agaaactgga tgaaaaagag 900
caggcgctct actatgctcg tttggaaggt agaaacagag caaaacacct gcgccaaacc 960
attcagtcgc ttcgaagaca gttcagtgga gctctaccct tagcacagca ggaaaagttc 1020
tccaaaacga tgattcagtt gcaaaatgac aaacttaaga taatgcaaga aatgaagaat 1080
tcgcaacagg aacacagaaa tatggaaaac aaaacactgg agttggaatt aaaattaaaa 1140
ggcttagaag aattgatcag tactttaaag gatgccaggg gagcccagaa ggtaatcaat 1200
tggcatgtga aaatagaaga acttcgcctc caagaactta agctaaatag agaactagtc 1260
aagggtaaag aagaaatcaa atatttgaat aatatcatct ctgaatatga gcatacaatc 1320
aacagtctag aggaagaaat tgttcagcaa agcaagttcc atgaagaaag acagatggct 1380
tgggatcaaa gagaagttga gctggaacgc cagttagaca tttttgatca tcagcaaaat 1440
gaaatactca gtgcagcaca aaagtttgaa gactctacag gatcaatgcc agaccccagc 1500
ttgcctcttc caaaccaact tgaaattgct ctaagaaaaa ttaaggagaa tattcaagta 1560
attcttaaaa cacaagcaac ttgcaagtca ctagaagaga aactaaaaga aaaagaatct 1620
gctttacggt tggcagagca aaatattctg tcaagagaca aagtaatcaa tgaactgagg 1680

-continued

```
cttcgattgc ctgccacggc tgatcgagaa aaacttatag ctgagctaga aagaaaagag   1740
ctggagccga aatctcatca cacaatgaaa attgcccacc aaactattgc caacatgcag   1800
gcaaggttaa atcacaagga agaagtattg aagaaatacc agcaccttct ggagaaggcc   1860
agagaggagc aaagagaaat tgttaagaag catgaggaag accttcatgt tcttcatcac   1920
aaattagaac aacaggccga taattcactc aataaattca gacagacagc tcaggattta   1980
cttaagcagt ctcctgctcc agttcccacc aacaaacatt tcattcgtct ggccgagatg   2040
gagcagacag tagcagaaca agatgactct ctgtcctcac ttttgaccaa actaaagaaa   2100
gtatcaaaag atttggaaaa acaaaaagaa atcactgagt taaaagtcag agagtttgaa   2160
aataccaaac tacggctcca agaaactcat gccagtgagg taaagaaagt gaaagcagag   2220
gtagaggact taaggcatgc tctagcccaa gcacacaagg actcccagag tttaaagtct   2280
gaactccagg ctcagaaaga agcaaactcc agagctccaa caaccacaat gaggaatctt   2340
gtagacaggc taaagagcca actagccttg aaagagaagc aacaaaaggc acttagtcga   2400
gccctgttgg aacttcggtc ggaaatgaca gcagcagctg aggaacgtat aatcgctgta   2460
acttctcaaa aagaggcaaa tctcaatgtt caacaagttg ttgagcgcca tactagagag   2520
ctaaagtcac aaattgaaga tttaaatgaa aatcttttaa aattgaaaga agctcttaaa   2580
acaagtaaga acaaagaaaa ttcactagct gatgatttaa atgaattaaa taatgaactg   2640
caaaaaaagc aaaaagctta taataaaatc cttagagaga aagatggaat tgatcaagaa   2700
aatgatgaac tgagaagaca gattaaaaga ctgtccagtg gactgcagag caaaactttg   2760
atagataaca agcaaagttt aatcgatgaa cttcaaaaga aagttaaaaa acttgaaagc   2820
caactggaaa gaaaggtgga tgacgtagac ataaagccgg tgaaggaaaa gagtagtaaa   2880
gaagaattaa ttaggtggga agaaggtaag aaatggcaaa ccaaagtaga gggactacga   2940
aacagactaa aggagaagga aggagaagcc cacggcctgg caaagcagct gaatacctta   3000
aaggaacttt ttgccaaagc tgataaagag aaacttactt tgcagaagaa actgaaaaca   3060
acaggaatga ctgttgacca ggttttagga gtgcgagctt tggaatctga aaaagagttg   3120
gaagagctaa aaaagaaaaa tctggaccta gaaaatgaca tattatacat gaggacccag   3180
caggctcttc cacgagattc tgttgtggaa gacttacatt tacaaaataa ataccttcaa   3240
gaaaaacttc atactttaga aaaaaaactt tcaaaggaga aatattctca gtctttgact   3300
tcagaaatag agtcagatga tcactgtcaa aaagaacaag aacttcagaa ggaaaatttg   3360
aagttgtcat ctgaaaacat cgagctgaaa tttcaacttg aacaagcaaa taaagatttg   3420
ccaagactaa agaatcaagt gaaagatttg aaggaaatgt gtgaatttct taagaaagga   3480
aaactggaac ttgagcggaa gcttggtcag gtcagagggg ctggtagaag tgggaagaca   3540
atcccagaac tagaaaaaac cattgggtta atgaagaaag tagttgaaaa agtccaaaga   3600
gaaaatgaac aattgaaaaa ggcatcagga atactgacta gtgaaaaaat ggctactatt   3660
gaggaagaaa atagaaactt aaaggctgaa ctagaaaagc ttaaagctca ctttggacgt   3720
cagttgagta tgcagtttga atctaagaac aaaggtactg agaaaattgt tgccgaaaat   3780
gaacggcttc ggaaagaact taagaaagaa atagaagcct ctgagaaact gcggatagct   3840
aagaacaact tagagctggt gaacgacaag atggcagctc aactcgaaga aactgggaag   3900
agactacagt ttgcagaaag tagagcccca cagctggaag gtgctgacag caagagctgg   3960
aagtcaattg tggtctcaag agtgtatgag accaagatga aagagcttga aagtgacatt   4020
gccaaaaaga atcaaagtat cactgacctt aaacagcttg taagagaagc aacagagaga   4080
```

```
gaacagaaag ctaagaaata cactgaagac cttgaacaac agattgagat cctcaaaaat   4140

gttcctgaag gtgccgagac agagcaagag cttatacggg aactccagct tcttagatta   4200

gccaataatc agatggataa agaaagggca gaattaatcc atcagataga aattaacaag   4260

gaccaaacca gagctgacag tagcatacct gattctgatc aactaaagga aaagataaat   4320

gacctggaga cacaactcag aaagttggag ctagaaaagc aacattcgaa ggaggaagtt   4380

aaaaagctga aaaaagaact ggaaaatttt gatccttcat tttttgaaga aattgaagac   4440

ctgaagtata attataagga agaagtgaaa aagaatatcc tattagaaga gaagctaaaa   4500

aaactgtcgg aacagtttgg atttgaactg cctagtcctc ttgctgcttc tgaacactcg   4560

gaagatggag aaagtcctca tagtttccct atttattaga gatctacatc tcgctttctt   4620

gctgtccaat ttctattaaa ggttcctttg ttccctaagt ccaactacta aactggggga   4680

tattatgaag ggccttgagc atctggattc tgcctaataa aaaacattta ttttcattgc   4740

aatgatgtat ttaaattatt tctgaatatt ttactaaaaa gggaatgtgg gaggtcagtg   4800

catttaaaac ataaagaaag taggtaacca cgtgcggacc ga                       4842
```

<210> SEQ ID NO 39
<211> LENGTH: 4842
<212> TYPE: DNA
<213> ORGANISM: Artificial sequence
<220> FEATURE:
<223> OTHER INFORMATION: Sequence of expression cassette-CMV-human C-terminal-polyA

<400> SEQUENCE: 39

```
acgcgtggag ctagttatta atagtaatca attacggggt cattagttca tagcccatat     60

atggagttcc gcgttacata acttacggta aatggcccgc ctggctgacc gcccaacgac    120

ccccgcccat tgacgtcaat aatgacgtat gttcccatag taacgtcaat agggactttc    180

cattgacgtc aatgggtgga gtatttacgg taaactgccc acttggcagt acatcaagtg    240

tatcatatgc caagtacgcc ccctattgac gtcaatgacg gtaaatggcc cgcctggcat    300

tatgcccagt acatgacctt atgggacttt cctacttggc agtacatcta cgtattagtc    360

atcgctatta ccatggtgat gcggttttgg cagtacatca atgggcgtgg atagcggttt    420

gactcacggg gatttccaag tctccacccc attgacgtca atgggagttt gttttgcacc    480

aaaatcaacg ggactttcca aaatgtcgta acaactccgc cccattgacg caaatgggcg    540

gtaggcgtgt acggtgggag gtctatataa gcagagctcg tttagtgaac cgtcagatcg    600

cctggagacg ccatccacgc tgttttgacc tccatagaag acaccgggac cgatccagcc    660

tccgcggcca ccatgcaaca atctagggac aaggaagtag agtccctcag aatgcaactg    720

ctagactatc aggcacagtc tgatgaaaag tcgctcattg ccaagttgca ccaacataat    780

gtctctcttc aactgagtga ggctactgct cttggtaagt tggagtcaat tacatctaaa    840

ctgcagaaga tggaggccta caacttgcgc ttagagcaga aacttgatga aaaagaacag    900

gctctctatt atgctcgttt ggagggaaga aacagagcaa aacatctgcg ccaaacaatt    960

cagtctctac gacgacagtt tagtggagct ttacccttgg cacaacagga aaagttctcc   1020

aaaacaatga ttcaactaca aaatgacaaa cttaagataa tgcaagaaat gaaaaattct   1080

caacaagaac atagaaatat ggagaacaaa acattggaga tggaattaaa attaaagggc   1140

ctggaagagt taataagcac tttaaaggat accaaaggag cccaaaaggt aatcaactgg   1200

catatgaaaa tagaagaact tcgtcttcaa gaacttaaac taaatcggga attagtcaag   1260
```

-continued

```
gataaagaag aaataaaata tttgaataac ataatttctg aatatgaacg tacaatcagc   1320
agtcttgaag aagaaattgt gcaacagaac aagtttcatg aagaaagaca aatggcctgg   1380
gatcaaagag aagttgacct ggaacgccaa ctagacattt ttgaccgtca gcaaaatgaa   1440
atactaaatg cggcacaaaa gtttgaagaa gctacaggat caatccctga ccctagtttg   1500
ccccttccaa atcaacttga gatcgctcta aggaaaatta aggagaacat tcgaataatt   1560
ctagaaacac gggcaacttg caaatcacta gaagagaaac taaaagagaa agaatctgct   1620
ttaaggttag cagaacaaaa tatactgtca agagacaaag taatcaatga actgaggctt   1680
cgattgcctg ccactgcaga aagagaaaag ctcatagctg agctaggcag aaaagagatg   1740
gaaccaaaat ctcaccacac attgaaaatt gctcatcaaa ccattgcaaa catgcaagca   1800
aggttaaatc aaaaagaaga agtattaaag aagtatcaac gtcttctaga aaaagccaga   1860
gaggagcaaa gagaaattgt gaagaaacat gaggaagacc ttcatattct tcatcacaga   1920
ttagaactac aggctgatag ttcactaaat aaattcaaac aaacggcttg ggatttaatg   1980
aaacagtctc ccactccagt tcctaccaac aagcatttta ttcgtctggc tgagatggaa   2040
cagacagtag cagaacaaga tgactctctt tcctcactct tggtcaaact aaagaaagta   2100
tcacaagatt tggagagaca aagagaaatc actgaattaa aagtaaaaga atttgaaaat   2160
atcaaattac agcttcaaga aaaccatgaa gatgaagtga aaaaagtaaa agcggaagta   2220
gaggatttaa agtatcttct ggaccagtca caaaaggagt cacagtgttt aaaatctgaa   2280
cttcaggctc aaaaagaagc aaattcaaga gctccaacaa ctacaatgag aaatctagta   2340
gaacggctaa agagccaatt agccttgaag gagaaacaac agaaagcact tagtcgggca   2400
cttttagaac tccgggcaga aatgacagca gctgctgaag aacgtattat ttctgcaact   2460
tctcaaaaag aggcccatct caatgttcaa caaatcgttg atcgacatac tagagagcta   2520
aagacacaag ttgaagattt aaatgaaaat cttttaaaat tgaaagaagc acttaaaaca   2580
agtaaaaaca gagaaaactc actaactgat aatttgaatg acttaaataa tgaactgcaa   2640
aagaaacaaa aagcctataa taaaatactt agagagaaag aggaaattga tcaagagaat   2700
gatgaactga aaaggcaaat taaaagacta accagtggat tacagggcaa acccctgaca   2760
gataataaac aaagtctaat tgaagaactc caaaggaaag ttaaaaaact agagaaccaa   2820
ttagagggaa aggtggagga agtagaccta aaacctatga aagaaaagaa tgctaaagaa   2880
gaattaatta ggtgggaaga aggtaaaaag tggcaagcca aaatagaagg aattcgaaac   2940
aagttaaaag agaaagaggg ggaagtcttt actttaacaa agcagttgaa tactttgaag   3000
gatcttttg ccaaagccga taaagagaaa cttactttgc agaggaaact aaaaacaact   3060
ggcatgactg ttgatcaggt tttgggaata cgagctttgg agtcagaaaa agaattggaa   3120
gaattaaaaa agagaaatct tgacttagaa aatgatatat tgtatatgag ggcccaccaa   3180
gctcttcctc gagattctgt tgtagaagat ttacatttac aaaatagata cctccaagaa   3240
aaacttcatg ctttagaaaa acagttttca aaggatacat attctaagcc ttcaatttca   3300
ggaatagagt cagatgatca ttgtcagaga gaacaggagc ttcagaagga aaacttgaag   3360
ttgtcatctg aaaatattga actgaaattt cagcttgaac aagcaaataa agatttgcca   3420
agattaaaga atcaagtcag agatttgaag gaaatgtgtg aatttcttaa gaaagaaaaa   3480
gcagaagttc agcggaaact tggccatgtt agagggtctg gtagaagtgg aaagacaatc   3540
ccagaactgg aaaaaaccat tggtttaatg aaaaaagtag ttgaaaaagt ccagagagaa   3600
```

-continued aatgaacagt tgaaaaaagc atcaggaata ttgactagtg aaaaaatggc taatattgag 3660
caggaaaatg aaaaattgaa ggctgaatta gaaaaactta aagctcatct tgggcatcag 3720
ttgagcatgc actatgaatc caagaccaaa ggcacagaaa aaattattgc tgaaaatgaa 3780
aggcttcgta aagaacttaa aaaagaaact gatgctgcag agaaattacg gatagcaaag 3840
aataatttag agatattaaa tgagaagatg acagttcaac tagaagagac tggtaagaga 3900
ttgcagtttg cagaaagcag aggtccacag cttgaaggtg ctgacagtaa gagctggaaa 3960
tccattgtgg ttacaagaat gtatgaaacc aagttaaaag aattggaaac tgatattgcc 4020
aaaaaaaatc aaagcattac tgaccttaaa cagcttgtaa aagaagcaac agagagagaa 4080
caaaaagtta acaaatacaa tgaagacctt gaacaacaga ttaagattct taaacatgtt 4140
cctgaaggtg ctgagacaga gcaaggcctt aaacgggagc ttcaagttct tagattagct 4200
aatcatcagc tggataaaga gaaagcagaa ttaatccatc agatagaagc taacaaggac 4260
caaagtggag ctgaaagcac catacctgat gctgatcaac taaaggaaaa aataaaagat 4320
ctagagacac agctcaaaat gtcagatcta gaaaagcagc atttgaagga ggaaataaag 4380
aagctgaaaa aagaactgga aaattttgat ccttcatttt ttgaagaaat tgaagatctt 4440
aagtataatt acaaggaaga agtgaagaag aatattctct tagaagagaa ggtaaaaaaa 4500
ctttcagaac aattgggagt tgaattaact agccctgttg ctgcttctga agagtttgaa 4560
gatgaagaag aaagtcctgt taatttcccc atttactaaa gatctacatc tcgctttctt 4620
gctgtccaat ttctattaaa ggttcctttg ttccctaagt ccaactacta aactggggga 4680
tattatgaag ggccttgagc atctggattc tgcctaataa aaaacattta ttttcattgc 4740
aatgatgtat ttaaattatt tctgaatatt ttactaaaaa gggaatgtgg gaggtcagtg 4800
catttaaaac ataaagaaag taggtaacca cgtgcggacc ga 4842

<210> SEQ ID NO 40
<211> LENGTH: 4178
<212> TYPE: DNA
<213> ORGANISM: Artificial sequence
<220> FEATURE:
<223> OTHER INFORMATION: Sequence of mouse Myo tail expression vector

<400> SEQUENCE: 40
ggcagctgcg cgctcgctcg ctcactgagg ccgcccgggc aaagcccggg cgtcgggcga 60
cctttggtcg cccggcctca gtgagcgagc gagcgcgcag agagggagtg gccaactcca 120
tcactagggg ttcctgcggc cgcacgcgtg gagctagtta ttaatagtaa tcaattacgg 180
ggtcattagt tcatagccca tatatggagt tccgcgttac ataacttacg gtaaatggcc 240
cgcctggctg accgcccaac gacccccgcc cattgacgtc aataatgacg tatgttccca 300
tagtaacgtc aatagggact ttccattgac gtcaatgggt ggagtattta cggtaaactg 360
cccacttggc agtacatcaa gtgtatcata tgccaagtac gccccctatt gacgtcaatg 420
acggtaaatg gcccgcctgg cattatgccc agtacatgac cttatgggac tttcctactt 480
ggcagtacat ctacgtatta gtcatcgcta ttaccatggt gatgcggttt tggcagtaca 540
tcaatgggcg tggatagcgg tttgactcac ggggatttcc aagtctccac cccattgacg 600
tcaatgggag tttgttttgc accaaaatca acgggacttt ccaaaatgtc gtaacaactc 660
cgccccattg acgcaaatgg gcggtaggcg tgtacggtgg gaggtctata taagcagagc 720
tcgtttagtg aaccgtcaga tcgcctggag acgccatcca cgctgttttg acctccatag 780
aagacaccgg gaccgatcca gcctccgcgg ccaccatgtt ggcagagcaa aatattctgt 840

```
caagagacaa agtaatcaat gaactgaggc ttcgattgcc tgccacggct gatcgagaaa    900
aacttatagc tgagctagaa agaaaagagc tggagccgaa atctcatcac acaatgaaaa    960
ttgcccacca aactattgcc aacatgcagg caaggttaaa tcacaaggaa gaagtattga   1020
agaaatacca gcaccttctg gagaaggcca gagaggagca aagagaaatt gttaagaagc   1080
atgaggaaga ccttcatgtt cttcatcaca aattagaaca acaggccgat aattcactca   1140
ataaattcag acagacagct caggatttac ttaagcagtc tcctgctcca gttcccacca   1200
acaaacattt cattcgtctg gccgagatgg agcagacagt agcagaacaa gatgactctc   1260
tgtcctcact tttgaccaaa ctaaagaaag tatcaaaaga tttggaaaaa caaaaagaaa   1320
tcactgagtt aaaagtcaga gagtttgaaa ataccaaact acggctccaa gaaactcatg   1380
ccagtgaggt aaagaaagtg aaagcagagg tagaggactt aaggcatgct ctagcccaag   1440
cacacaagga ctcccagagt ttaaagtctg aactccaggc tcagaaagaa gcaaactcca   1500
gagctccaac aaccacaatg aggaatcttg tagacaggct aaagagccaa ctagccttga   1560
aagagaagca acaaaaggca cttagtcgag ccctgttgga acttcggtcg gaaatgacag   1620
cagcagctga ggaacgtata atcgctgtaa cttctcaaaa agaggcaaat ctcaatgttc   1680
aacaagttgt tgagcgccat actagagagc taaagtcaca aattgaagat ttaaatgaaa   1740
atcttttaaa attgaaagaa gctcttaaaa caagtaagaa caaagaaaat tcactagctg   1800
atgatttaaa tgaattaaat aatgaactgc aaaaaaagca aaaagcttat aataaaatcc   1860
ttagagagaa agatggaatt gatcaagaaa atgatgaact gagaagacag attaaaagac   1920
tgtccagtgg actgcagagc aaaactttga tagataacaa gcaaagttta atcgatgaac   1980
ttcaaaagaa agttaaaaaa cttgaaagcc aactggaaag aaaggtggat gacgtagaca   2040
taaagccggt gaaggaaaag agtagtaaag aagaattaat taggtgggaa gaaggtaaga   2100
aatggcaaac caaagtagag ggactacgaa acagactaaa ggagaaggaa ggagaagccc   2160
acggcctggc aaagcagctg aataccttaa aggaactttt tgccaaagct gataaagaga   2220
aacttacttt gcagaagaaa ctgaaaacaa caggaatgac tgttgaccag gttttaggag   2280
tgcgagcttt ggaatctgaa aaagagttgg aagagctaaa aaagaaaaat ctggacctag   2340
aaaatgacat attatacatg aggacccagc aggctcttcc acgagattct gttgtggaag   2400
acttacattt acaaaataaa taccttcaag aaaaacttca tactttagaa aaaaaacttt   2460
caaaggagaa atattctcag tctttgactt cagaaataga gtcagatgat cactgtcaaa   2520
aagaacaaga acttcagaag gaaaatttga agttgtcatc tgaaaacatc gagctgaaat   2580
ttcaacttga acaagcaaat aaagatttgc caagactaaa gaatcaagtg aaagatttga   2640
aggaaatgtg tgaatttctt aagaaaggaa aactggaact tgagcggaag cttggtcagg   2700
tcagaggggc tggtagaagt gggaagacaa tcccagaact agaaaaaacc attgggttaa   2760
tgaagaaagt agttgaaaaa gtccaaagag aaaatgaaca attgaaaaag gcatcaggaa   2820
tactgactag tgaaaaaatg gctactattg aggaagaaaa tagaaactta aaggctgaac   2880
tagaaaagct taaagctcac tttggacgtc agttgagtat gcagtttgaa tctaagaaca   2940
aaggtactga gaaaattgtt gccgaaaatg aacggcttcg gaaagaactt aagaaagaaa   3000
tagaagcctc tgagaaactg cggatagcta agaacaactt agagctggtg aacgacaaga   3060
tggcagctca actcgaagaa actgggaaga gactacagtt tgcagaaagt agagccccac   3120
agctggaagg tgctgacagc aagagctgga agtcaattgt ggtctcaaga gtgtatgaga   3180
```

```
ccaagatgaa agagcttgaa agtgacattg ccaaaaagaa tcaaagtatc actgacctta   3240

aacagcttgt aagagaagca acagagagag aacagaaagc taagaaatac actgaagacc   3300

ttgaacaaca gattgagatc ctcaaaaatg ttcctgaagg tgccgagaca gagcaagagc   3360

ttatacggga actccagctt cttagattag ccaataatca gatggataaa gaaagggcag   3420

aattaatcca tcagatagaa attaacaagg accaaaccag agctgacagt agcatacctg   3480

attctgatca actaaaggaa aagataaatg acctggagac acaactcaga aagttggagc   3540

tagaaaagca acattcgaag gaggaagtta aaaagctgaa aaaagaactg gaaaattttg   3600

atccttcatt ttttgaagaa attgaagacc tgaagtataa ttataaggaa gaagtgaaaa   3660

agaatatcct attagaagag aagctaaaaa aactgtcgga acagtttgga tttgaactgc   3720

ctagtcctct tgctgcttct gaacactcgg aagatggaga aagtcctcat agtttcccta   3780

tttattagag atctacatct cgctttcttg ctgtccaatt tctattaaag gttcctttgt   3840

tccctaagtc caactactaa actgggggat attatgaagg gccttgagca tctggattct   3900

gcctaataaa aaacatttat tttcattgca atgatgtatt taaattattt ctgaatattt   3960

tactaaaaag ggaatgtggg aggtcagtgc atttaaaaca taaagaaagt aggtaaccac   4020

gtgcggaccg agcggccgca ggaaccccta gtgatggagt tggccactcc ctctctgcgc   4080

gctcgctcgc tcactgaggc cgggcgacca aaggtcgccc gacgcccggg ctttgcccgg   4140

gcggcctcag tgagcgagcg agcgcgcagc tgcctgca                           4178
```

<210> SEQ ID NO 41
<211> LENGTH: 4181
<212> TYPE: DNA
<213> ORGANISM: Artificial sequence
<220> FEATURE:
<223> OTHER INFORMATION: Sequence of human Myo tail expression vector

<400> SEQUENCE: 41

```
ggcagctgcg cgctcgctcg ctcactgagg ccgcccgggc aaagcccggg cgtcgggcga     60

cctttggtcg cccggcctca gtgagcgagc gagcgcgcag agagggagtg gccaactcca    120

tcactagggg ttcctgcggc cgcacgcgtg gagctagtta ttaatagtaa tcaattacgg    180

ggtcattagt tcatagccca tatatggagt tccgcgttac ataacttacg gtaaatggcc    240

cgcctggctg accgcccaac gacccccgcc cattgacgtc aataatgacg tatgttccca    300

tagtaacgtc aatagggact ttccattgac gtcaatgggt ggagtattta cggtaaactg    360

cccacttggc agtacatcaa gtgtatcata tgccaagtac gccccctatt gacgtcaatg    420

acggtaaatg gcccgcctgg cattatgccc agtacatgac cttatgggac tttcctactt    480

ggcagtacat ctacgtatta gtcatcgcta ttaccatggt gatgcggttt tggcagtaca    540

tcaatgggcg tggatagcgg tttgactcac ggggatttcc aagtctccac cccattgacg    600

tcaatgggag tttgttttgc accaaaatca acgggacttt ccaaaatgtc gtaacaactc    660

cgccccattg acgcaaatgg gcggtaggcg tgtacggtgg gaggtctata taagcagagc    720

tcgtttagtg aaccgtcaga tcgcctggag acgccatcca cgctgttttg acctccatag    780

aagacaccgg gaccgatcca gcctccgcgg ccaccatgtt agcagaacaa aatatactgt    840

caagagacaa agtaatcaat gaactgaggc ttcgattgcc tgccactgca gaaagagaaa    900

agctcatagc tgagctaggc agaaaagaga tggaaccaaa atctcaccac acattgaaaa    960

ttgctcatca aaccattgca aacatgcaag caaggttaaa tcaaaaagaa gaagtattaa   1020

agaagtatca acgtcttcta gaaaaagcca gagaggagca aagagaaatt gtgaagaaac   1080
```

-continued

```
atgaggaaga ccttcatatt cttcatcaca gattagaact acaggctgat agttcactaa   1140
ataaattcaa acaaacggct tgggatttaa tgaaacagtc tcccactcca gttcctacca   1200
acaagcattt tattcgtctg gctgagatgg aacagacagt agcagaacaa gatgactctc   1260
tttcctcact cttggtcaaa ctaaagaaag tatcacaaga tttggagaga caaagagaaa   1320
tcactgaatt aaaagtaaaa gaatttgaaa atatcaaatt acagcttcaa gaaaaccatg   1380
aagatgaagt gaaaaaagta aaagcggaag tagaggattt aaagtatctt ctggaccagt   1440
cacaaaagga gtcacagtgt ttaaaatctg aacttcaggc tcaaaaagaa gcaaattcaa   1500
gagctccaac aactacaatg agaaatctag tagaacggct aaagagccaa ttagccttga   1560
aggagaaaca acagaaagca cttagtcggg cacttttaga actccgggca gaaatgacag   1620
cagctgctga agaacgtatt atttctgcaa cttctcaaaa agaggcccat ctcaatgttc   1680
aacaaatcgt tgatcgacat actagagagc taaagacaca agttgaagat ttaaatgaaa   1740
atcttttaaa attgaaagaa gcacttaaaa caagtaaaaa cagagaaaac tcactaactg   1800
ataatttgaa tgacttaaat aatgaactgc aaaagaaaca aaaagcctat aataaaatac   1860
ttagagagaa agaggaaatt gatcaagaga atgatgaact gaaaaggcaa attaaaagac   1920
taaccagtgg attacagggc aaacccctga cagataataa acaaagtcta attgaagaac   1980
tccaaaggaa agttaaaaaa ctagagaacc aattagaggg aaaggtggag gaagtagacc   2040
taaaacctat gaaagaaaag aatgctaaag aagaattaat taggtgggaa gaaggtaaaa   2100
agtggcaagc caaaatagaa ggaattcgaa acaagttaaa agagaaagag ggggaagtct   2160
ttactttaac aaagcagttg aatactttga aggatctttt tgccaaagcc gataaagaga   2220
aacttacttt gcagaggaaa ctaaaaacaa ctggcatgac tgttgatcag gttttgggaa   2280
tacgagcttt ggagtcagaa aaagaattgg aagaattaaa aaagagaaat cttgacttag   2340
aaaatgatat attgtatatg agggcccacc aagctcttcc tcgagattct gttgtagaag   2400
atttacattt acaaaataga tacctccaag aaaaacttca tgctttagaa aaacagtttt   2460
caaaggatac atattctaag ccttcaattt caggaataga gtcagatgat cattgtcaga   2520
gagaacagga gcttcagaag gaaaacttga agttgtcatc tgaaaatatt gaactgaaat   2580
ttcagcttga acaagcaaat aaagatttgc caagattaaa gaatcaagtc agagatttga   2640
aggaaatgtg tgaatttctt aagaaagaaa aagcagaagt tcagcggaaa cttggccatg   2700
ttagagggtc tggtagaagt ggaaagacaa tcccagaact ggaaaaaacc attggtttaa   2760
tgaaaaaagt agttgaaaaa gtccagagag aaaatgaaca gttgaaaaaa gcatcaggaa   2820
tattgactag tgaaaaaatg gctaatattg agcaggaaaa tgaaaaattg aaggctgaat   2880
tagaaaaact taaagctcat cttgggcatc agttgagcat gcactatgaa tccaagacca   2940
aaggcacaga aaaaattatt gctgaaaatg aaaggcttcg taaagaactt aaaaaagaaa   3000
ctgatgctgc agagaaatta cggatagcaa agaataattt agagatatta aatgagaaga   3060
tgacagttca actagaagag actggtaaga gattgcagtt tgcagaaagc agaggtccac   3120
agcttgaagg tgctgacagt aagagctgga aatccattgt ggttacaaga atgtatgaaa   3180
ccaagttaaa agaattggaa actgatattg ccaaaaaaaa tcaaagcatt actgacctta   3240
aacagcttgt aaaagaagca acagagagag aacaaaaagt taacaaatac aatgaagacc   3300
ttgaacaaca gattaagatt cttaaacatg ttcctgaagg tgctgagaca gagcaaggcc   3360
ttaaacggga gcttcaagtt cttagattag ctaatcatca gctggataaa gagaaagcag   3420
```

-continued

```
aattaatcca tcagatagaa gctaacaagg accaaagtgg agctgaaagc accatacctg   3480

atgctgatca actaaaggaa aaaataaaag atctagagac acagctcaaa atgtcagatc   3540

tagaaaagca gcatttgaag gaggaaataa agaagctgaa aaaagaactg gaaaattttg   3600

atccttcatt ttttgaagaa attgaagatc ttaagtataa ttacaaggaa gaagtgaaga   3660

agaatattct cttagaagag aaggtaaaaa aactttcaga acaattggga gttgaattaa   3720

ctagccctgt tgctgcttct gaagagtttg aagatgaaga agaaagtcct gttaatttcc   3780

ccatttacta aagatctaca tctcgctttc ttgctgtcca atttctatta aaggttcctt   3840

tgttccctaa gtccaactac taaactgggg gatattatga agggccttga gcatctggat   3900

tctgcctaat aaaaaacatt tattttcatt gcaatgatgt atttaaatta tttctgaata   3960

ttttactaaa aagggaatgt gggaggtcag tgcatttaaa acataaagaa agtaggtaac   4020

cacgtgcgga ccgagcggcc gcaggaaccc ctagtgatgg agttggccac tccctctctg   4080

cgcgctcgct cgctcactga ggccgggcga ccaaaggtcg cccgacgccc gggctttgcc   4140

cgggcggcct cagtgagcga gcgagcgcgc agctgcctgc a                       4181
```

<210> SEQ ID NO 42
<211> LENGTH: 2108
<212> TYPE: DNA
<213> ORGANISM: Artificial sequence
<220> FEATURE:
<223> OTHER INFORMATION: Sequence of mouse DSD expression vector

<400> SEQUENCE: 42

```
ggcagctgcg cgctcgctcg ctcactgagg ccgcccgggc aaagcccggg cgtcgggcga     60

cctttggtcg cccggcctca gtgagcgagc gagcgcgcag agagggagtg gccaactcca    120

tcactagggg ttcctgcggc cgcacgcgtg gagctagtta ttaatagtaa tcaattacgg    180

ggtcattagt tcatagccca tatatggagt tccgcgttac ataacttacg gtaaatggcc    240

cgcctggctg accgcccaac gacccccgcc cattgacgtc aataatgacg tatgttccca    300

tagtaacgtc aatagggact ttccattgac gtcaatgggt ggagtattta cggtaaactg    360

cccacttggc agtacatcaa gtgtatcata tgccaagtac gccccctatt gacgtcaatg    420

acggtaaatg gcccgcctgg cattatgccc agtacatgac cttatgggac tttcctactt    480

ggcagtacat ctacgtatta gtcatcgcta ttaccatggt gatgcggttt tggcagtaca    540

tcaatgggcg tggatagcgg tttgactcac ggggatttcc aagtctccac cccattgacg    600

tcaatgggag tttgttttgc accaaaatca acgggacttt ccaaaatgtc gtaacaactc    660

cgccccattg acgcaaatgg gcggtaggcg tgtacggtgg gaggtctata taagcagagc    720

tcgtttagtg aaccgtcaga tcgcctggag acgccatcca cgctgttttg acctccatag    780

aagacaccgg gaccgatcca gcctccgcgg ccaccatgga tttacttaag cagtctcctg    840

ctccagttcc caccaacaaa catttcattc gtctggccga gatggagcag acagtagcag    900

aacaagatga ctctctgtcc tcacttttga ccaaactaaa gaaagtatca aaagatttgg    960

aaaaacaaaa agaaatcact gagttaaaag tcagagagtt tgaaaatacc aaactacggc   1020

tccaagaaac tcatgccagt gaggtaaaga aagtgaaagc agaggtagag gacttaaggc   1080

atgctctagc ccaagcacac aaggactccc agagtttaaa gtctgaactc caggctcaga   1140

aagaagcaaa ctccagagct ccaacaacca caatgaggaa tcttgtagac aggctaaaga   1200

gccaactagc cttgaaagag aagcaacaaa aggcacttag tcgagccctg ttggaacttc   1260

ggtcggaaat gacagcagca gctgaggaac gtataatcgc tgtaacttct caaaaagagg   1320
```

```
caaatctcaa tgttcaacaa gttgttgagc gccatactag agagctaaag tcacaaattg   1380

aagatttaaa tgaaaatctt ttaaaattga aagaagctct taaaacaagt aagaacaaag   1440

aaaattcact agctgatgat ttaaatgaat taaataatga actgcaaaaa aagcaaaaag   1500

cttataataa aatccttaga gagaaagatg gaattgatca agaaaatgat gaactgagaa   1560

gacagattaa aagactgtcc agtggactgc agagcaaaac tttgatagat aacaagcaaa   1620

gtttaatcga tgaacttcaa aagaaagtta aaaaacttga aagccaactg gaaagaaagg   1680

tggatgacgt agacataaag ccggtgaagg aaaagtagag atctacatct cgctttcttg   1740

ctgtccaatt tctattaaag gttcctttgt tccctaagtc caactactaa actgggggat   1800

attatgaagg gccttgagca tctggattct gcctaataaa aaacatttat tttcattgca   1860

atgatgtatt taaattattt ctgaatattt tactaaaaag ggaatgtggg aggtcagtgc   1920

atttaaaaca taaagaaagt aggtaaccac gtgcggaccg agcggccgca ggaaccccta   1980

gtgatggagt tggccactcc ctctctgcgc gctcgctcgc tcactgaggc cgggcgacca   2040

aaggtcgccc gacgcccggg ctttgcccgg gcggcctcag tgagcgagcg agcgcgcagc   2100

tgcctgca                                                             2108
```

<210> SEQ ID NO 43
<211> LENGTH: 2108
<212> TYPE: DNA
<213> ORGANISM: Artificial sequence
<220> FEATURE:
<223> OTHER INFORMATION: Sequence of human DSD expression vector

<400> SEQUENCE: 43

```
ggcagctgcg cgctcgctcg ctcactgagg ccgcccgggc aaagcccggg cgtcgggcga     60

cctttggtcg cccggcctca gtgagcgagc gagcgcgcag agagggagtg gccaactcca    120

tcactagggg ttcctgcggc cgcacgcgtg gagctagtta ttaatagtaa tcaattacgg    180

ggtcattagt tcatagccca tatatggagt tccgcgttac ataacttacg gtaaatggcc    240

cgcctggctg accgcccaac gacccccgcc cattgacgtc aataatgacg tatgttccca    300

tagtaacgtc aatagggact ttccattgac gtcaatgggt ggagtattta cggtaaactg    360

cccacttggc agtacatcaa gtgtatcata tgccaagtac gccccctatt gacgtcaatg    420

acggtaaatg gcccgcctgg cattatgccc agtacatgac cttatgggac tttcctactt    480

ggcagtacat ctacgtatta gtcatcgcta ttaccatggt gatgcggttt tggcagtaca    540

tcaatgggcg tggatagcgg tttgactcac ggggatttcc aagtctccac cccattgacg    600

tcaatgggag tttgttttgc accaaaatca acgggacttt ccaaaatgtc gtaacaactc    660

cgccccattg acgcaaatgg gcggtaggcg tgtacggtgg gaggtctata taagcagagc    720

tcgtttagtg aaccgtcaga tcgcctggag acgccatcca cgctgttttg acctccatag    780

aagacaccgg gaccgatcca gcctccgcgg ccaccatgga tttaatgaaa cagtctccca    840

ctccagttcc taccaacaag cattttattc gtctggctga gatggaacag acagtagcag    900

aacaagatga ctctctttcc tcactcttgg tcaaactaaa gaaagtatca caagatttgg    960

agagacaaag agaaatcact gaattaaaag taaaagaatt tgaaaatatc aaattacagc   1020

ttcaagaaaa ccatgaagat gaagtgaaaa aagtaaaagc ggaagtagag gatttaaagt   1080

atcttctgga ccagtcacaa aaggagtcac agtgtttaaa atctgaactt caggctcaaa   1140

aagaagcaaa ttcaagagct ccaacaacta caatgagaaa tctagtagaa cggctaaaga   1200
```

gccaattagc cttgaaggag aaacaacaga aagcacttag tcgggcactt ttagaactcc 1260
gggcagaaat gacagcagct gctgaagaac gtattatttc tgcaacttct caaaaagagg 1320
cccatctcaa tgttcaacaa atcgttgatc gacatactag agagctaaag acacaagttg 1380
aagatttaaa tgaaaatctt ttaaaattga aagaagcact taaaacaagt aaaaacagag 1440
aaaactcact aactgataat ttgaatgact taaataatga actgcaaaag aaacaaaaag 1500
cctataataa aatacttaga gagaaagagg aaattgatca agagaatgat gaactgaaaa 1560
ggcaaattaa aagactaacc agtggattac agggcaaacc cctgacagat aataaacaaa 1620
gtctaattga agaactccaa aggaaagtta aaaaactaga gaaccaatta gagggaaagg 1680
tggaggaagt agacctaaaa cctatgaaag aaaagtagag atctacatct cgctttcttg 1740
ctgtccaatt tctattaaag gttcctttgt tccctaagtc caactactaa actgggggat 1800
attatgaagg gccttgagca tctggattct gcctaataaa aaacatttat tttcattgca 1860
atgatgtatt taaattattt ctgaatattt tactaaaaag ggaatgtggg aggtcagtgc 1920
atttaaaaca taaagaaagt aggtaaccac gtgcggaccg agcggccgca ggaaccccta 1980
gtgatggagt tggccactcc ctctctgcgc gctcgctcgc tcactgaggc cgggcgacca 2040
aaggtcgccc gacgcccggg ctttgcccgg gcggcctcag tgagcgagcg agcgcgcagc 2100
tgcctgca 2108

<210> SEQ ID NO 44
<211> LENGTH: 5132
<212> TYPE: DNA
<213> ORGANISM: Artificial sequence
<220> FEATURE:
<223> OTHER INFORMATION: Sequence of mouse C-terminal expression vector

<400> SEQUENCE: 44
ggcagctgcg cgctcgctcg ctcactgagg ccgcccgggc aaagcccggg cgtcgggcga 60
cctttggtcg cccggcctca gtgagcgagc gagcgcgcag agagggagtg gccaactcca 120
tcactagggg ttcctgcggc cgcacgcgtg gagctagtta ttaatagtaa tcaattacgg 180
ggtcattagt tcatagccca tatatggagt tccgcgttac ataacttacg gtaaatggcc 240
cgcctggctg accgcccaac gacccccgcc cattgacgtc aataatgacg tatgttccca 300
tagtaacgtc aatagggact ttccattgac gtcaatgggt ggagtattta cggtaaactg 360
cccacttggc agtacatcaa gtgtatcata tgccaagtac gccccctatt gacgtcaatg 420
acggtaaatg gcccgcctgg cattatgccc agtacatgac cttatgggac tttcctactt 480
ggcagtacat ctacgtatta gtcatcgcta ttaccatggt gatgcggttt tggcagtaca 540
tcaatgggcg tggatagcgg tttgactcac ggggatttcc aagtctccac cccattgacg 600
tcaatgggag tttgttttgc accaaaatca acgggacttt ccaaaatgtc gtaacaactc 660
cgccccattg acgcaaatgg gcggtaggcg tgtacggtgg gaggtctata taagcagagc 720
tcgtttagtg aaccgtcaga tcgcctggag acgccatcca cgctgttttg acctccatag 780
aagacaccgg gaccgatcca gcctccgcgg ccaccatgca acaacagtcc agggaaaagg 840
aagtggaatc cctcagaacg cagctgctgg acttccaggc acaatctgac gaaaaggctc 900
taattgccaa attgcaccaa catgttgtct ctcttcaaat tagtgaggcc actgccctcg 960
gtaagttaga gtcagttacg tccaaactcc agaagatgga agcctacaat ttgcgcttag 1020
aacagaaact ggatgaaaaa gagcaggcgc tctactatgc tcgtttggaa ggtagaaaca 1080
gagcaaaaca cctgcgccaa accattcagt cgcttcgaag acagttcagt ggagctctac 1140

-continued

```
ccttagcaca gcaggaaaag ttctccaaaa cgatgattca gttgcaaaat gacaaactta   1200
agataatgca agaaatgaag aattcgcaac aggaacacag aaatatggaa aacaaaacac   1260
tggagttgga attaaaatta aaaggcttag aagaattgat cagtacttta aaggatgcca   1320
ggggagccca gaaggtaatc aattggcatg tgaaaataga agaacttcgc ctccaagaac   1380
ttaagctaaa tagagaacta gtcaagggta aagaagaaat caaatatttg aataatatca   1440
tctctgaata tgagcataca atcaacagtc tagaggaaga aattgttcag caaagcaagt   1500
tccatgaaga aagacagatg gcttgggatc aaagagaagt tgagctggaa cgccagttag   1560
acatttttga tcatcagcaa aatgaaatac tcagtgcagc acaaaagttt gaagactcta   1620
caggatcaat gccagacccc agcttgcctc ttccaaacca acttgaaatt gctctaagaa   1680
aaattaagga gaatattcaa gtaattctta aaacacaagc aacttgcaag tcactagaag   1740
agaaactaaa agaaaaagaa tctgctttac ggttggcaga gcaaaatatt ctgtcaagag   1800
acaaagtaat caatgaactg aggcttcgat tgcctgccac ggctgatcga gaaaaactta   1860
tagctgagct agaaagaaaa gagctggagc cgaaatctca tcacacaatg aaaattgccc   1920
accaaactat tgccaacatg caggcaaggt taaatcacaa ggaagaagta ttgaagaaat   1980
accagcacct tctggagaag gccagagagg agcaaagaga aattgttaag aagcatgagg   2040
aagaccttca tgttcttcat cacaaattag aacaacaggc cgataattca ctcaataaat   2100
tcagacagac agctcaggat ttacttaagc agtctcctgc tccagttccc accaacaaac   2160
atttcattcg tctggccgag atggagcaga cagtagcaga acaagatgac tctctgtcct   2220
cacttttgac caaactaaag aaagtatcaa aagatttgga aaaacaaaaa gaaatcactg   2280
agttaaaagt cagagagttt gaaaatacca aactacggct ccaagaaact catgccagtg   2340
aggtaaagaa agtgaaagca gaggtagagg acttaaggca tgctctagcc caagcacaca   2400
aggactccca gagtttaaag tctgaactcc aggctcagaa agaagcaaac tccagagctc   2460
caacaaccac aatgaggaat cttgtagaca ggctaaagag ccaactagcc ttgaaagaga   2520
agcaacaaaa ggcacttagt cgagccctgt tggaacttcg gtcggaaatg acagcagcag   2580
ctgaggaacg tataatcgct gtaacttctc aaaaagaggc aaatctcaat gttcaacaag   2640
ttgttgagcg ccatactaga gagctaaagt cacaaattga agatttaaat gaaaatcttt   2700
taaaattgaa agaagctctt aaaacaagta agaacaaaga aaattcacta gctgatgatt   2760
taaatgaatt aaataatgaa ctgcaaaaaa agcaaaaagc ttataataaa atccttagag   2820
agaaagatgg aattgatcaa gaaaatgatg aactgagaag acagattaaa agactgtcca   2880
gtggactgca gagcaaaact ttgatagata acaagcaaag tttaatcgat gaacttcaaa   2940
agaaagttaa aaaacttgaa agccaactgg aaagaaaggt ggatgacgta gacataaagc   3000
cggtgaagga aaagagtagt aaagaagaat taattaggtg ggaagaaggt aagaaatggc   3060
aaaccaaagt agagggacta cgaaacagac taaaggagaa ggaaggagaa gcccacggcc   3120
tggcaaagca gctgaatacc ttaaaggaac tttttgccaa agctgataaa gagaaactta   3180
ctttgcagaa gaaactgaaa acaacaggaa tgactgttga ccaggtttta ggagtgcgag   3240
ctttggaatc tgaaaaagag ttggaagagc taaaaaagaa aaatctggac ctagaaaatg   3300
acatattata catgaggacc cagcaggctc ttccacgaga ttctgttgtg gaagacttac   3360
atttacaaaa taaatacctt caagaaaaac ttcatacttt agaaaaaaaa ctttcaaagg   3420
agaaatattc tcagtctttg acttcagaaa tagagtcaga tgatcactgt caaaaagaac   3480
```

aagaacttca gaaggaaaat ttgaagttgt catctgaaaa catcgagctg aaatttcaac 3540
ttgaacaagc aaataaagat ttgccaagac taaagaatca agtgaaagat ttgaaggaaa 3600
tgtgtgaatt tcttaagaaa ggaaaactgg aacttgagcg gaagcttggt caggtcagag 3660
gggctggtag aagtgggaag acaatcccag aactagaaaa aaccattggg ttaatgaaga 3720
aagtagttga aaaagtccaa agagaaaatg aacaattgaa aaaggcatca ggaatactga 3780
ctagtgaaaa aatggctact attgaggaag aaaatagaaa cttaaaggct gaactagaaa 3840
agcttaaagc tcactttgga cgtcagttga gtatgcagtt tgaatctaag aacaaaggta 3900
ctgagaaaat tgttgccgaa aatgaacggc ttcggaaaga acttaagaaa gaaatagaag 3960
cctctgagaa actgcggata gctaagaaca acttagagct ggtgaacgac aagatggcag 4020
ctcaactcga agaaactggg aagagactac agtttgcaga aagtagagcc ccacagctgg 4080
aaggtgctga cagcaagagc tggaagtcaa ttgtggtctc aagagtgtat gagaccaaga 4140
tgaaagagct tgaaagtgac attgccaaaa agaatcaaag tatcactgac cttaaacagc 4200
ttgtaagaga agcaacagag agagaacaga aagctaagaa atacactgaa gaccttgaac 4260
aacagattga gatcctcaaa aatgttcctg aaggtgccga gacagagcaa gagcttatac 4320
gggaactcca gcttcttaga ttagccaata atcagatgga taaagaaagg gcagaattaa 4380
tccatcagat agaaattaac aaggaccaaa ccagagctga cagtagcata cctgattctg 4440
atcaactaaa ggaaaagata aatgacctgg agacacaact cagaaagttg gagctagaaa 4500
agcaacattc gaaggaggaa gttaaaaagc tgaaaaaaga actggaaaat tttgatcctt 4560 catttttga agaaattgaa gacctgaagt ataattataa ggaagaagtg aaaaagaata 4620
tcctattaga agagaagcta aaaaaactgt cggaacagtt tggatttgaa ctgcctagtc 4680
ctcttgctgc ttctgaacac tcggaagatg gagaaagtcc tcatagtttc cctatttatt 4740
agagatctac atctcgcttt cttgctgtcc aatttctatt aaaggttcct ttgttcccta 4800
agtccaacta ctaaactggg ggatattatg aagggccttg agcatctgga ttctgcctaa 4860
taaaaaacat ttattttcat tgcaatgatg tatttaaatt atttctgaat attttactaa 4920
aaagggaatg tgggaggtca gtgcatttaa aacataaaga aagtaggtaa ccacgtgcgg 4980
accgagcggc cgcaggaacc cctagtgatg gagttggcca ctccctctct gcgcgctcgc 5040
tcgctcactg aggccgggcg accaaaggtc gcccgacgcc cgggctttgc ccgggcggcc 5100
tcagtgagcg agcgagcgcg cagctgcctg ca 5132

<210> SEQ ID NO 45
<211> LENGTH: 5132
<212> TYPE: DNA
<213> ORGANISM: Artificial sequence
<220> FEATURE:
<223> OTHER INFORMATION: Sequence of human C-terminal expression vector

<400> SEQUENCE: 45
ggcagctgcg cgctcgctcg ctcactgagg ccgcccgggc aaagcccggg cgtcgggcga 60
cctttggtcg cccggcctca gtgagcgagc gagcgcgcag agagggagtg gccaactcca 120
tcactagggg ttcctgcggc cgcacgcgtg gagctagtta ttaatagtaa tcaattacgg 180
ggtcattagt tcatagccca tatatggagt tccgcgttac ataacttacg gtaaatggcc 240
cgcctggctg accgcccaac gacccccgcc cattgacgtc aataatgacg tatgttccca 300
tagtaacgtc aatagggact ttccattgac gtcaatgggt ggagtattta cggtaaactg 360
cccacttggc agtacatcaa gtgtatcata tgccaagtac gccccctatt gacgtcaatg 420

-continued

```
acggtaaatg gcccgcctgg cattatgccc agtacatgac cttatgggac tttcctactt    480
ggcagtacat ctacgtatta gtcatcgcta ttaccatggt gatgcggttt tggcagtaca    540
tcaatgggcg tggatagcgg tttgactcac ggggatttcc aagtctccac cccattgacg    600
tcaatgggag tttgttttgc accaaaatca acgggacttt ccaaaatgtc gtaacaactc    660
cgccccattg acgcaaatgg gcggtaggcg tgtacggtgg gaggtctata taagcagagc    720
tcgtttagtg aaccgtcaga tcgcctggag acgccatcca cgctgttttg acctccatag    780
aagacaccgg gaccgatcca gcctccgcgg ccaccatgca acaatctagg gacaaggaag    840
tagagtccct cagaatgcaa ctgctagact atcaggcaca gtctgatgaa aagtcgctca    900
ttgccaagtt gcaccaacat aatgtctctc ttcaactgag tgaggctact gctcttggta    960
agttggagtc aattacatct aaactgcaga agatggaggc ctacaacttg cgcttagagc   1020
agaaacttga tgaaaaagaa caggctctct attatgctcg tttggaggga agaaacagag   1080
caaaacatct gcgccaaaca attcagtctc tacgacgaca gtttagtgga gctttaccct   1140
tggcacaaca ggaaaagttc tccaaaacaa tgattcaact acaaaatgac aaacttaaga   1200
taatgcaaga aatgaaaaat tctcaacaag aacatagaaa tatggagaac aaaacattgg   1260
agatggaatt aaaattaaag ggcctggaag agttaataag cactttaaag gataccaaag   1320
gagcccaaaa ggtaatcaac tggcatatga aaatagaaga acttcgtctt caagaactta   1380
aactaaatcg ggaattagtc aaggataaag aagaaataaa atatttgaat aacataattt   1440
ctgaatatga acgtacaatc agcagtcttg aagaagaaat tgtgcaacag aacaagtttc   1500
atgaagaaag acaaatggcc tgggatcaaa gagaagttga cctggaacgc caactagaca   1560
tttttgaccg tcagcaaaat gaaatactaa atgcggcaca aaagtttgaa gaagctacag   1620
gatcaatccc tgaccctagt ttgccccttc caaatcaact tgagatcgct ctaaggaaaa   1680
ttaaggagaa cattcgaata attctagaaa cacgggcaac ttgcaaatca ctagaagaga   1740
aactaaaaga gaaagaatct gctttaaggt tagcagaaca aaatatactg tcaagagaca   1800
aagtaatcaa tgaactgagg cttcgattgc ctgccactgc agaaagagaa aagctcatag   1860
ctgagctagg cagaaaagag atggaaccaa aatctcacca cacattgaaa attgctcatc   1920
aaaccattgc aaacatgcaa gcaaggttaa atcaaaaaga agaagtatta aagaagtatc   1980
aacgtcttct agaaaaagcc agagaggagc aaagagaaat tgtgaagaaa catgaggaag   2040
accttcatat tcttcatcac agattagaac tacaggctga tagttcacta aataaattca   2100
aacaaacggc ttgggattta atgaaacagt ctcccactcc agttcctacc aacaagcatt   2160
ttattcgtct ggctgagatg gaacagacag tagcagaaca agatgactct ctttcctcac   2220
tcttggtcaa actaaagaaa gtatcacaag atttggagag acaaagagaa atcactgaat   2280
taaaagtaaa agaatttgaa aatatcaaat tacagcttca agaaaaccat gaagatgaag   2340
tgaaaaaagt aaaagcggaa gtagaggatt taaagtatct tctggaccag tcacaaaagg   2400
agtcacagtg tttaaaatct gaacttcagg ctcaaaaaga agcaaattca agagctccaa   2460
caactacaat gagaaatcta gtagaacggc taaagagcca attagccttg aaggagaaac   2520
aacagaaagc acttagtcgg gcacttttag aactccgggc agaaatgaca gcagctgctg   2580
aagaacgtat tatttctgca acttctcaaa aagaggccca tctcaatgtt caacaaatcg   2640
ttgatcgaca tactagagag ctaaagacac aagttgaaga tttaaatgaa aatcttttaa   2700
aattgaaaga agcacttaaa acaagtaaaa acagagaaaa ctcactaact gataatttga   2760
```

-continued

```
atgacttaaa taatgaactg caaaagaaac aaaaagccta taataaaata cttagagaga   2820
aagaggaaat tgatcaagag aatgatgaac tgaaaaggca aattaaaaga ctaaccagtg   2880
gattacaggg caaacccctg acagataata aacaaagtct aattgaagaa ctccaaagga   2940
aagttaaaaa actagagaac caattagagg gaaaggtgga ggaagtagac ctaaaaccta   3000
tgaaagaaaa gaatgctaaa gaagaattaa ttaggtggga agaaggtaaa aagtggcaag   3060
ccaaaataga aggaattcga aacaagttaa aagagaaaga gggggaagtc tttactttaa   3120
caaagcagtt gaatactttg aaggatcttt ttgccaaagc cgataaagag aaacttactt   3180
tgcagaggaa actaaaaaca actggcatga ctgttgatca ggttttggga atacgagctt   3240
tggagtcaga aaaagaattg gaagaattaa aaaagagaaa tcttgactta gaaaatgata   3300
tattgtatat gagggcccac caagctcttc ctcgagattc tgttgtagaa gatttacatt   3360
tacaaaatag atacctccaa gaaaaacttc atgctttaga aaaacagttt tcaaaggata   3420
catattctaa gccttcaatt tcaggaatag agtcagatga tcattgtcag agagaacagg   3480
agcttcagaa ggaaaacttg aagttgtcat ctgaaaatat tgaactgaaa tttcagcttg   3540
aacaagcaaa taaagatttg ccaagattaa agaatcaagt cagagatttg aaggaaatgt   3600
gtgaatttct taagaaagaa aaagcagaag ttcagcggaa acttggccat gttagagggt   3660
ctggtagaag tggaaagaca atcccagaac tggaaaaaac cattggttta atgaaaaaag   3720
tagttgaaaa agtccagaga gaaaatgaac agttgaaaaa agcatcagga atattgacta   3780
gtgaaaaaat ggctaatatt gagcaggaaa atgaaaaatt gaaggctgaa ttagaaaaac   3840
ttaaagctca tcttgggcat cagttgagca tgcactatga atccaagacc aaaggcacag   3900
aaaaaattat tgctgaaaat gaaaggcttc gtaaagaact taaaaaagaa actgatgctg   3960
cagagaaatt acggatagca aagaataatt tagagatatt aaatgagaag atgacagttc   4020
aactagaaga gactggtaag agattgcagt ttgcagaaag cagaggtcca cagcttgaag   4080
gtgctgacag taagagctgg aaatccattg tggttacaag aatgtatgaa accaagttaa   4140
aagaattgga aactgatatt gccaaaaaaa atcaaagcat tactgacctt aaacagcttg   4200
taaaagaagc aacagagaga gaacaaaaag ttaacaaata caatgaagac cttgaacaac   4260
agattaagat tcttaaacat gttcctgaag gtgctgagac agagcaaggc cttaaacggg   4320
agcttcaagt tcttagatta gctaatcatc agctggataa agagaaagca gaattaatcc   4380
atcagataga agctaacaag gaccaaagtg gagctgaaag caccatacct gatgctgatc   4440
aactaaagga aaaaataaaa gatctagaga cacagctcaa aatgtcagat ctagaaaagc   4500
agcatttgaa ggaggaaata aagaagctga aaaaagaact ggaaaatttt gatccttcat   4560
tttttgaaga aattgaagat cttaagtata attacaagga agaagtgaag aagaatattc   4620
tcttagaaga gaaggtaaaa aaactttcag aacaattggg agttgaatta actagccctg   4680
ttgctgcttc tgaagagttt gaagatgaag aagaaagtcc tgttaatttc cccatttact   4740
aaagatctac atctcgcttt cttgctgtcc aatttctatt aaaggttcct ttgttcccta   4800
agtccaacta ctaaactggg ggatattatg aagggccttg agcatctgga ttctgcctaa   4860
taaaaaacat ttattttcat tgcaatgatg tatttaaatt atttctgaat attttactaa   4920
aaagggaatg tgggaggtca gtgcatttaa aacataaaga aagtaggtaa ccacgtgcgg   4980
accgagcggc cgcaggaacc cctagtgatg gagttggcca ctccctctct gcgcgctcgc   5040
```

-continued

```
tcgctcactg aggccgggcg accaaaggtc gcccgacgcc cgggctttgc ccgggcggcc    5100

tcagtgagcg agcgagcgcg cagctgcctg ca                                  5132
```